United States Patent
Heller et al.

(10) Patent No.: US 11,097,019 B2
(45) Date of Patent: Aug. 24, 2021

(54) HELICAL POLYCARBODIIMIDE POLYMERS AND ASSOCIATED IMAGING, DIAGNOSTIC, AND THERAPEUTIC METHODS

(71) Applicant: Memorial Sloan Kettering Cancer Center, New York, NY (US)

(72) Inventors: Daniel Heller, New York, NY (US); Januka Budhathoki-Uprety, New York, NY (US)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 19 days.

(21) Appl. No.: 16/237,492

(22) Filed: Dec. 31, 2018

(65) Prior Publication Data
US 2019/0374661 A1     Dec. 12, 2019

Related U.S. Application Data

(63) Continuation of application No. 14/826,712, filed on Aug. 14, 2015, now abandoned.
(Continued)

(51) Int. Cl.
| | |
|---|---|
| *A61K 9/00* | (2006.01) |
| *A61K 51/06* | (2006.01) |
| *A61K 51/12* | (2006.01) |
| *G01N 33/58* | (2006.01) |
| *G01N 33/542* | (2006.01) |
| *A61K 47/69* | (2017.01) |

(Continued)

(52) U.S. Cl.
CPC ............ *A61K 51/065* (2013.01); *A61K 47/59* (2017.08); *A61K 47/6927* (2017.08); *A61K 51/1251* (2013.01); *C01B 32/168* (2017.08); *G01N 33/542* (2013.01); *G01N 33/587* (2013.01)

(58) Field of Classification Search
CPC ..................................................... A61K 51/065
See application file for complete search history.

(56) References Cited

U.S. PATENT DOCUMENTS

| | | | |
|---|---|---|---|
| 2003/0026764 A1* | 2/2003 | Griffiths | A61K 47/646 424/9.34 |
| 2009/0221766 A1* | 9/2009 | Cheng | C07D 489/02 525/540 |

FOREIGN PATENT DOCUMENTS

WO    WO-2010/104253 A1    9/2010

OTHER PUBLICATIONS

Budhathoki-Uprety, J. et al., Helical Polycarbodiimide Cloaking of Carbon Nanotubes Enables Inter-Nanotube Exciton Energy Transfer Modulation, J. Am. Chem. Soc., 136:15545-15550 (2014).

(Continued)

*Primary Examiner* — Paul W Dickinson
(74) *Attorney, Agent, or Firm* — Foley & Lardner LLP

(57) ABSTRACT

Described herein are suspensions of helical polycarbodiimide polymers that 'cloak' nanotubes, thereby effecting control over nanotube emission, providing a new mechanism of environmental responsivity, and enabling precise control over sub-cellular localization. The helical polycarbodiimide polymers described herein are water soluble, easily modifiable, and have unique architectures that facilitate their application in radiopharmaceutical delivery and imaging methods, in therapeutics and therapeutic delivery methods, and their use as sensors—both in conjunction with carbon nanotubes, and without nanotubes.

14 Claims, 52 Drawing Sheets

Related U.S. Application Data

(60) Provisional application No. 62/038,235, filed on Aug. 16, 2014.

(51) Int. Cl.
*A61K 47/59* (2017.01)
*C01B 32/168* (2017.01)

(56) References Cited

OTHER PUBLICATIONS

Budhathoki-Uprety, J. et al., Synthesis of Guanidinium Funcitonalized Polycarbodiimides and Their Antibacterial Activities, ACS Macro Lett. 1:370-374 2012.

Budhathoki-Uprety, Januka and Novak, Bruce M., Synthesis of Alkyne-Functionalized Helical Plycarbodiimides and their Ligation to Small Molecules using 'Click' and Sonogashira Reactions, Macromolecules, 44:5947-5954 2011.

Deri, M. A. et al., Alternative Chelator for Zr Radiopharmaceuticals: Radiolabeling and Evaluation of 3,4,3-Li-1,2-HOPO , J. Med. Chem. 57:4849-4860 2014.

Hu, Chang-Yuan et al., Non-Covalent Functionalization of Carbon Nanotubes with Surfactants and Polymers, Journal of the Chinese Chemical Society, 56:234-239 (2009).

International Search Report and Written Opinion on PCT/US2015/045278 dated Jan. 14, 2016 (13 pages).

Inverarity, I. A. and Hulme, A. N., Marked small molecule libraries: a truncated approach to molecular probe design, Or. Biomol. Chem., 5(4):636-643 (2007).

Kennemur, J. G. et al., A New, More Versatile, Optical Switching Helical Polycarbodiimide Ca able of Thermal! Turn in Polarization +−359, Macromolecules 43:1867-1873 (2010).

Orcutt, K. D. et al., Engineering an antibody with picomolar affinity to DOTA chelates of multiple radionuclides for pretargeted radioimmunotherapy and imaging, Nuclear Medicine and Biology, 28:223-233 (2011).

Srinivasan. R. et al., High-throughput synthesis of azide libraries suitable for direct "click" chemistr and insitu screenin , Or an. Biomol. chem., 7(9):1821-1828 (2009).

Tang, H.Z. et al., Chiroptical Switching Polyguanidine Synthesized by Helix-Sense-Selective Polymerization Using [(R)-3,3'-Dibromo-2,2'binaphthoxy](di-tert-butoxy)titanium(IV) Catalyst, J. Am. Chem. Soc., 127:2136-2142 (2005).

\* cited by examiner

HELICAL POLYCARBODIIMIDE POLYMERS AND ASSOCIATED IMAGING, DIAGNOSTIC, AND THERAPEUTIC METHODS

CROSS-REFERENCE TO RELATED APPLICATIONS

This application is a continuation of U.S. patent application Ser. No. 14/826,712, filed Aug. 14, 2015, which claims priority to and the benefit of U.S. Provisional Patent Application No. 62/038,235, filed Aug. 16, 2014, the entire contents of each of which are incorporated herein by reference.

GOVERNMENT SUPPORT

This invention was made with government support under grant number HD075698 awarded by the National Institutes of Health. The government has certain rights in the invention.

FIELD OF THE INVENTION

This invention relates generally to compositions comprising polycarbodiimide polymers, and related imaging, diagnostic, and therapeutic methods.

BACKGROUND

Carbon nanotubes have several features which demonstrate their potential for biomedical applications including cellular sensing and imaging. For example, carbon nanotubes can be metallic or semiconducting depending on their structure, which is due to the symmetry and unique electronic structure of graphene. Thus, the electronic structure and diameter of the 4814-1338-8707.1 carbon nanotube will determine the spectral characteristics seen in absorption, fluorescence, Raman scattering, etc. Moreover, the environmental sensitivity and intrinsic photostability of single-walled carbon nanotubes (SWCNTs) in the near-infrared wavelength range (ca. 900 nm-1600 nm) demonstrates the potential of biomedical applications. However, such uses require the ability to simultaneously modulate nanotube fluorescence and to biocompatibly derivatize the nanotube surface using noncovalent methods.

Both covalent and non-covalent functionalization methods can be used to solubilize carbon nanotubes for adaption to biomedical applications. Non-covalent functionalization of SWCNTs preserves both the optical and structural properties of SWCNTs in solution. Nanotubes can be encapsulated in various amphiphilic polymers. Biopolymers such as single stranded DNA (ssDNA), peptides, or proteins, and synthetic polymers, such as polyfluorenes, polycarbazoles, aryleneethynylene polymers, polyethylene glycol (PEG) derivatives, and dextran-based polymers have been investigated for materials, and biological applications. However, encapsulation with biopolymers can produce higher background signal (e.g., DNA can produce high oxidation current and subsequently higher background currents) or provide inadequate control of coating the nanotube and therefore affect optical response (e.g., protein denaturation in unfavorable conditions). Moreover, the above-mentioned synthetic polymers do not provide controllable and/or tunable properties, which limit the ability to measure (e.g., via imaging) the kinetics of dynamic self-assembly and disassembly and translocation of photoluminescent nanotubes into live cell nuclei.

Therefore, there is a need to better adapt carbon nanotubes for biomedical applications, such as cellular imaging and sensing, that provides control over nanotube emission, environmental responsivity, precise control over sub-cellular localization, ordered surface coverage, and systematic modulation of nanotube optical properties.

SUMMARY OF INVENTION

Described herein are suspensions of helical polycarbodiimide polymers that 'cloak' nanotubes, thereby effecting control over nanotube emission, providing a new mechanism of environmental responsivity, and enabling precise control over sub-cellular localization. The helical polycarbodiimide polymers described herein are water soluble, easily modifiable, and have unique architectures that facilitate their application in radiopharmaceutical delivery and imaging methods, in therapeutics and therapeutic delivery methods, and their use as sensors—both in conjunction with carbon nanotubes, and without nanotubes.

For example, the helical polycarbodiimide polymers can be modified with radionuclides or radionuclide-chelating agents. Experiments performed with these polymers—for example, DOTA-modified polymer with multiple chelation sites for Lutetium-177—demonstrate rapid clearance and low organ update, especially in the kidneys.

The helical polycarbodiimide polymers can also deliver molecules and increase drug binding affinity via multivalency, lending to their use as therapeutics and in therapeutic delivery, for example, opiate-polymer conjugates that provide long-term analgesic effects, as well as treatment of cancer, atherosclerosis, skin disorders, infectious diseases, and other diseases. Due to the semi-rigidity of the polymer, more binding sites are accessible, compared with polymers having a globular form. Furthermore, the helical polymer lengths are short and very controllable, allowing for rapid clearance if desired.

Moreover, the helical polymers described herein are demonstrated to encapsulate single-walled carbon nanotubes, which are used as fluorescent sensors for in vitro, ex vivo, and in vivo applications. The polymers provide both sensitivity to specific, desired bioanalytes, and direct/target the sensors to specific locations in the cell and body. Polymer-nanotube constructs are shown that provide nuclear, cytosolic, and extracellular localization. Moreover, a stable polymer-nanotube sensor is presented for in vitro and in vivo redox potential measurements.

In one aspect, the invention is directed to a suspension of helical-polymer-encapsulated carbon nanotubes, wherein the helical polymer is a polycarbodiimide. In certain embodiments, the carbon nanotubes are single-walled carbon nanotubes (SWCNTs). In certain embodiments, the helical polymer comprises a clickable polymer scaffold. In certain embodiments, the polycarbodiimide comprises one or more monomeric species selected from the group consisting of

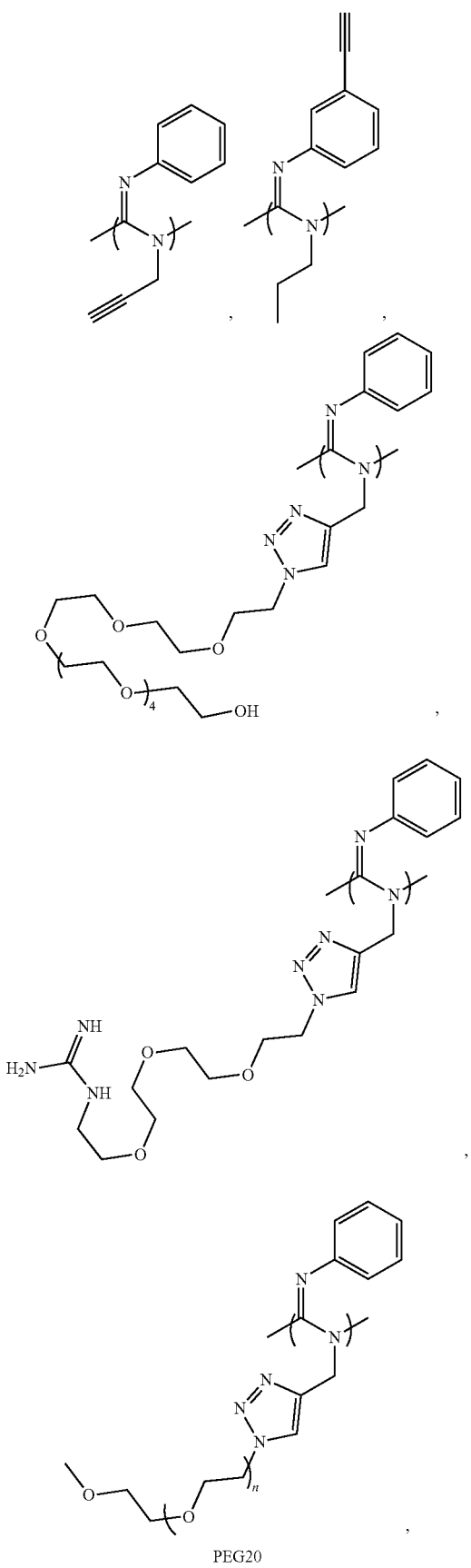

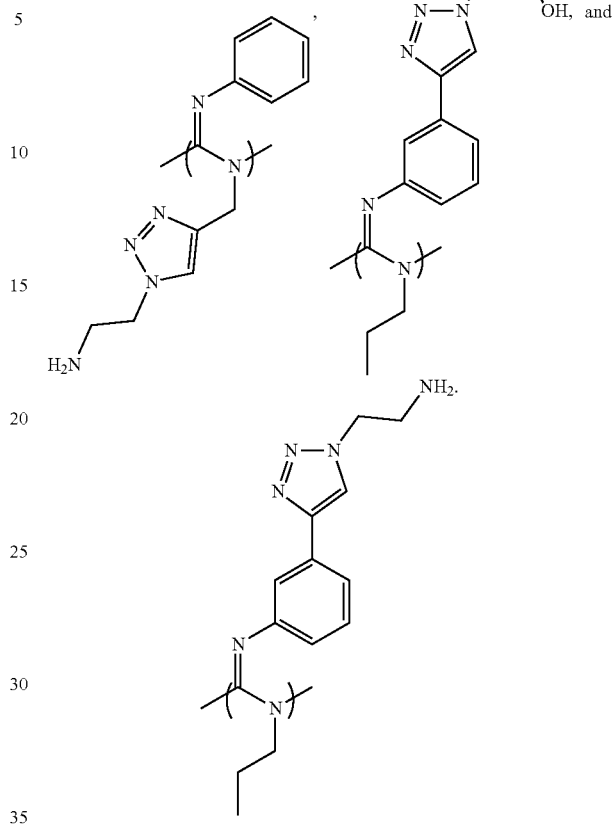

In certain embodiments, the suspension is an aqueous suspension. In certain embodiments, at least a plurality of the helical-polymer-encapsulated carbon nanotubes in the suspension are in van der Waals contact at a center-to-center distance between adjacent nanotubes sufficient to exhibit inter-nanotube Förster resonance energy transfer (INFRET). In certain embodiments, the center-to-center distance is from 1 nm to 4 nm. In certain embodiments, the dispersed helical-polymer-encapsulated carbon nanotubes in van der Waals contact are not irreversibly bound.

In certain embodiments, the suspension comprises (i) a first set of nanotubes each encapsulated by a helical polymer having at least a first substituent functional group (e.g., a primary amine), and (ii) a second set of nanotubes each encapsulated by a helical polymer having at least a second substituent functional group (e.g., a carboxylic acid), wherein the first substituent functional group and the second substituent functional group imbue the first and second sets of encapsulated nanotubes with sufficiently strong coulombic attraction to each other to form reversible fluorescent aggregates in the suspension.

In certain embodiments, the helical polymer comprises functional side chains. In certain embodiments, the functional side chains comprise one or more members selected from the group consisting of a primary amine, a carboxylic acid, a guanidine group, an oligoethylene glycol, a methoxy-polyethylene glycol (PEG), a hydroxyl-PEG, a folic acid, a trimethoprim, a peptide, an alkyne peptide, an adenosine triphosphate (ATP) peptide, and an opioid. In certain embodiments, the helical polymer comprises one or more aromatic groups incorporated in its monomer substituents. In certain embodiments, the one or more aromatic groups promote multi-valent π-π interactions between the polymer and the graphitic sidewall of the carbon nanotubes.

In certain embodiments, the functional side chains comprise a targeting group (e.g., an organelle targeting group, a protein targeting group, a polysaccharide targeting group, or a targeting group for another biological structure). In certain embodiments, a biomolecular imaging probe and/or sensor comprises the suspension.

In another aspect, the invention is directed to an imaging method comprising: administering the suspension to a biological sample (e.g., in vitro, ex vivo, or in vivo, e.g., wherein the biological sample is a subject); exposing the biological sample comprising the administered suspension to excitation light (e.g., near-infrared excitation light); and detecting light emitted by suspension or fluorescent aggregates formed by one or more components of the suspension (e.g., detecting light by inter-nanotube Førster resonance energy transfer (INFRET)) in the biological sample).

In certain embodiments, the imaging method comprises disrupting the fluorescent aggregates (e.g., wherein disrupting the fluorescent aggregates is performed by administering an agent) to reverse the emission of light.

In certain embodiments, the imaging method comprises alternating between cycles of light emission and no light emission by re-aggregating and disrupting, respectively, the fluorescent aggregates (e.g., for high resolution biomolecular imaging).

In certain embodiments, the detecting step comprises obtaining images of cellular nuclei of the biological sample.

In another aspect, the invention is directed to a method of treating a disease or disorder (e.g., cervical, pancreatic, or skin cancer), the method comprising administering the suspension to a subject, wherein the functional side chains of the helical polymer comprises a therapeutic.

In certain embodiments, the therapeutic comprises an opiate.

In another aspect, the invention is directed to a method for pretargeted radioimmunotherapy (PRIT), the method comprising administering a polycarbodiimide functionalized with an antibody, labeled with a radionuclide (e.g., wherein administering the labeled and functionalized polycarbodiimide delivers cytotoxic radiation to a target cell of the subject).

In certain embodiments, the radionuclide comprises a metallic lanthanide (e.g., yttrium or lutetium). In certain embodiments, the radionuclide is attached to the polycarbodiimide via a chelator (e.g., 1,4,7,10-tetraazacyclododecane-1,4,7,10-tetraacetic acid (DOTA) or desferoxamine (DFO)). In certain embodiments, the radionuclide comprises $^{89}$Zr.

In certain embodiments, the suspension is a stable suspension (e.g., stable in aqueous solution or in serum).

In another aspect, the invention is directed to a polycarbodiimide polymer having a helical conformation comprising one or more functional groups (e.g., functional side chains).

In certain embodiments, the one or more functional groups comprise at least one member selected from the group consisting of a primary amine, a carboxylic acid, a guanidine group, an oligoethylene glycol, a methoxy-PEG, a hydroxyl-PEG, a folic acid, a DOTA (1,4,7,10-tetraazacyclododecane-1,4,7,10-tetraacetic acid) or another chelator or complexing agent, a trimethoprim, a perphenazine, a peptide, an alkyne peptide, an ATP peptide, and an opioid.

In certain embodiments, the polymer is labeled with a radionuclide. In certain embodiments, the radionuclide comprises a metallic lanthanide (e.g., yttrium or lutetium). In certain embodiments, the radionuclide is attached to the polycarbodiimide via a chelator (e.g., 1,4,7,10-tetraazacyclododecane-1,4,7,10-tetraacetic acid (DOTA) or deferoxamine (DFO)). In certain embodiments, the radionuclide comprises $^{89}$Zr.

In certain embodiments, the polymer is functionalized with an antibody.

In certain embodiments, the polymer comprises a fluorophore. In certain embodiments, fluorophore is an infrared (IR) dye.

In certain embodiments, the polymer comprises a therapeutic (e.g., an opiate, e.g., octreotide).

In certain embodiments, the polymer comprises multimeric targeting groups (e.g., for receptors in cancer cells).

In another aspect, the invention is directed to a method of treating a disease or disorder, the method comprising administering the polymer to a subject, wherein the polymer is functionalized with a therapeutic.

In another aspect, the invention is directed to a method for radiotherapy (e.g., PRIT), the method comprising administering the polymer to a subject, wherein the polymer is functionalized with a radionuclide.

In another aspect, the invention is directed to an imaging method comprising: administering the polymer to a biological sample (e.g., wherein the administering is in vitro, ex vivo, or in vivo, e.g., wherein the biological sample is a subject); exposing the biological sample comprising the administered suspension to excitation light (e.g., near-infrared excitation light); and detecting electromagnetic radiation emitted by at least one of the one or more functional groups of the polymer.

In certain embodiments, the method further comprises exposing the biological sample to excitation light (e.g., near-infrared excitation light) prior to (and/or concurrent with) the detecting step, wherein the detecting step comprises detecting emitted fluorescent light.

In another aspect, the invention is directed to a helical-polymer-encapsulated carbon nanotube, wherein the helical-polymer is a polycarbodiimide.

In certain embodiments, the carbon nanotube is in a solid form (e.g., powdered or adhered to a surface) and capable of forming a stable suspension in solution (e.g., aqueous solution, e.g., serum).

In another aspect, the invention is directed to a method of utilizing a sensor to detect and/or monitor the presence of and/or concentration of one or more analytes (e.g., pathogens or other bioanalytes) in a sample, the method comprising: administering and/or contacting the suspension and/or the polymer to/with the sample; following the administering and/or contacting step, allowing one or more components of the administered and/or contacted suspension and/or polymer to accumulate in the sample, wherein the one or more components exhibit a detectable sensitivity to the one or more analytes to be assayed; and following the accumulation, obtaining a measurement (e.g., a 1D, 2D, or 3D measurement, map, or image (e.g., positron emission tomography (PET) or single-photon emission computed tomography (SPECT) image)) indicative of the presence and/or concentration of the one or more analytes in the sample.

In certain embodiments, the sample is a biological sample, and the one or more analytes is/are bioanalyte(s).

In certain embodiments, the method comprises allowing the one or more components of the administered and/or contacted suspension and/or polymer to accumulate in an extracellular location of the biological sample.

In certain embodiments, the method comprises allowing the one or more components of the administered/contacted suspension and/or polymer to accumulate in an intracellular location (e.g., in cellular nuclei and/or in the cytosol) of the biological sample.

In certain embodiments, the biological sample is an in vitro, ex vivo, or in vivo sample (e.g., wherein the biological sample is a subject).

In certain embodiments, the administering and/or contacting step comprises administering and/or contacting a device (e.g., a chip, microneedle delivery device, or transdermal patch) comprising the suspension and/or the polymer to/with the sample (e.g., wherein contacting comprises embedding, adhering, injecting, or placing the device into or onto the sample).

In certain embodiments, the functional side chains of the helical polymer comprise a radiolabel, and wherein the measurement is a measurement of radiation emitted by the radiolabel. In certain embodiments, functional side chains comprise a complex of 1,4,7,10-tetraazacyclododecane-1,4,7,10-tetraacetic acid (DOTA) with a metallic lanthanide (e.g., yttrium or lutetium).

In another aspect, the invention is directed to a method of utilizing a sensor to detect and/or monitor a redox potential in a sample, the method comprising: administering and/or contacting the suspension of any one of claims 1 to 14 to/with the sample; optionally, following the administering and/or contacting step, allowing one or more components of the administered and/or contacted suspension to accumulate in the sample (e.g., further comprising, absorbing a quantity of the sample into a test strip or isolating a quantity of the sample for redox measurement; e.g., further comprising, contacting the isolated sample with the suspension, rather than the one or more components of the suspension moving into the sample); and exposing the one or more components of the administered and/or contacted suspension to an applied voltage, and measuring the resulting redox potential (e.g., a 1D, 2D, or 3D measurement or map) of the sample.

In certain embodiments, the sample is a biological sample, and the measured reduction potential is in the range from −150 millivolts to −400 millivolts.

In certain embodiments, the method further comprises allowing the one or more components of the administered/contacted suspension to accumulate in an extracellular location of the biological sample.

In certain embodiments, the method further comprises allowing the one or more components of the administered/contacted suspension to accumulate in an intracellular location (e.g., a cellular nuclei and/or a cytosol) of the biological sample.

In certain embodiments, the functional side chains of the helical polymer comprise an organelle targeting group.

In certain embodiments, the biological sample is an in vitro, ex vivo, or in vivo sample.

In certain embodiments, the administering and/or contacting step comprises administering or contacting a device (e.g., a chip, microneedle delivery device, or transdermal patch) comprising the suspension to/with the sample (e.g., wherein contacting comprises embedding, adhering, injecting, or placing the device into or onto the sample).

In certain embodiments, the biological sample is skin and wherein the one or more components of the administered and/or contacted suspension are delivered to and embedded within an epidermal layer of the skin (e.g., further comprising monitoring an extracellular redox potential over time).

In another aspect, the invention is directed to a kit for use in a radiopharmacy setting, the kit comprising: at least one container, wherein the container has a type selected from an ampule, a vial, a cartridge, a reservoir, a lyo-ject, or a pre-filled syringe; the polymer, wherein the molecular weight (e.g., weight average molecular weight or number average molecular weight) is from 5 kDa to 75 kDa (e.g., from 10 kDa to 50 kD, e.g., from 15 kDa to 30 kDa); at least one disposable size exclusion column; and at least one disposable filter, wherein the at least one container holds (e.g., contains) the polymer.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Analyte": As used herein, the term "analyte" broadly refers to any substance to be analyzed, detected, measured, or quantified. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Detector": As used herein, the term "detector" includes any detector of electromagnetic radiation including, but not limited to, CCD cameras, photodiodes, optical sensors, and infrared detectors.

"Functionalization": As used herein, the term "functionalization" refers to any process of modifying a material by bringing physical, chemical or biological characteristics different from the ones originally found on the material. Typically, functionalization involves introducing functional groups to the material. As used herein, functional groups are specific groups of atoms within molecules that are responsible for the characteristic chemical reactions of those molecules. As used herein, functional groups include both chemical (e.g., ester, carboxylate, alkyl) and biological groups (e.g., adapter, or linker sequences).

In some embodiments, click reactive groups are used (for 'click chemistry'). Examples of click reactive groups include the following: alkyne, azide, thiol (sulfydryl), alkene, acrylate, oxime, maliemide, NHS (N-hydroxysuccinimide), amine (primary amine, secondary amine, tertiary amine, and/or quarternary ammonium), phenyl, benzyl, hydroxyl, carbonyl, aldehyde, carbonate, carboxylate, carboxyl, ester, methoxy, hydroperoxy, peroxy, ether, hemiacetal, hemiketal, acetal, ketal, orthoester, orthocarbonate ester, amide, carboxyamide, imine (primary ketimine, secondary ketamine, primary aldimine, secondary aldimine), imide, azo (diimide), cyanate (cyanate or isocyanate), nitrate, nitrile, isonitrile, nitrite (nitrosooxy group), nitro, nitroso, pyridyl, sulfide, disulfide, sulfinyl, sulfonyl, sulfino, sulfo, thiocyanate, isothiocyanate, caronothioyl, thione, thial, phosphine, phosphono, phosphate, phosphodiester, borono, boronate, bornino, borinate, halo, fluoro, chloro, bromo, and/or iodo moieties.

"Image": The term "image", as used herein, is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). The term "image" may refer, for example, to an optical image, an x-ray image, an image generated by: positron emission tomography (PET), magnetic resonance, (MR) single photon emission computed tomography (SPECT), and/or ultrasound, and any combination of these.

"Radiolabel": As used herein, "radiolabel" refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT). In some embodiments, radioisotopes comprise $^{99m}Tc$, $^{111}In$, $^{64}Cu$, $^{67}Ga$, $^{186}Re$, $^{188}Re$, $^{153}Sm$, $^{177}Lu$, $^{67}Cu$, $^{123}I$, $^{124}I$, $^{125}I$, $^{11}C$, $^{13}N$, $^{15}O$, $^{18}F$, $^{186}Re$, $^{188}Re$, $^{153}Sm$, $^{166}Ho$, $^{177}Lu$, $^{149}Pm$, $^{90}Y$, $^{213}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, $^{89}Zr$, $^{225}Ac$, and $^{192}Ir$.

"Sample": The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conjunction with the accompanying drawings, in which:

FIG. 1A shows synthesis of polycarbodiimide polymers (Poly-1-8).

FIG. 1B depicts an exemplary scheme showing preparation of the polycarbodiimide-SWCNT aqueous suspension.

FIG. 2A shows vis-nIR absorption spectra.

FIG. 2B shows nIR emission spectra of polycarbodiimide-SWCNTs (16 mg/L nanotubes) excited at 659 nm.

FIG. 2C shows center wavelengths of nanotube emission peaks collected from photoluminescence excitation/emission profiles of polycarbodiimide-SWCNTs and surfactant suspended SWCNTs.

FIG. 2D shows atomic force micrograph of Amine-Poly-8-SWCNT complexes showing periodic banding along the nanotube surface.

FIG. 2E shows a magnified AFM image of a single Amine-Poly-8-SWCNT complex.

FIG. 2F shows a height profile of a single complex denoted by the white arrow in FIG. 2E.

FIG. 4A shows atomic force microscopy height images of Amine-Poly-6-SWCNT.

FIG. 4B shows atomic force microscopy height images of Amine-Poly-8-SWCNTs.

FIG. 4C shows atomic force microscopy height images of transmission electron microscopy images of polycarbodiimide-SWCNTs.

FIG. 5A shows a schematic representation of the INFRET process and its reversal upon addition of amine-functionalized polycarbodiimide.

FIG. 5B shows photoluminescence excitation-emission (PLE) map of Amine-Poly-6-SWCNTs, Carboxy-Poly-7-SWCNTs, mixture of Amine-Poly-6-SWCNTs and Carboxy-Poly-7-SWCNTs, and the mixture after subsequent addition of amine-polymer.

FIG. 5C shows a nanotube (n, m) species-dependent PL intensity change upon initiating INFRET.

FIG. 5D shows a nanotube (n, m) species-dependent PL intensity change upon INFRET reversal.

FIG. 5E shows individual spectra acquired during a time course acquisition of INFRET kinetic data. Intensity was normalized to the area under the curve.

FIG. 5F shows INFRET dynamics show a monotonic relative PL intensity increase in small bandgap nanotubes (Peaks 4 and 5) and simultaneous relative PL intensity decrease in large bandgap nanotubes (Peaks 1-3).

FIG. 5G shows INFRET ratio, plotted using Peak 5 as the acceptor and Peak 1 as the donor. The final data point was acquired after initiating INFRET reversal using amine-polymer.

to obtain the parameters in the accompanying table.

Figure 7A:
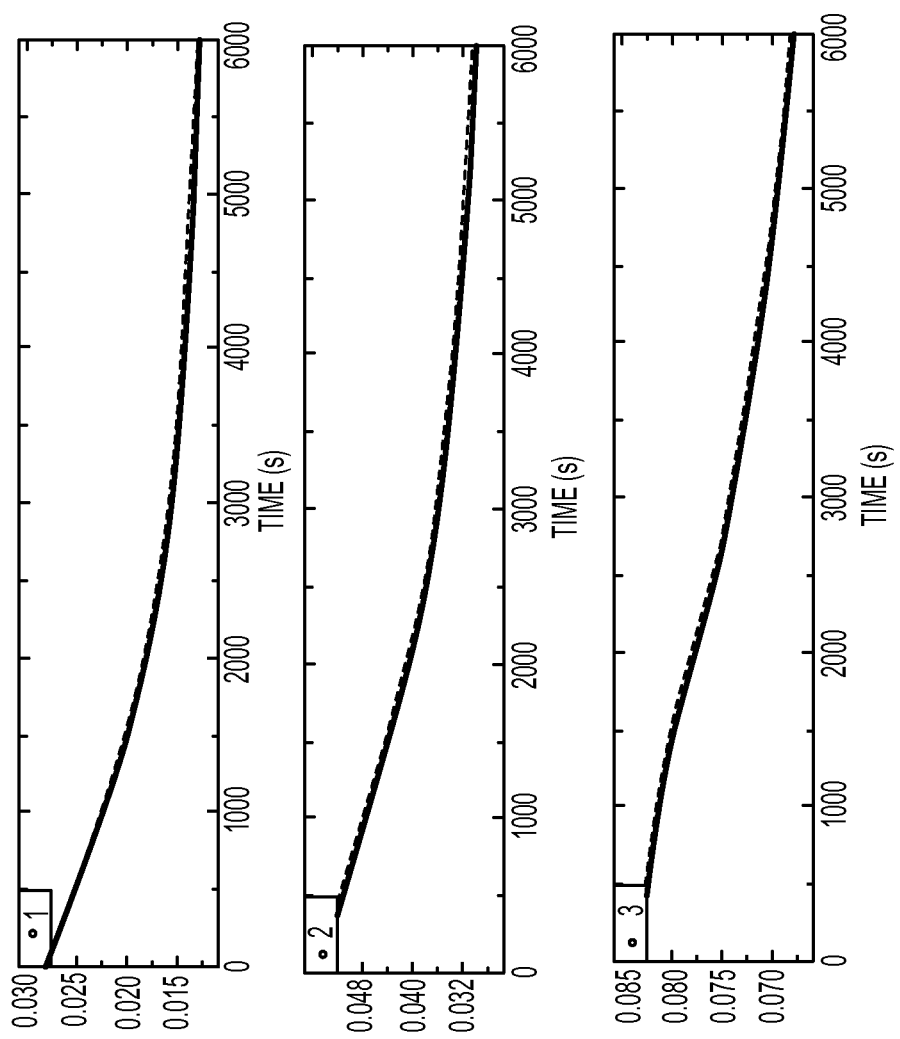
FIGS. 7A and 7A-1 show that the kinetic data from FIG. 5F was fit with a logistic function (of the form $$y = \frac{A1 - A2}{1 + \left(\frac{x}{x0}\right)p} + A2$$
Figures 1, 7A:
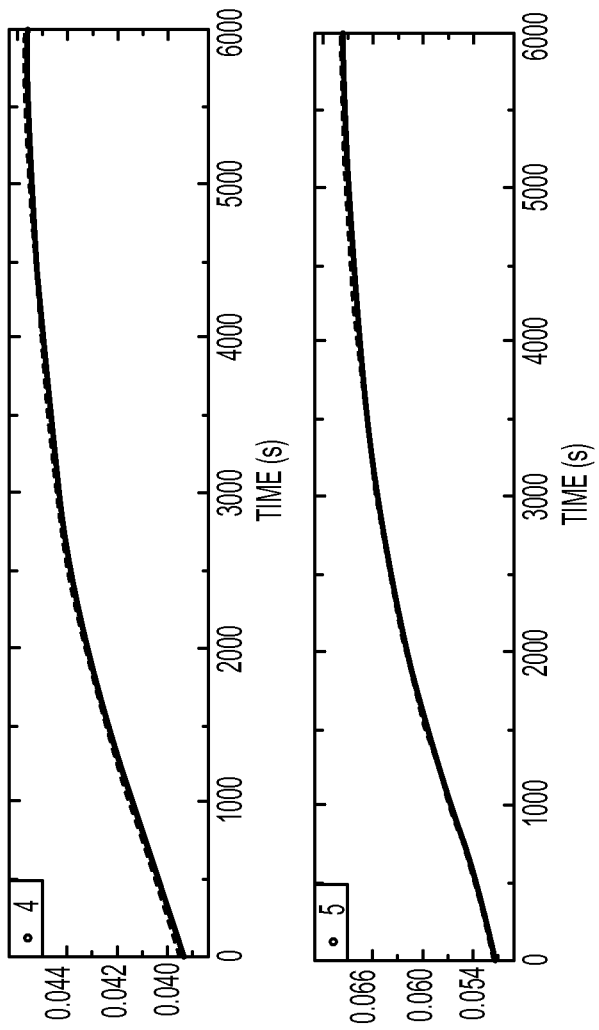
Figure 7B:
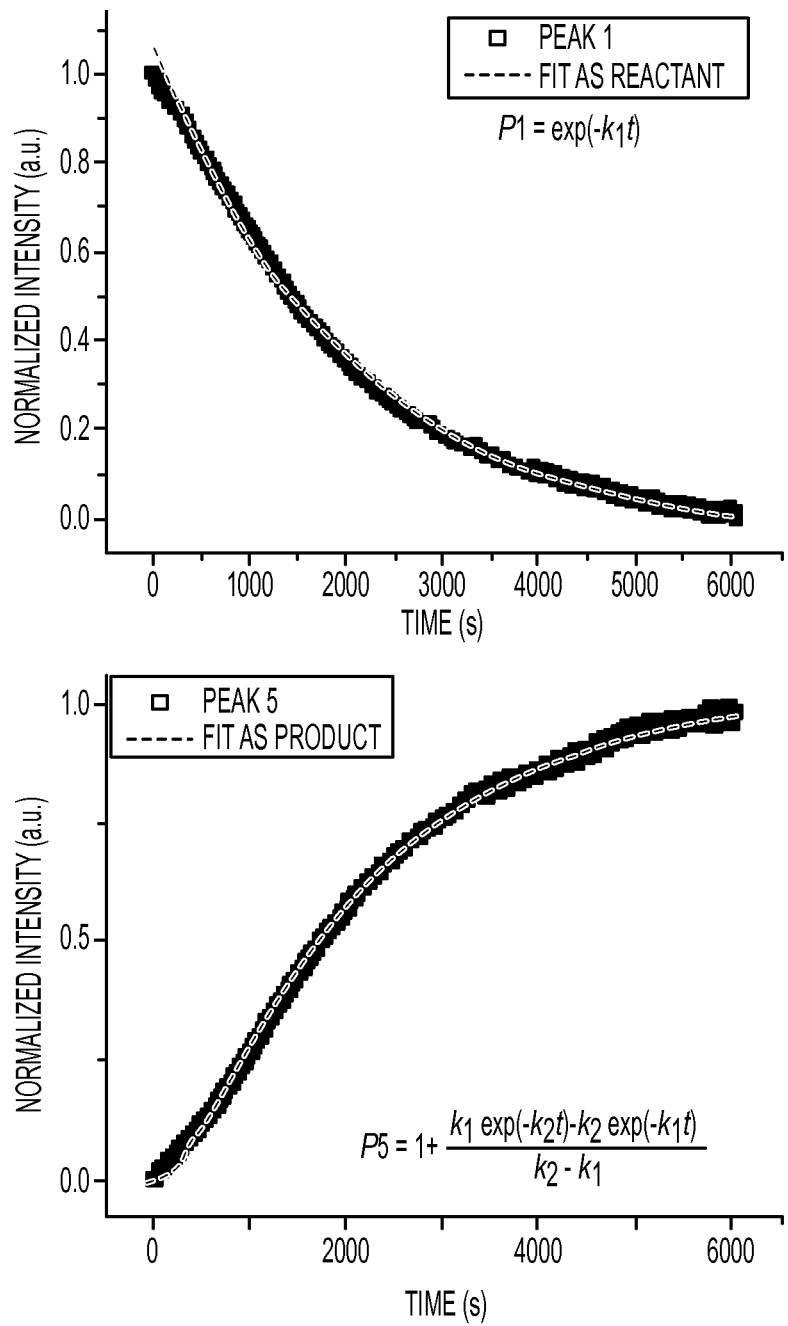

FIG. 7B shows the curves of peaks P1 and P5 fit the classical solutions for the reactant and product, respectively, in a consecutive series of first order chemical reactions.

Figure 8A:
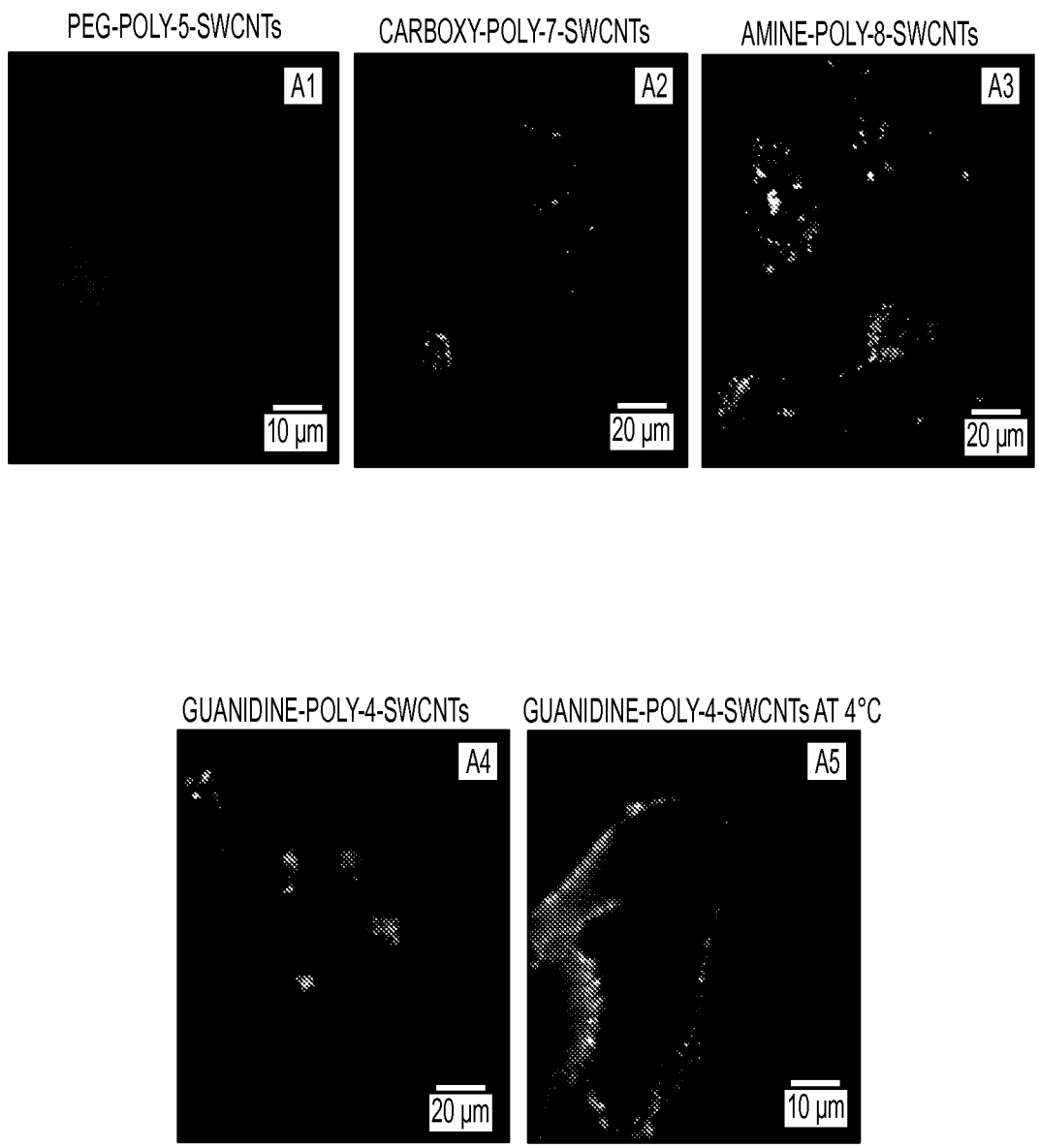
Figure 8B:
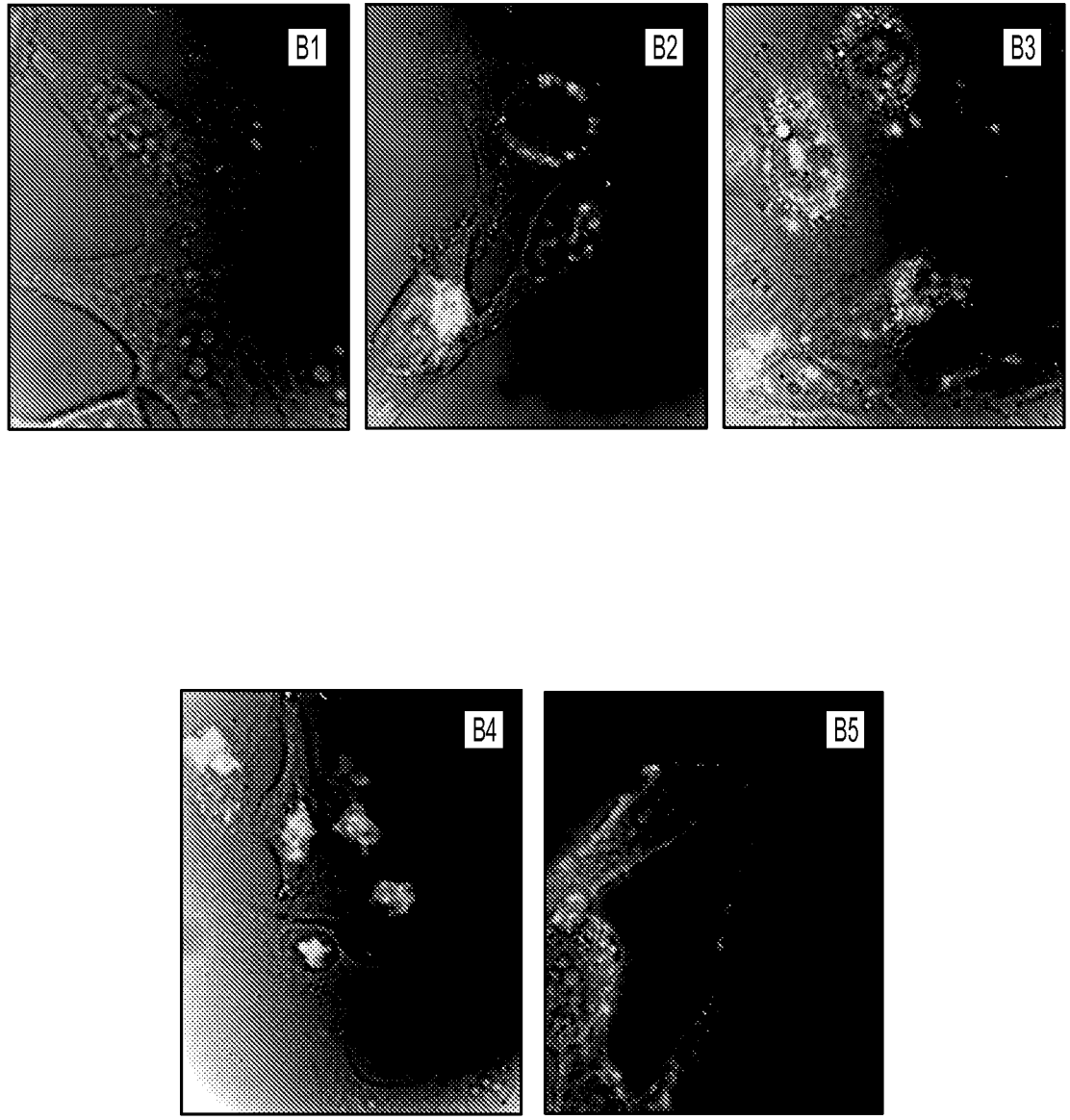
Figure 8C:
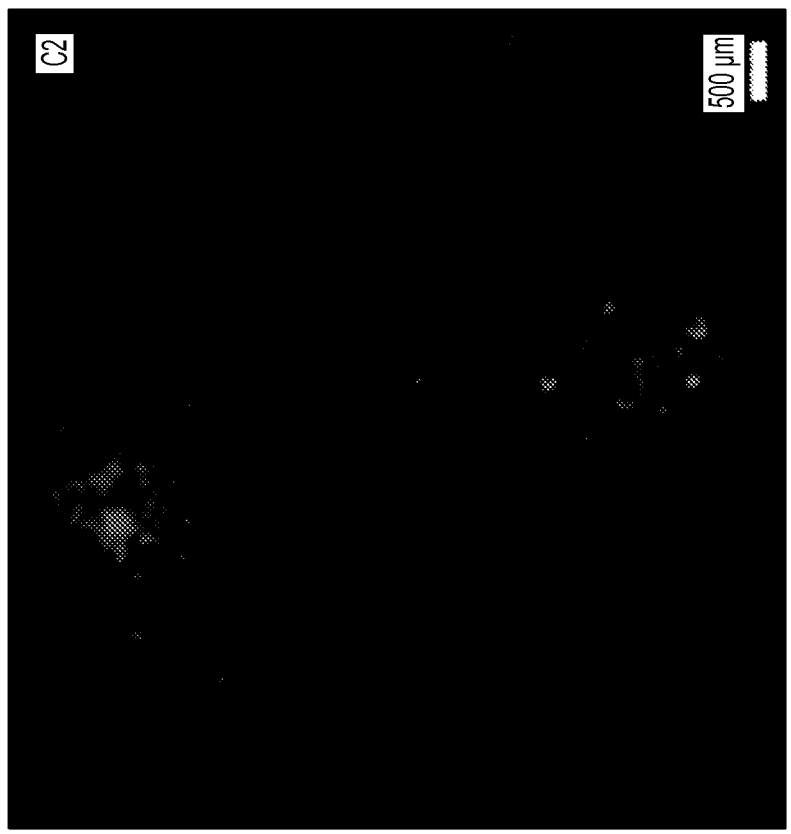
Figure 8C:
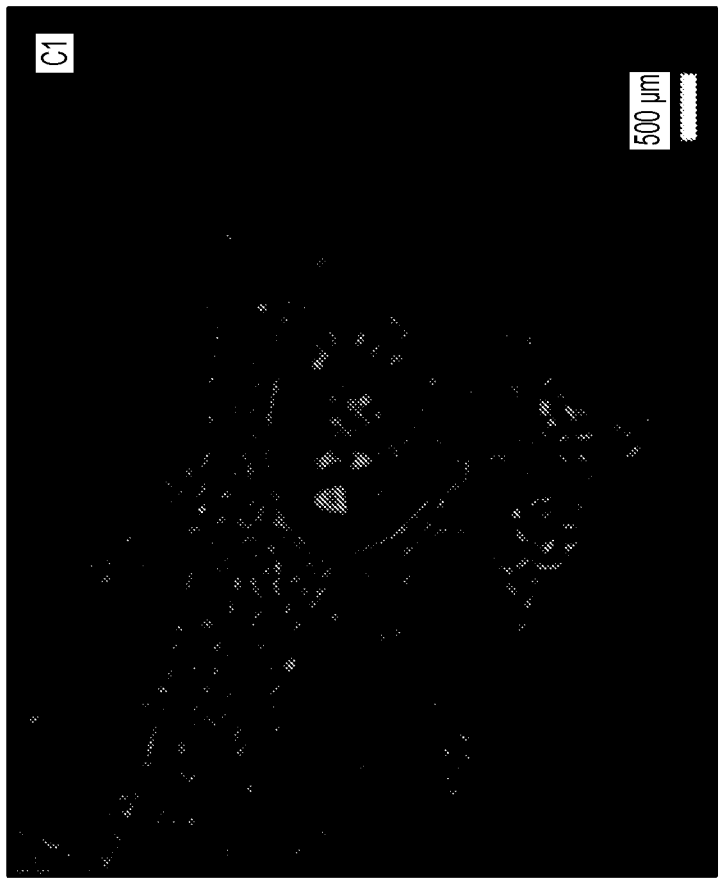

FIGS. 8A-8C show near infrared (nIR) fluorescence images of living HeLa cells incubated with polycarbodiimide-SWCNTs.

FIG. 8A, comprising panels A1-A5, shows cells incubated with specified polymernanotube complexes at 37° C. for 18 h. Panel A5, for example, is a micrograph of cells incubated at 4° C. for 4 h. A 730 nm laser was used for excitation and light was collected over 900 nm-1400 nm.

FIG. 8B, comprising panels B1-B5, shows combined nIR fluorescence and brightfield images of living HeLa cells.

FIG. 8C, comprising-panels C1-C2, shows brightfield, nIR fluorescence and Hoechst nuclear stain of live HeLa cells incubated in the presence of Amine-Poly-8-SWCNTs and Guanidine-Poly-4-SWCNTs, respectively.

Figure 9A:
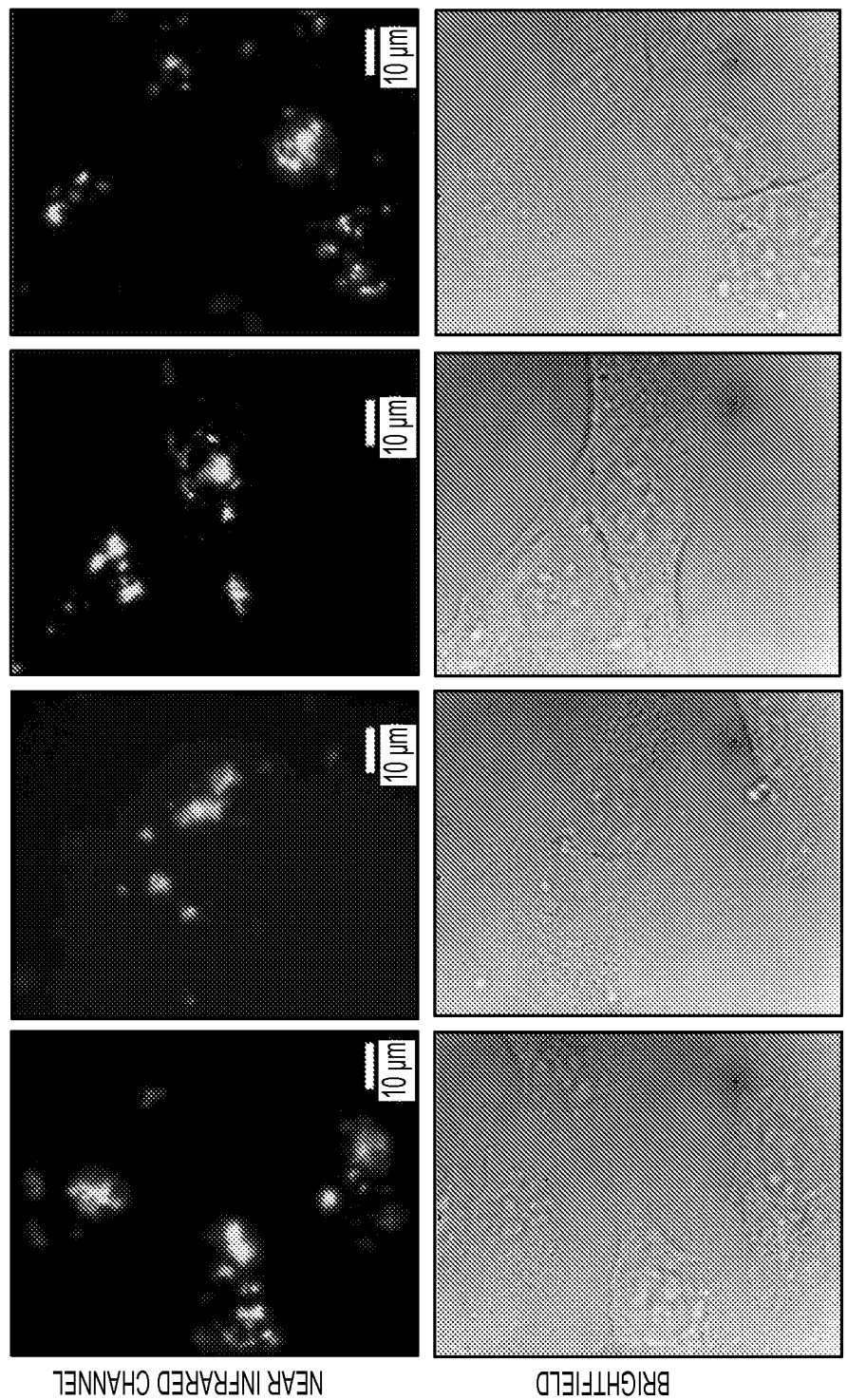
Figure 9B:
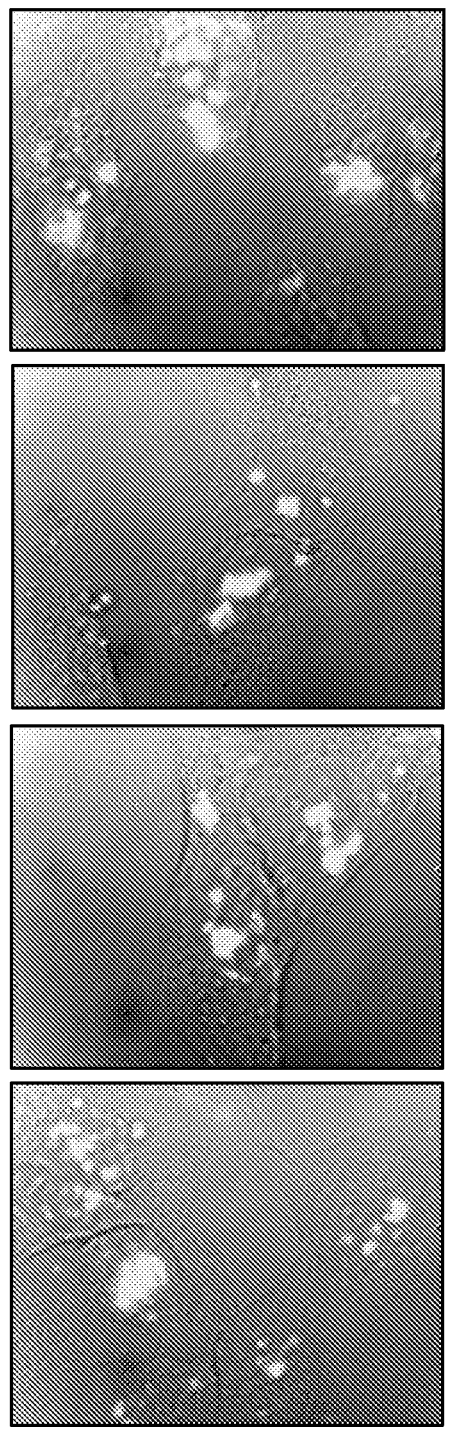

FIGS. 9A-9B show near-infrared fluorescence images of live HeLa cells incubated with Guanidine-Poly-4-SWCNTs. Near-infrared-bright-field overlays illustrate nuclear localization.

Figure 10:
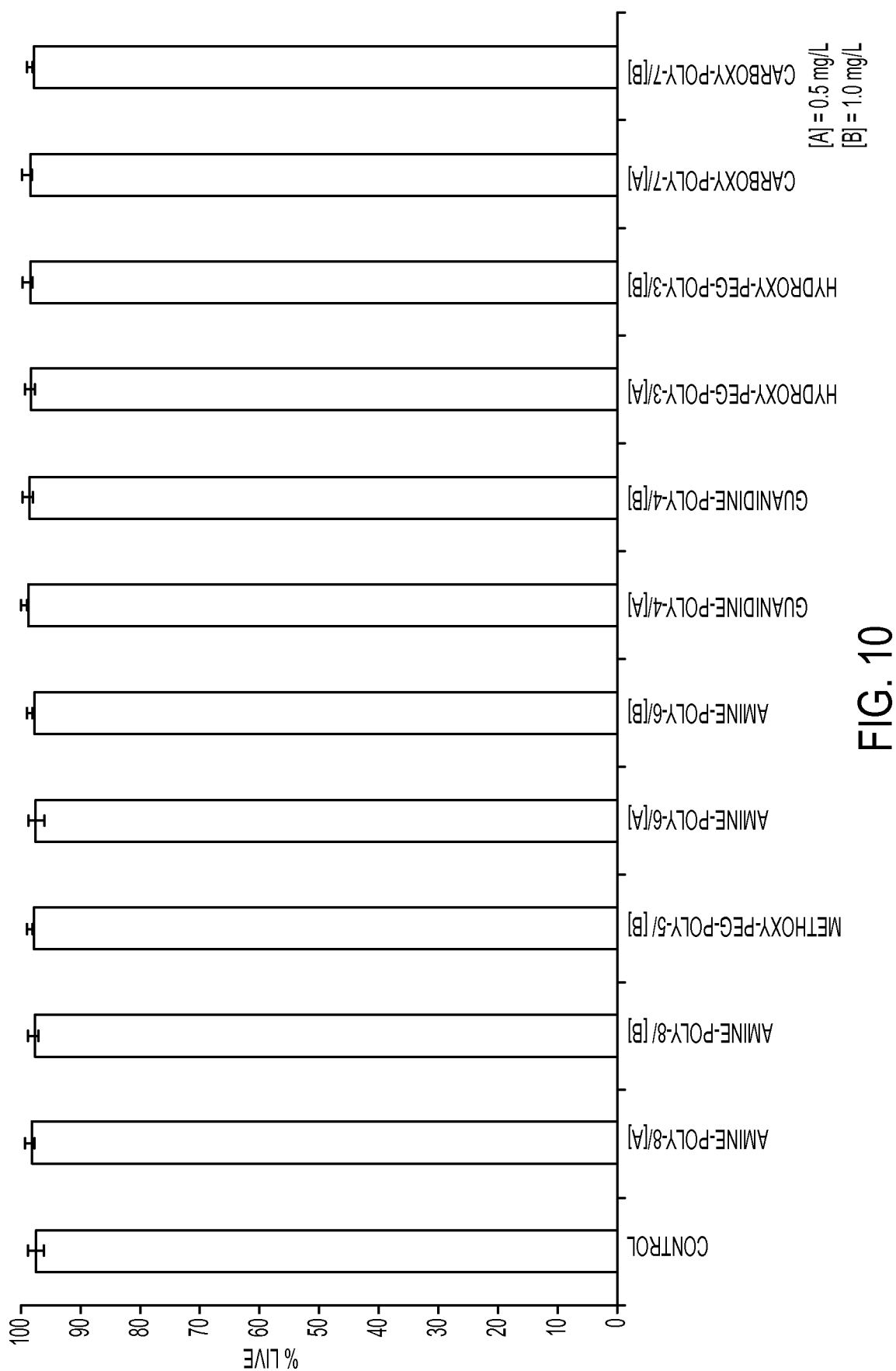

FIG. 10 shows viability assays on HeLa cells incubated with polycarbodiimide-SWCNT complexes. HeLa cells were incubated in the presence of specified polymer-nanotube complexes in a 35 mm petri dish for 24 hours before imaging. Tali™ Image-Based Cytometer was used to measure cell viability test performed using Tali™ viability kit-Dead cell red (Invitrogen) following manufacturer's protocol.

Figure 11:
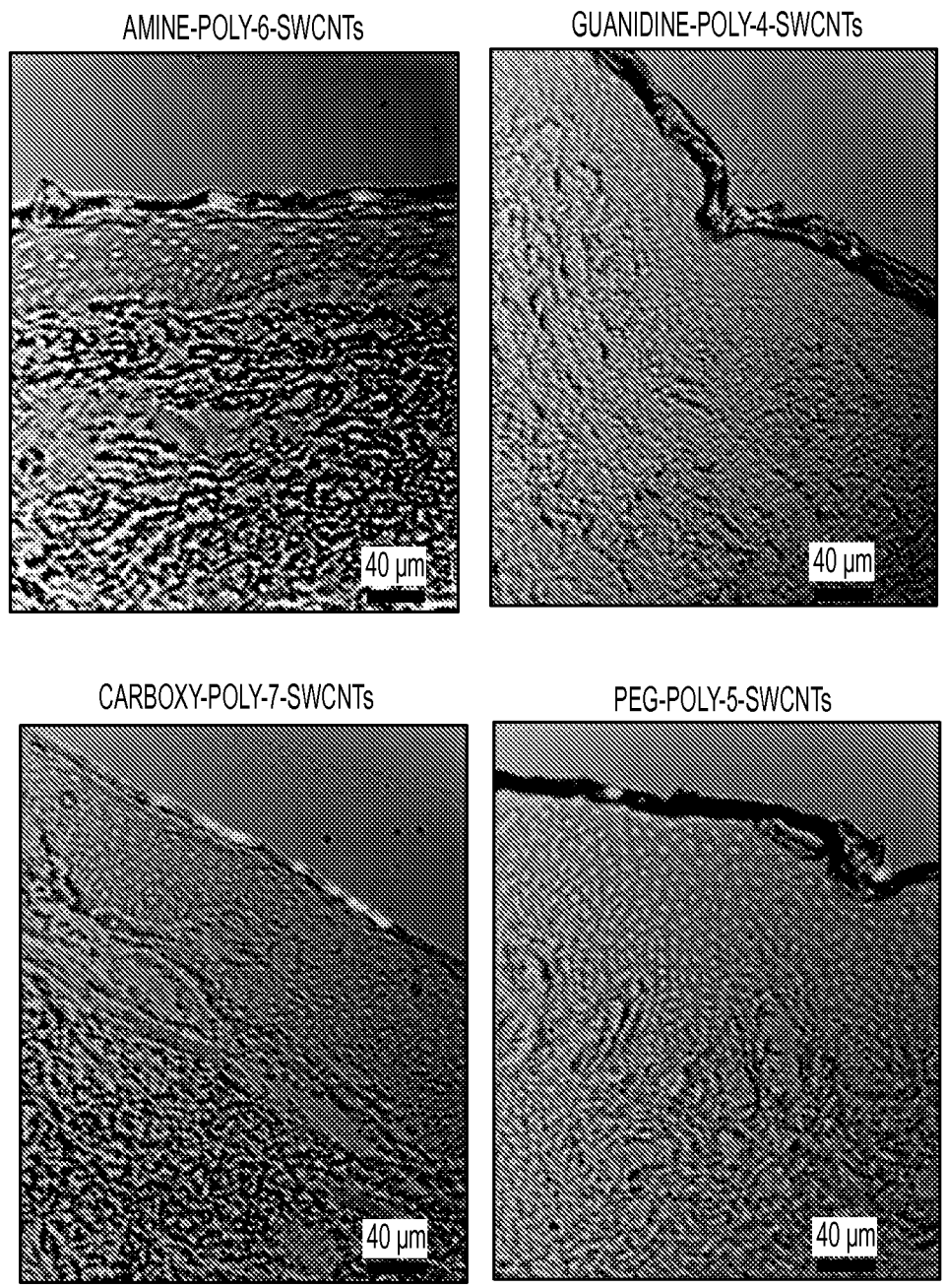

FIG. 11 shows near-infrared and brightfield overlay micrographs of human skin, showing the lack of penetration of polycarbodiimide-SWCNTs, regardless of functionalization. Polycarbodiimide-SWCNTs deposits mainly in the stratum corneum layer of the skin. Skin was acquired from human patients after Moh's surgery and immediately incubated with polycarbodiimide-SWCNTs on the surface of the skin specimen. Skin sections without nanotube treatment were used as control.

Figure 12A:
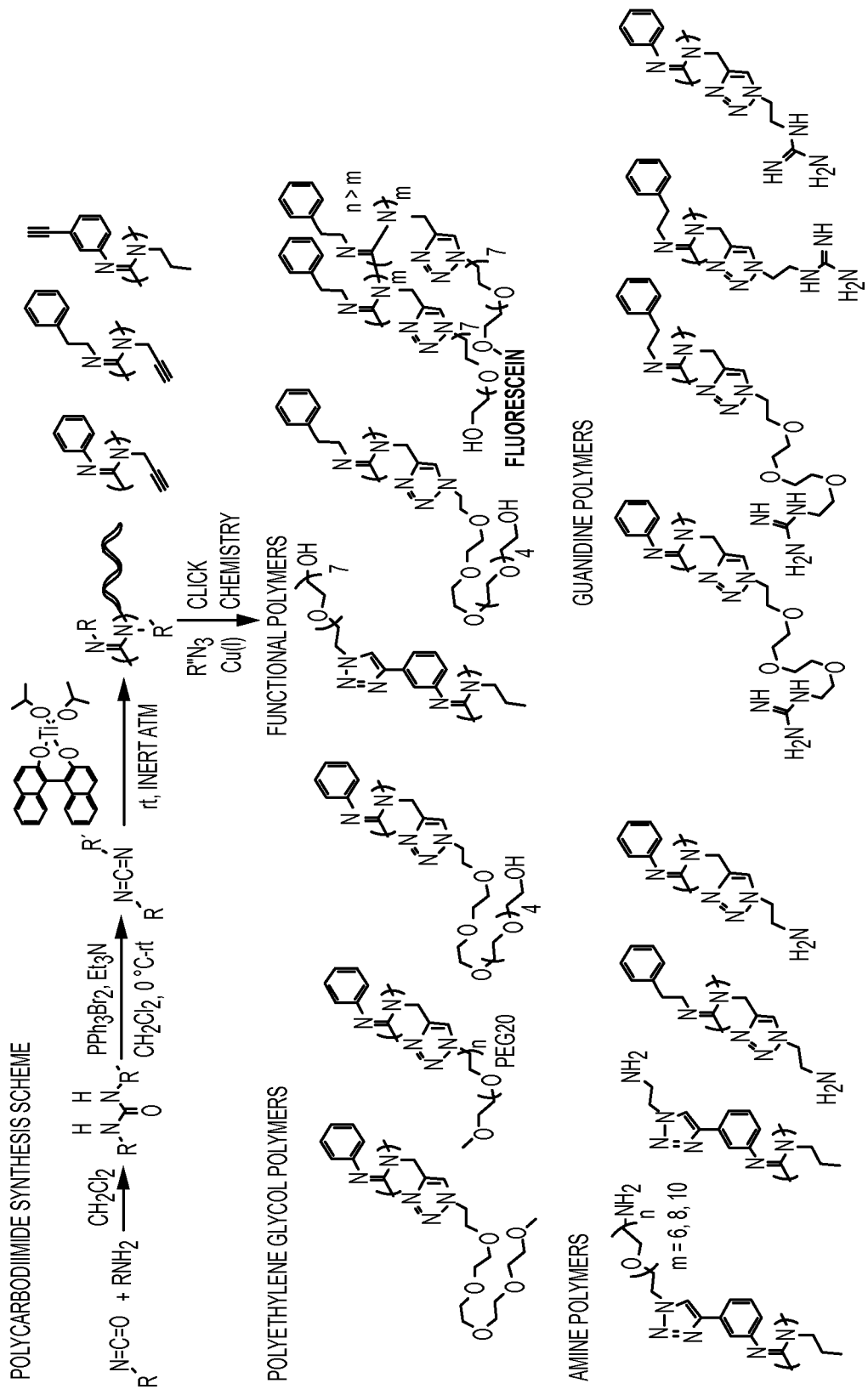
Figures 1, 12A:
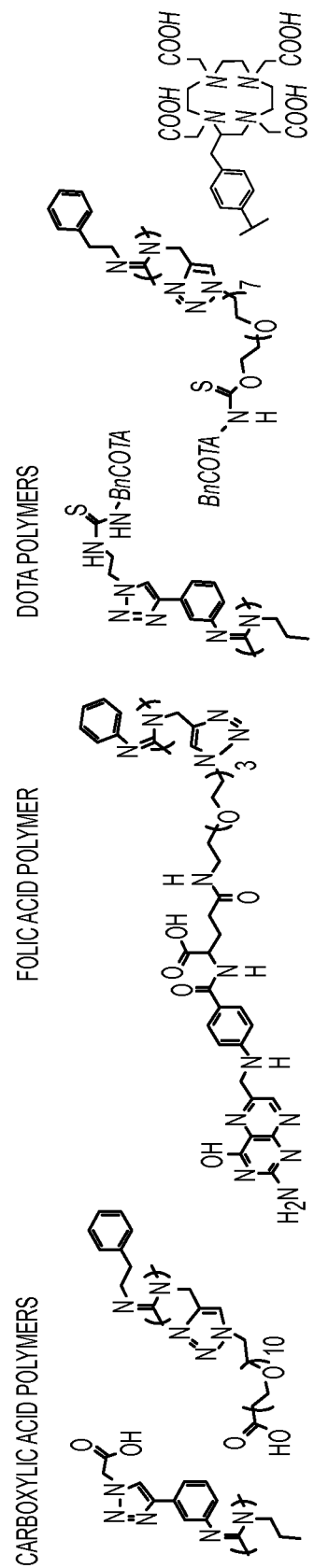
Figure 12B:
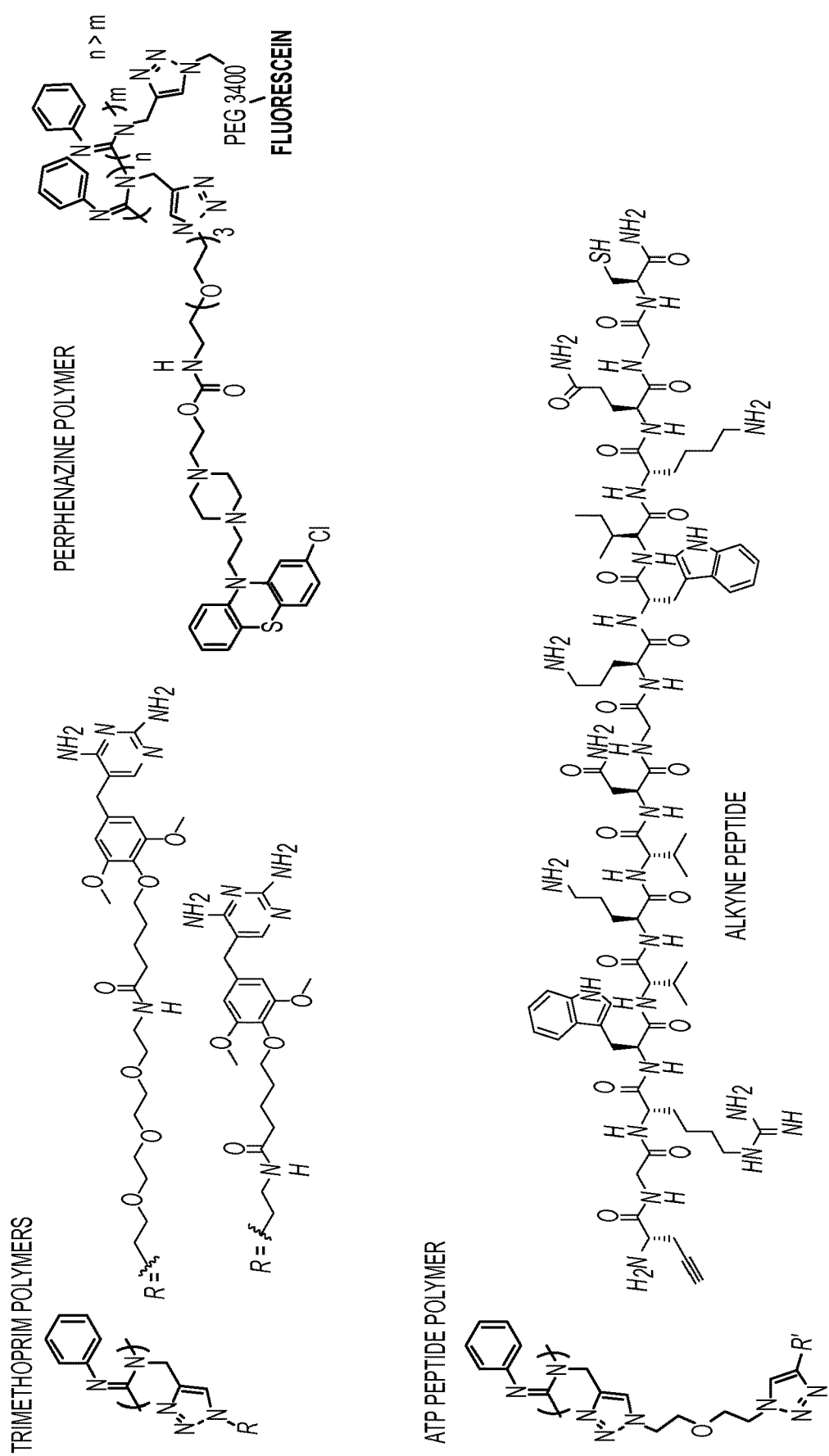
Figure 12C:
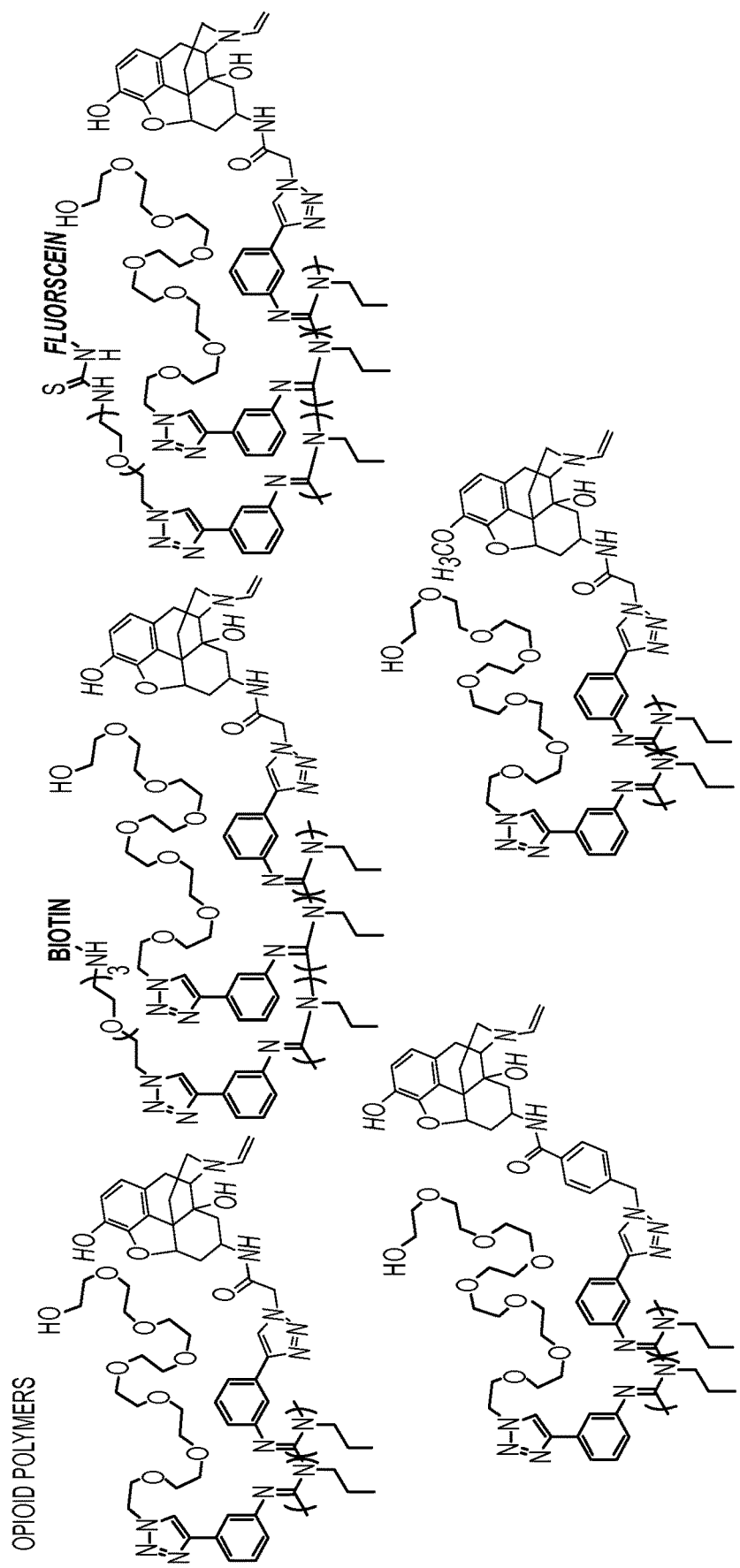

FIGS. 12A-12C show a synthesis scheme and molecular structures for helical polycarbodiimide polymers as described herein.

Figure 13A:
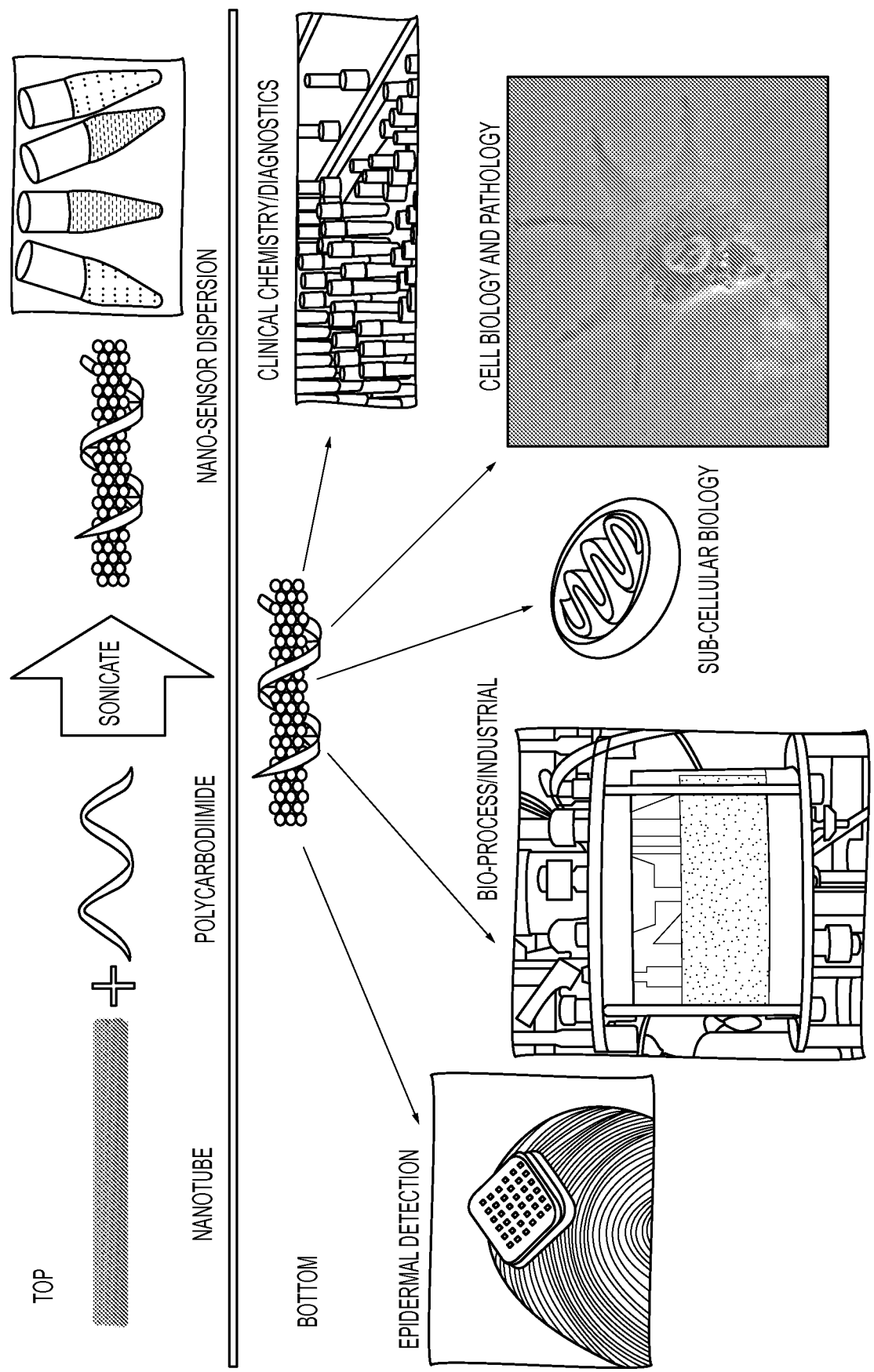
Figure 13B:
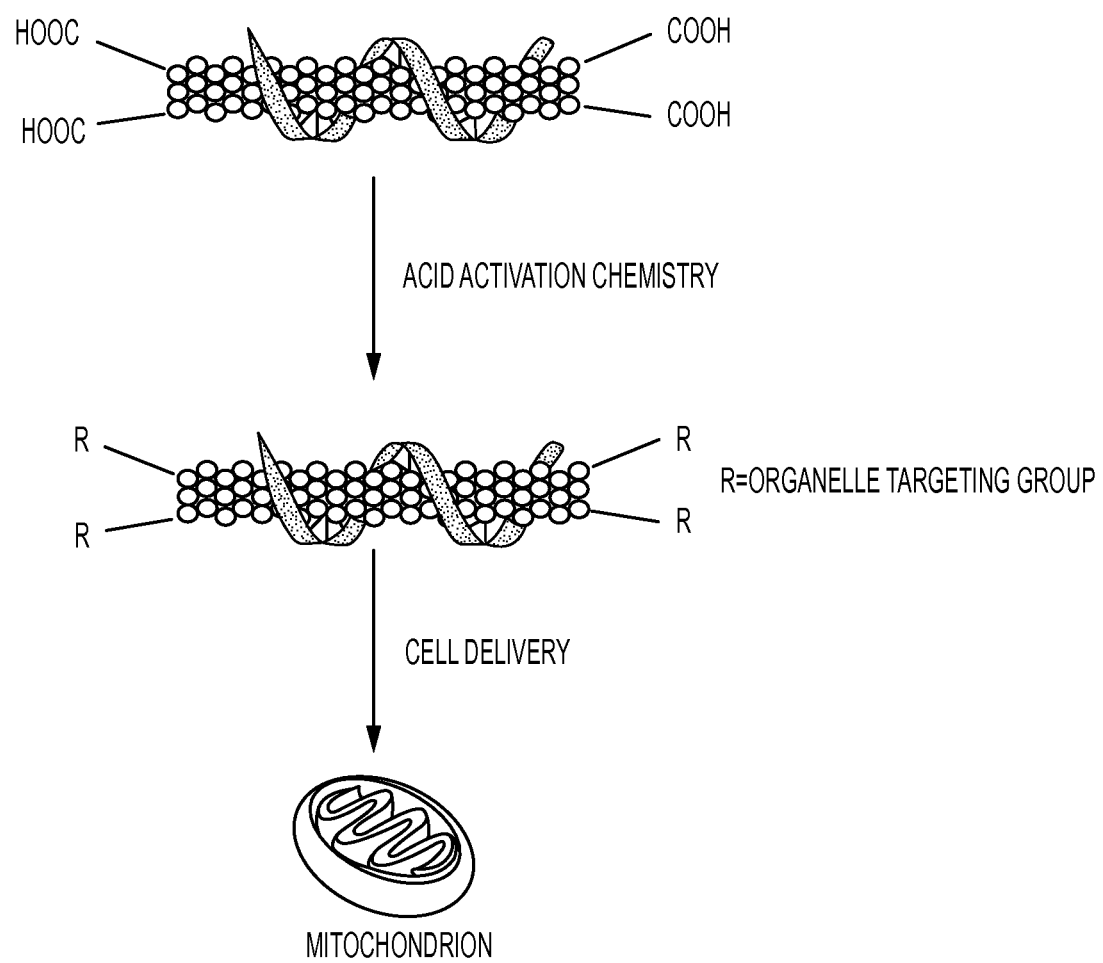

FIGS. 13A-13B depict schematics showing the manufacturing of a nano-sensor dispersion, according to an illustrative embodiment.

FIG. 13A shows representative scheme of sensor fabrication into final sensor dispersion (top) and examples of applications for the nano-sensor (bottom).

FIG. 13B shows example of sensor modification allowing specific targeting to sub-cellular locations.

Figure 14A:
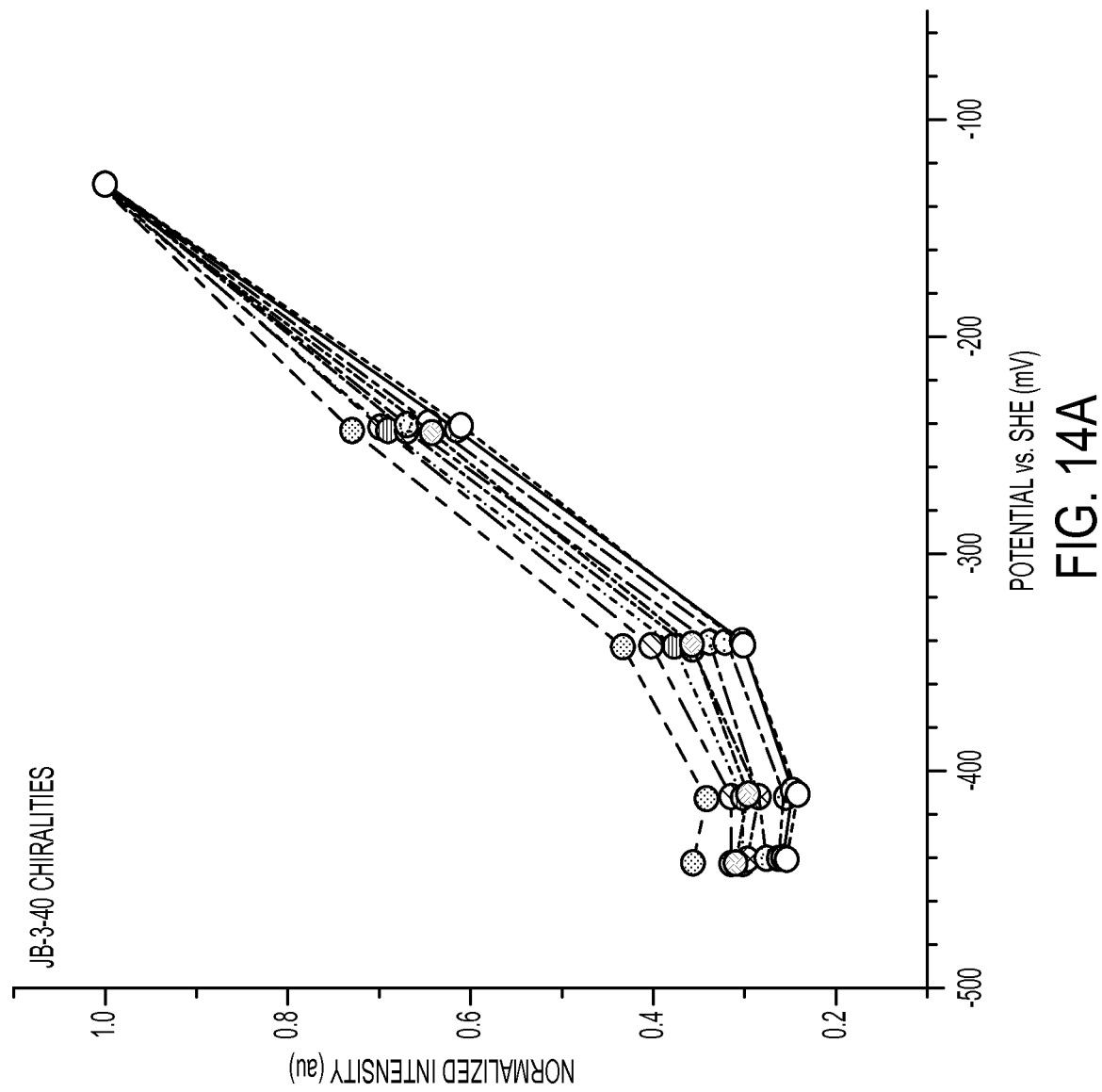
Figure 14B:
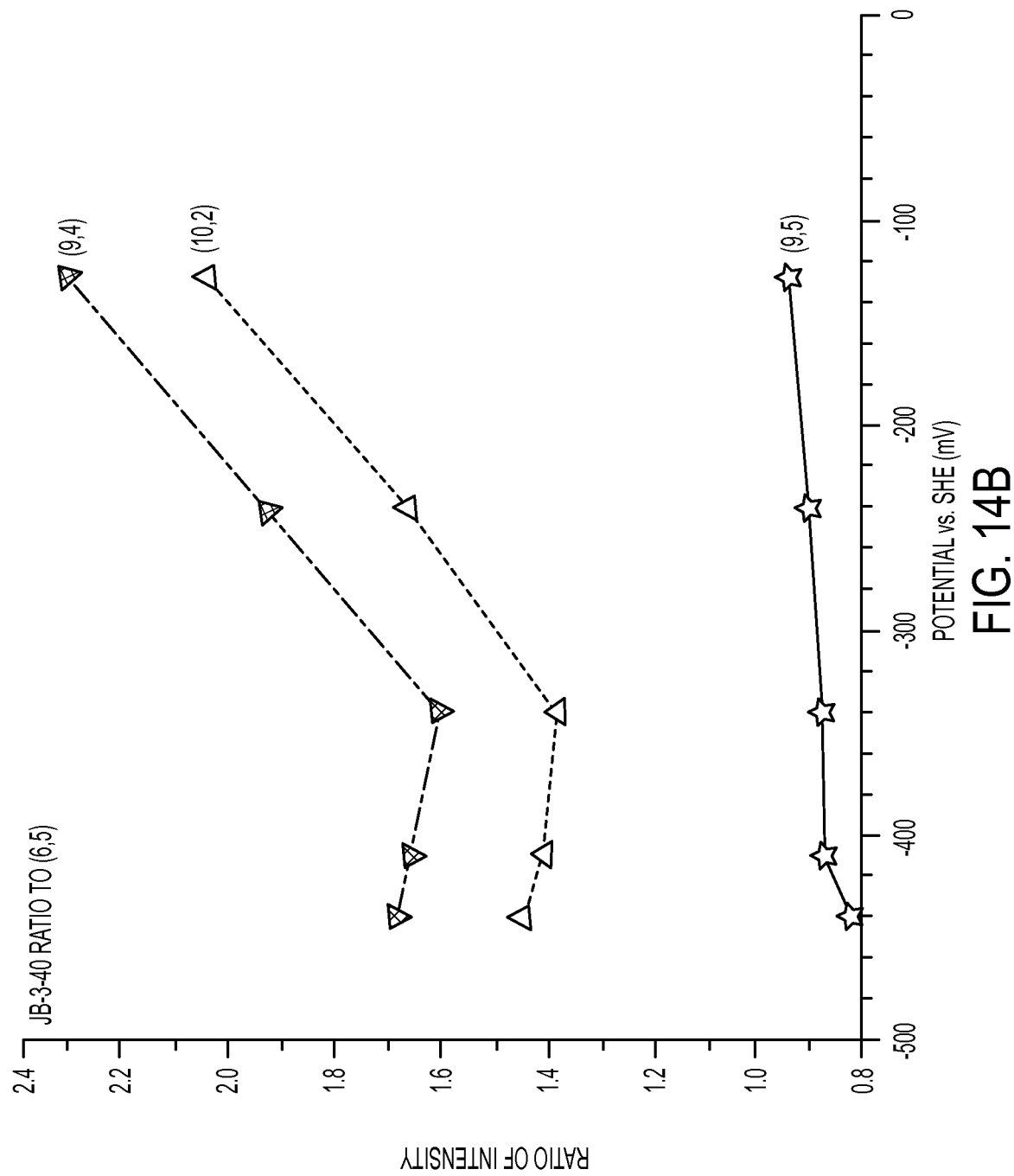

FIGS. 14A-14B show illustrative data from a nano-sensor dispersion.

FIG. 14A shows data showing the linear response of a nano-sensor to decreasing reduction potential mediated in a buffered aqueous biological solution of cysteine and ascorbate as major redox couples. Each marked line represents a unqiuely responding chiral nanotube within the same sensor population.

FIG. 14B shows data showing different chiralities of the sensor can act together to form a ratiometric fluorescence response, thereby allowing quantitative measurement.

Figure 15:
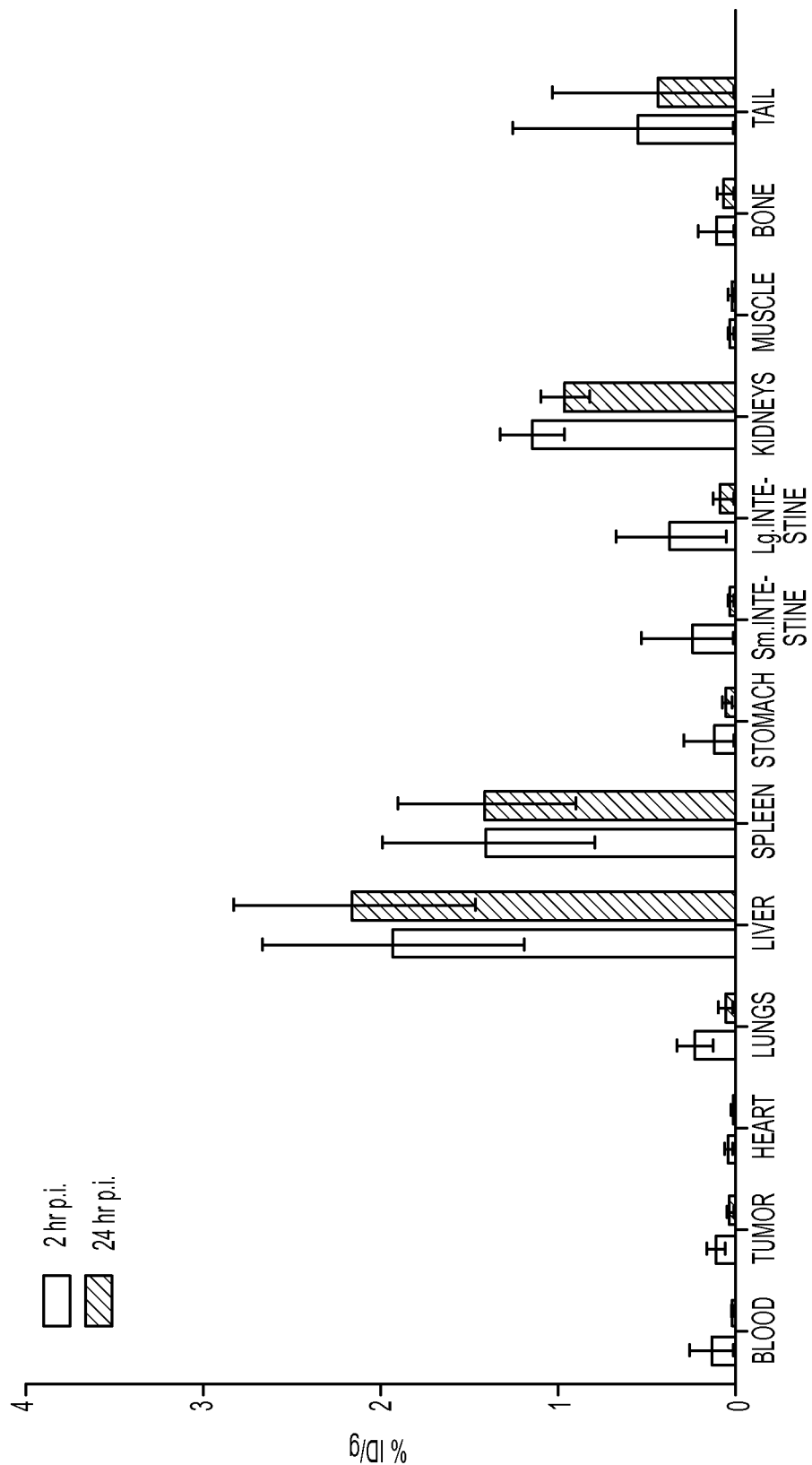

FIG. 15 shows the activities in liver, spleen, and kidney ranged from 1-2% ID/g suggesting that clearance from blood primarily occurred from the kidney, as typically hepatic/RES clearance is slow in comparison and shows high and prolonged uptake/retention in the liver and spleen (e.g. liposomes).

Figure 16:
Figure 16:
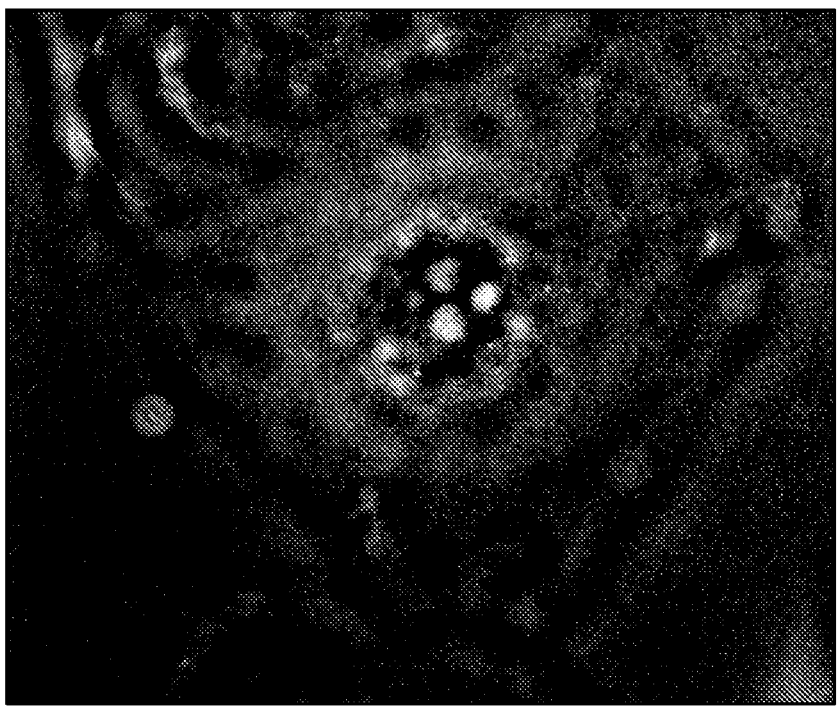

FIG. 16 shows representative images of polycarbodiimide polymers with opiate substituent groups.

Figure 17:
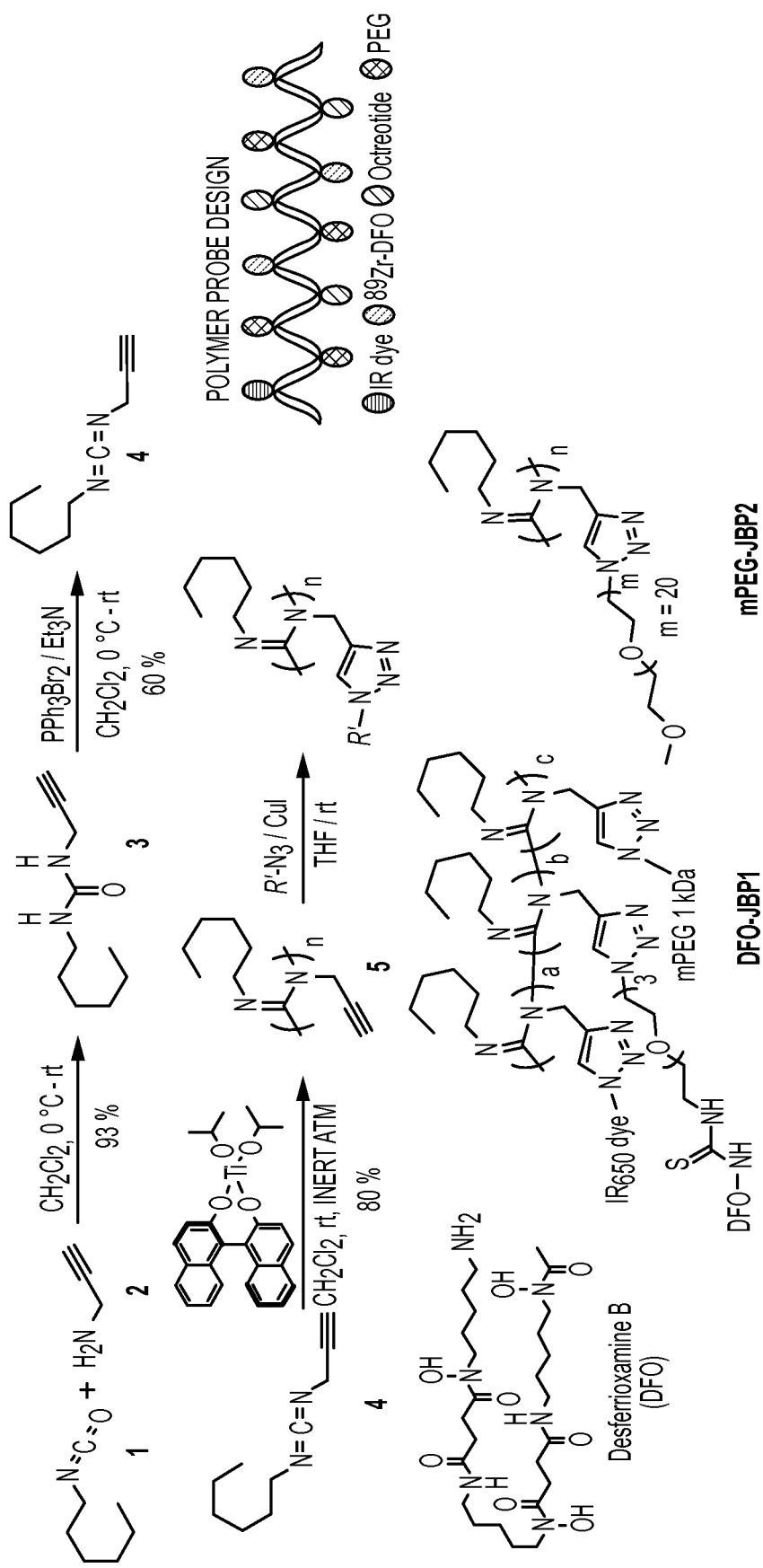

FIG. 17 shows synthesis of polymers: DFO-conjugated polymer DFO-JBP1 and polymer without DFO, mPEG-JBP2. DFO-JBP1 was synthesized to measure radiolabeling efficiency, in vitro stability, and in vivo performance of polycarbodiimide polymers without targeting ligands. mPEG-JBP2 serves as a negative control to ensure ligand specific binding of radiometal, 89Zr. Polymer probe design integrates targeting ligands, radiometal chelators, and solubilizing groups in a single polymer chain.

Figure 18A:
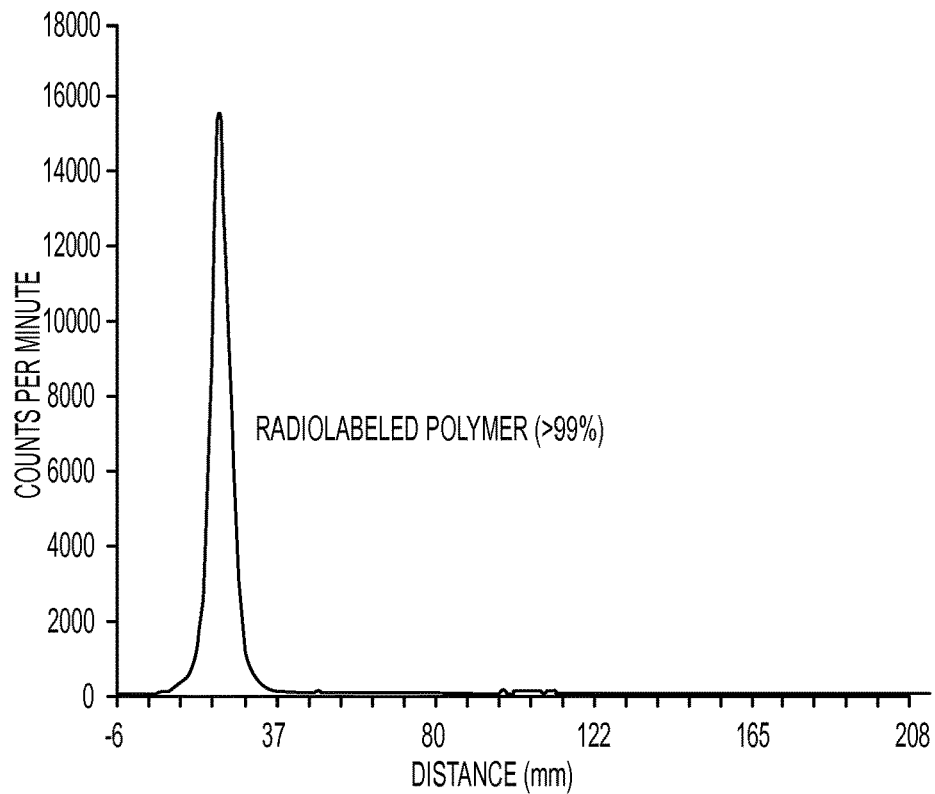
Figure 18B:
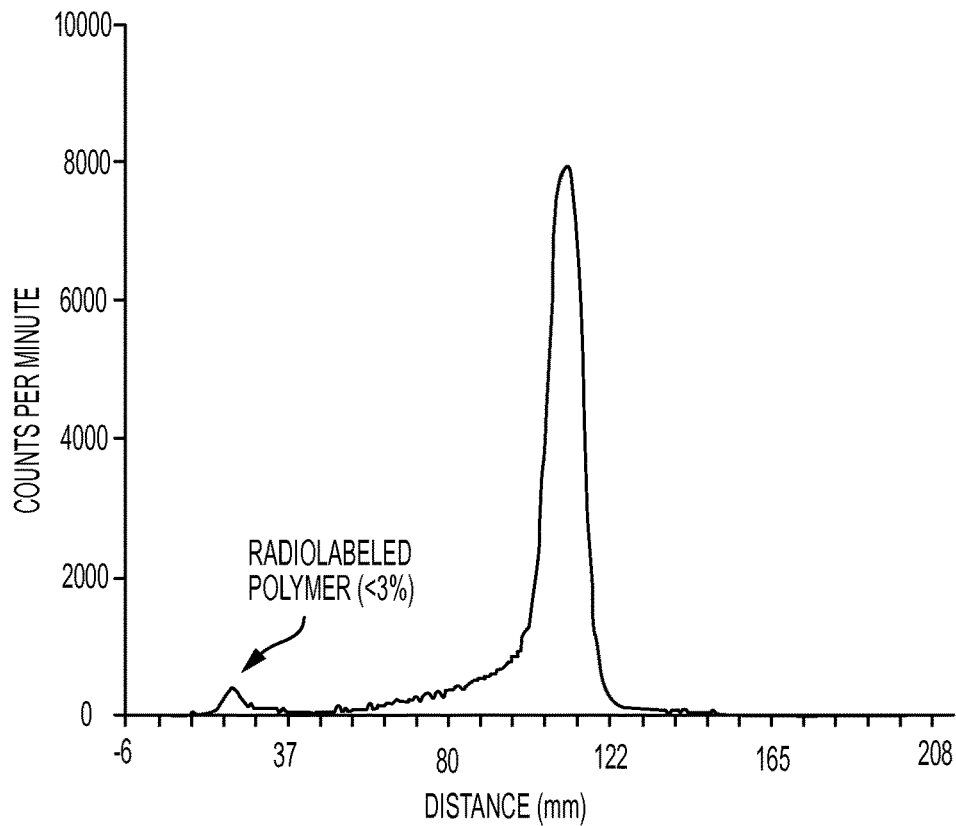
Figure 18C:
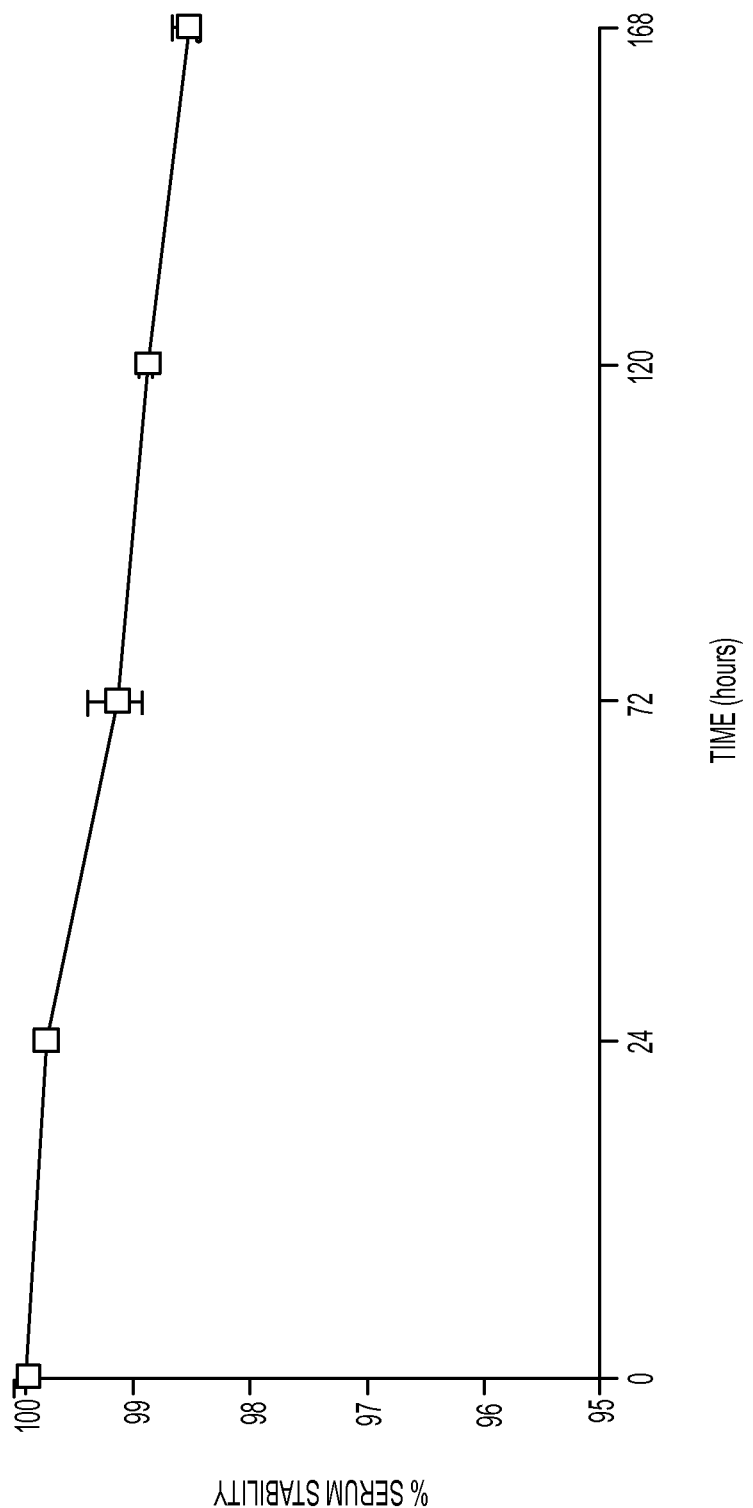

FIGS. 18A-18C shows radiolabeling of Polymers and Serum Stability Tests.

FIG. 18A show $^{89}$Zr labeling of DFO-JBP1 showed greater than 99% radiolabeling.

FIG. 18B depicts that a control polymer mPEG-JBP2 showed negligible labeling (less than 3%). Radiolabeling was performed at room temperature for 30 minutes.

FIG. 18C depicts that $^{89}$Zr-labeled polymer, or $^{89}$Zr-DFO-JBP1, showed 99% stability in human serum at 37° C. over seven days.

Figure 19A:
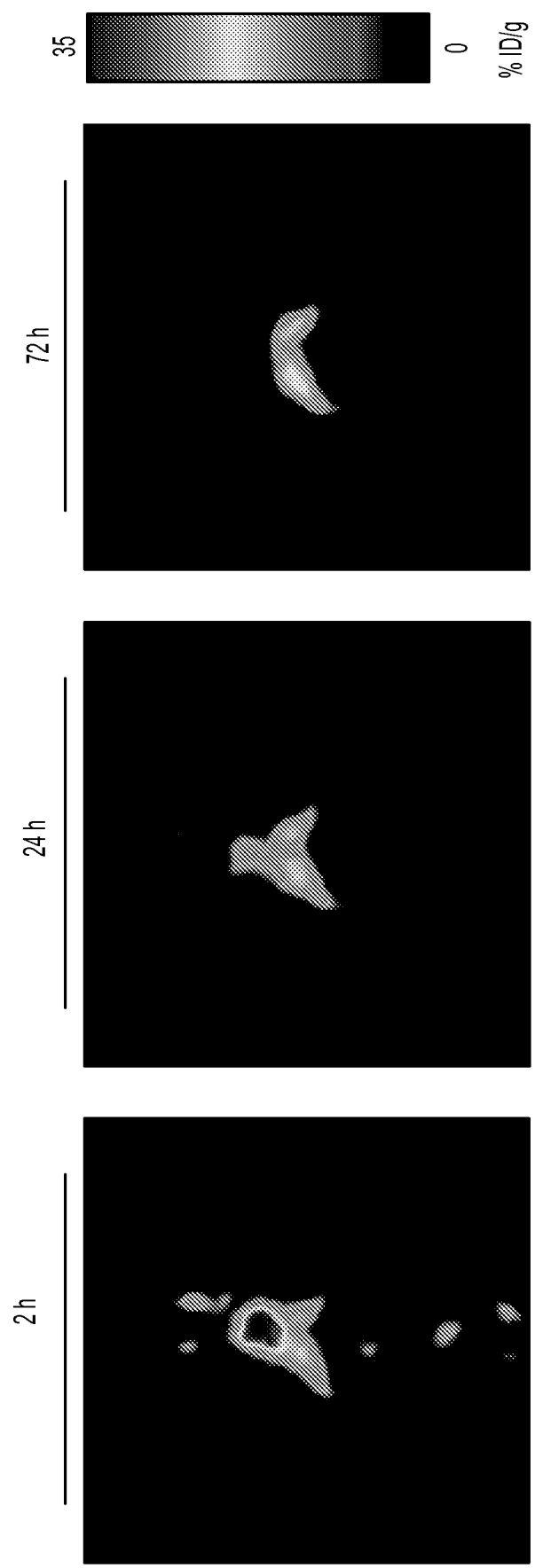
Figure 19B:
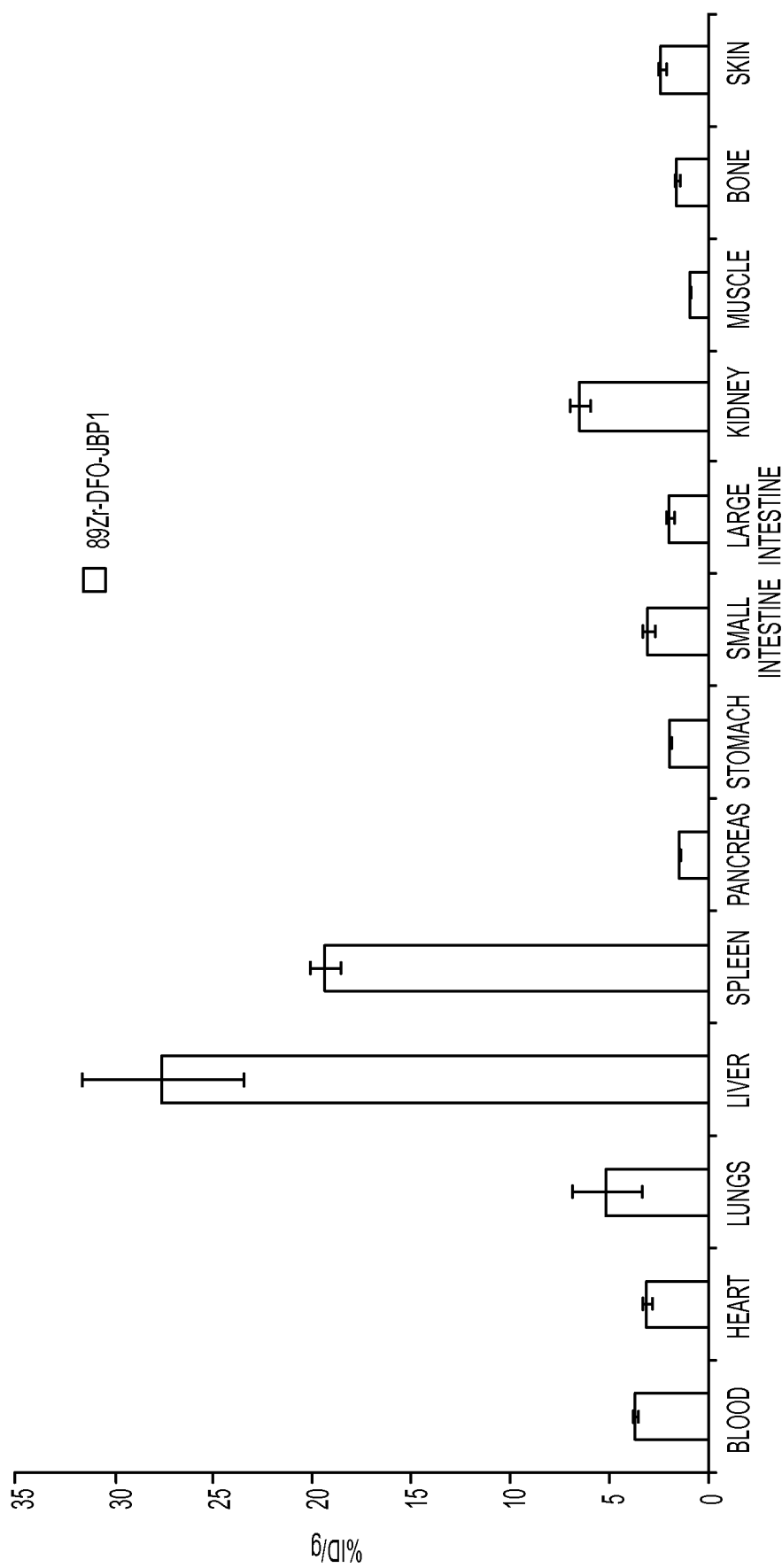

FIGS. 19A-19B show PET imaging and biodistribution of $^{89}$Zr-Radiolabeled Polymer, $^{89}$Zr-DFO-JBP1.

FIG. 19A shows coronal PET images of $^{89}$Zr-DFO-JBP1. Healthy BALB/c mice (n=2) were intravenously administered $^{89}$Zr-DFO-JBP1 (~10 mg, ~100 µCi, 250 mL saline) and imaged at 2 h, 24 h, and 72 h post injection. Initial time points showed high activities in the blood, whereas at 72 h p.i most of the activities were detected in the liver.

FIG. 19B shows ex vivo biodistribution of $^{89}$Zr-DFO-JBP1 in select major organs. At 96 h p.i, the mice (n=2) were sacrificed, organs were extracted, and radioactivities and organ weights were measured and expressed as the % injected dose per gram of tissue.

Figure 20:
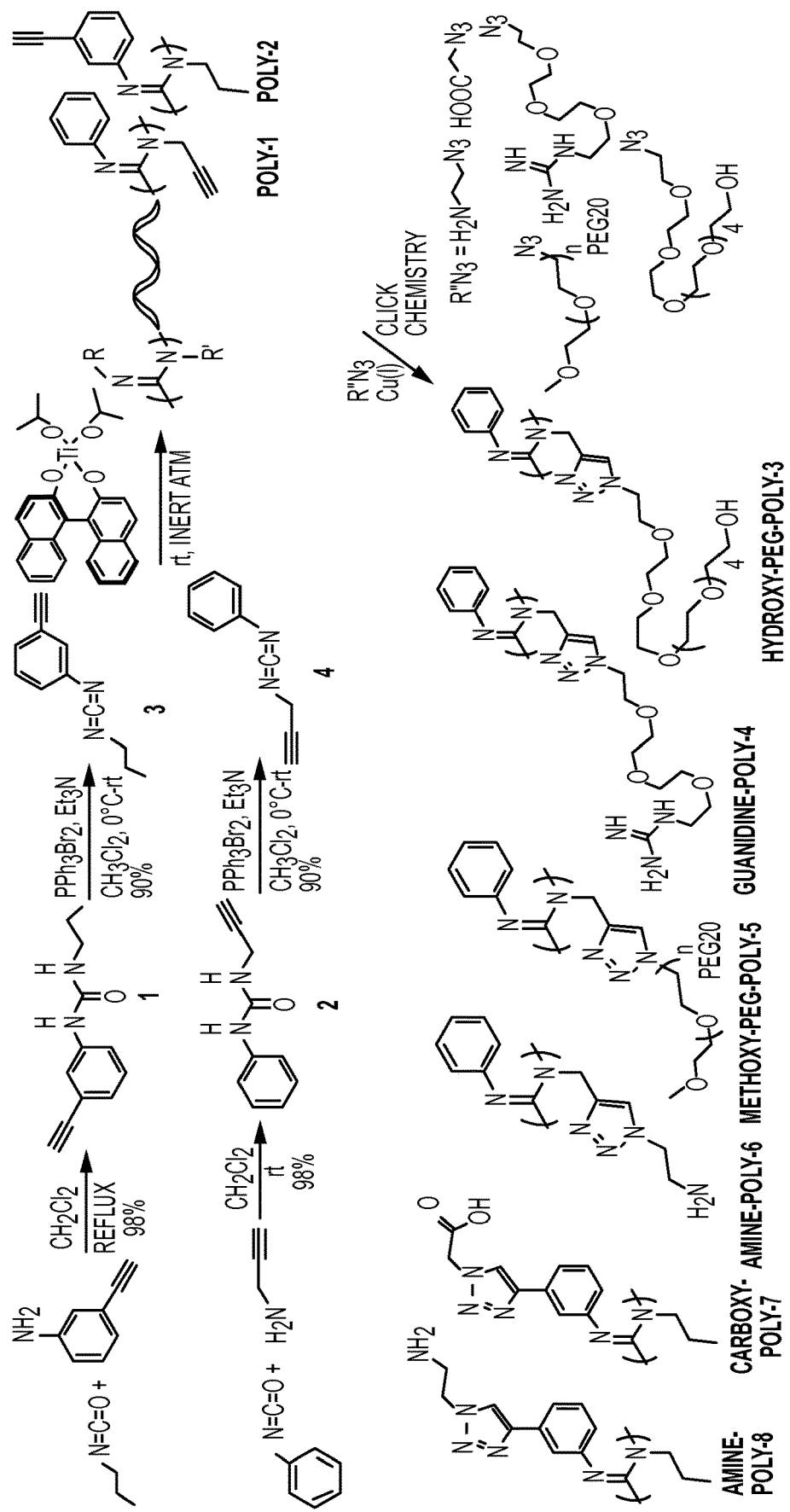

FIG. 20 shows synthesis of urea derivatives, monomers, and corresponding polymers as described herein.

Figure 21A:
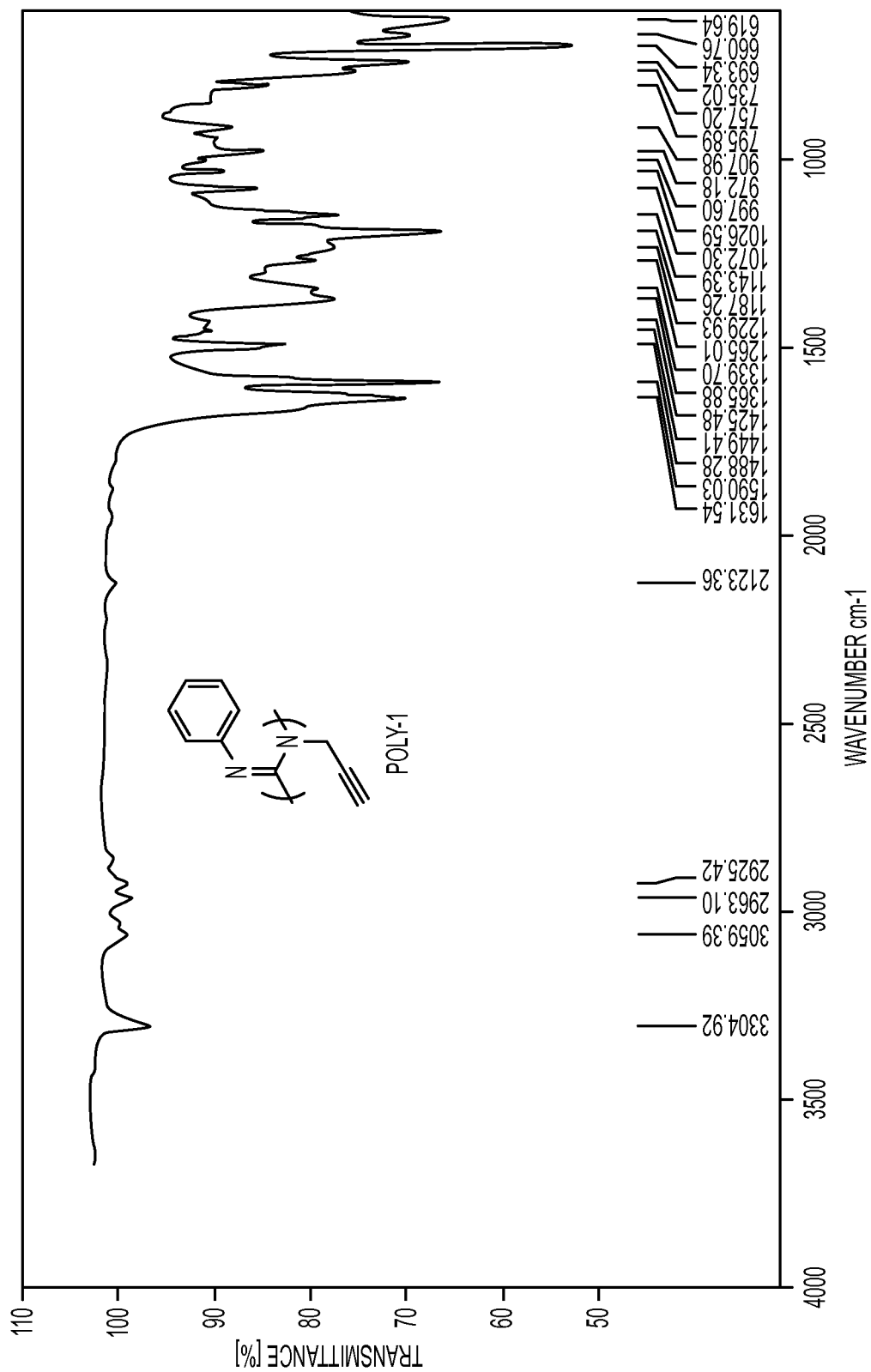
Figure 21B:
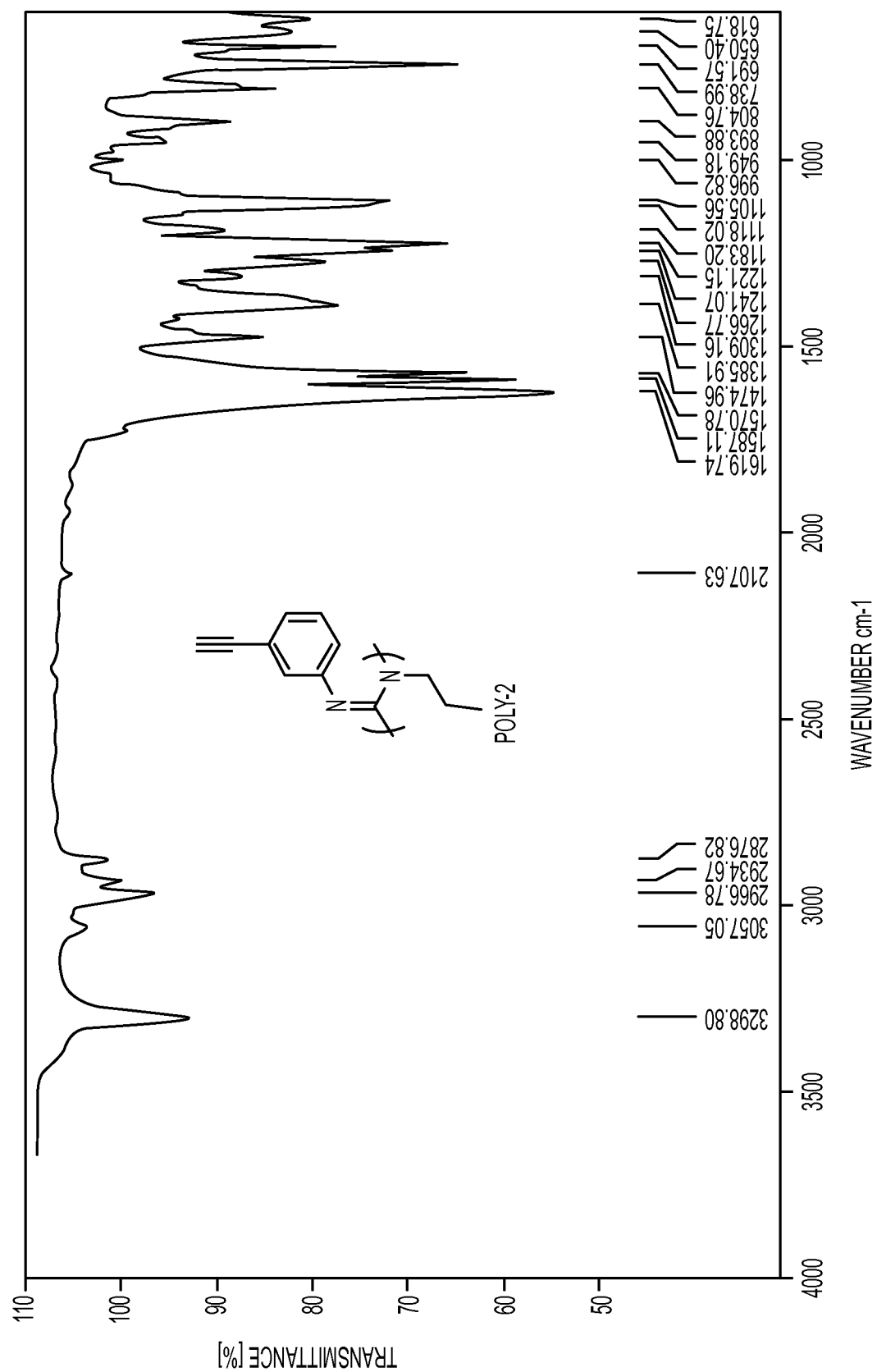

FIGS. 21A-21B show the FTIR spectra of polymers, Poly-1 and Poly-2, respectively.

Figure 22:
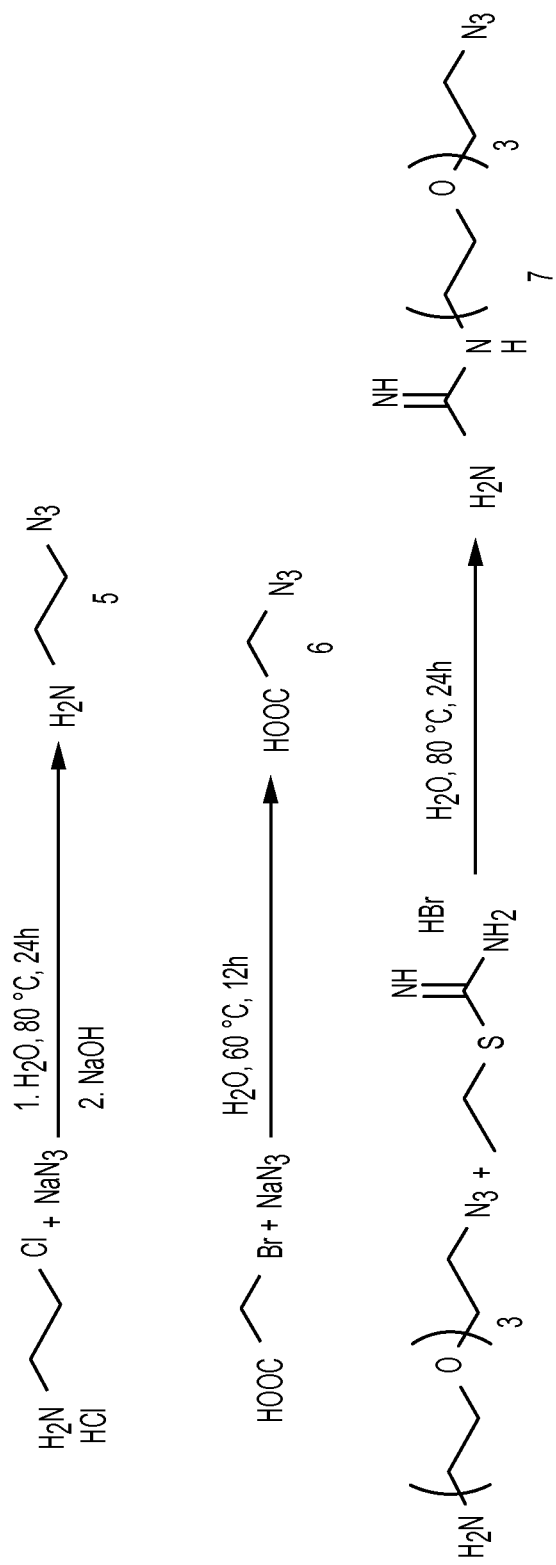

FIG. 22 shows azide compounds 5-7 that were synthesized and characterized in certain embodiments as described herein.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are suspensions of helical polycarbodiimide polymers that 'cloak' nanotubes, thereby effecting control over nanotube emission, providing a new mechanism of environmental responsivity, and enabling precise control over sub-cellular localization. The helical polycarbodiimide polymers described herein are water soluble, easily modifiable, and have unique architectures that facilitate their application in radiopharmaceutical delivery and imaging methods, in therapeutics and therapeutic delivery methods, and their use as sensors—both in conjunction with carbon nanotubes, and without nanotubes.

For example, the helical polycarbodiimide polymers can be modified with radionuclides or radionuclide-chelating agents. Experiments performed with these polymers—for example, DOTA-modified polymer with multiple chelation sites for Lutetium-177—demonstrate rapid clearance and low organ update, especially in the kidneys.

The helical polycarbodiimide polymers can also deliver molecules and increase drug binding affinity via multivalency, lending to their use as therapeutics and in therapeutic delivery, for example, opiate-polymer conjugates that provide long-term analgesic effects, as well as treatment of cancer, atherosclerosis, skin disorders, infectious diseases, and other diseases. Due to the semi-rigidity of the polymer, more binding sites are accessible, compared with polymers having a globular form. Furthermore, the helical polymer lengths are short and very controllable, allowing for rapid clearance if desired.

Moreover, the helical polymers described herein are demonstrated to encapsulate single-walled carbon nanotubes, which are used as fluorescent sensors for in vitro, ex vivo, and in vivo applications. The polymers provide both sensitivity to specific, desired bioanalytes, and direct/target the sensors to specific locations in the cell and body. Polymer-nanotube constructs are shown that provide nuclear, cytosolic, and extracellular localization. Moreover, a stable polymer-nanotube sensor is presented for in vitro and in vivo redox potential measurements.

In addition, the helical polymers described herein are demonstrated to be radiolabeled and serve as multimodal targeted molecular imaging probes for early cancer, such as pancreatic cancer, detection. The polymers integrate multimeric targeting ligands for receptors in cancer cells to achieve high tumor specific uptake and retention, contain multiple chelators to chelate multiple radiometals for enhanced specific activity and quantitative PET imaging, and allow tunable hydrophilicity through minimal structural changes to increase plasma stability, prolong probe circulation in vivo, improve pharmacokinetics, and reduce immunogenicity.

Example 1: Helical Polycarbodiimide Cloaking of Carbon Nanotubes

In the examples described herein, a platform of helical polycarbodiimide polymers was synthesized to 'cloak' the nanotubes which affected control over nanotube emission, provided a new mechanism of environmental responsivity, and enabled precise control over sub-cellular localization. The helical polymers exhibited ordered surface coverage on the nanotubes, allowed systematic modulation of nanotube optical properties, and produced up to 12-fold differences in photoluminescence efficiency. The polymers facilitated controllable and reversible inter-nanotube Förster resonance energy transfer, allowing kinetic measurements of dynamic self-assembly and disassembly. Tailored polycarbodiimide substituent groups also enabled sub-cellular targeting for imaging, including stable translocation of photoluminescent nanotubes within live cell nuclei.

Synthetic helical polymers mimic the basic structural motifs of vital biomolecules such as DNA and peptides. The functions of helical polymers depend on conformation, chain flexibility, and on the array of functional moieties along the polymer backbone. Polycarbodiimides are synthetic helical polymers with tunable properties. Polycarbodiimide regioregularity is shown through $^{15}N$-isotope labeling studies demonstrating precise control of the polymer microstructure and post-modification in a regioregular polycarbodiimide, resulting in a polymer chain with a regular array of functional side chains.

Figure 1A:
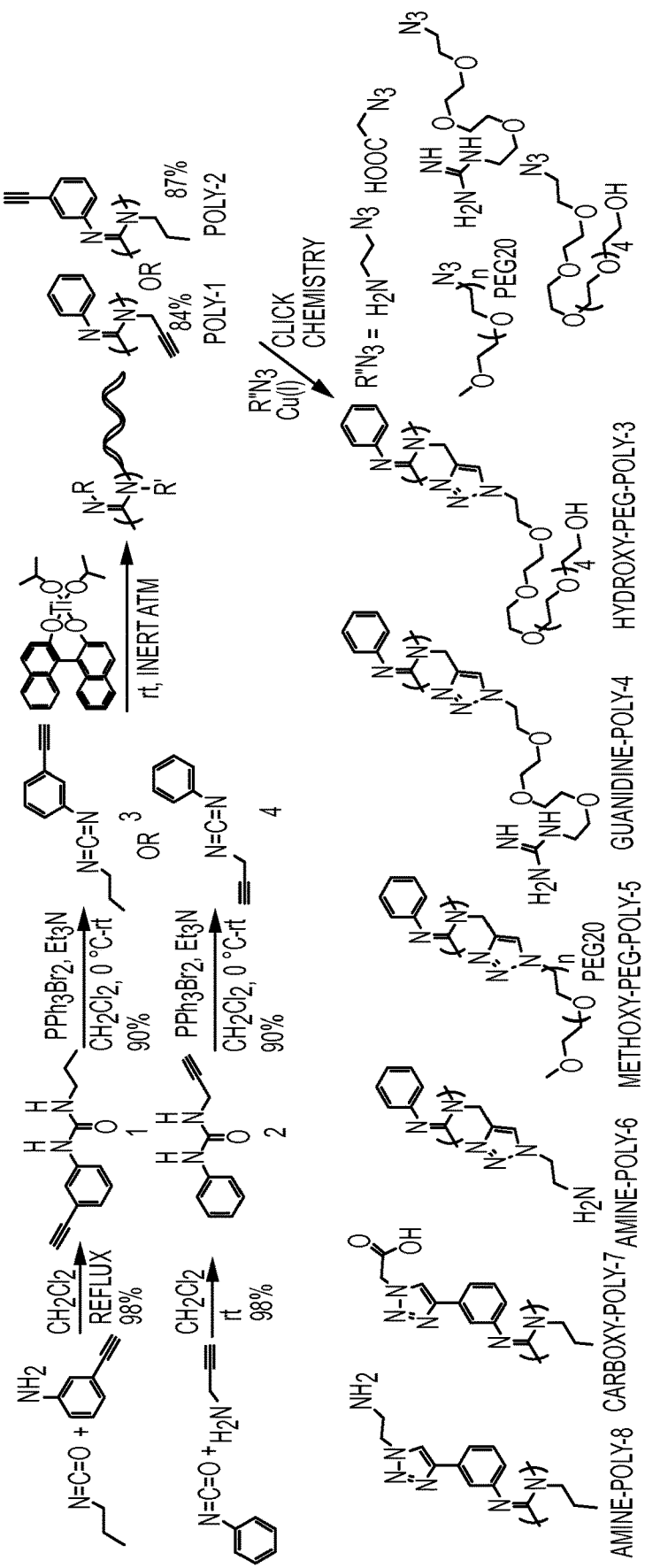
FIGS. 1A-1B depict preparation of polycarbodiimide-SWCNT complexes.
Figure 1B:
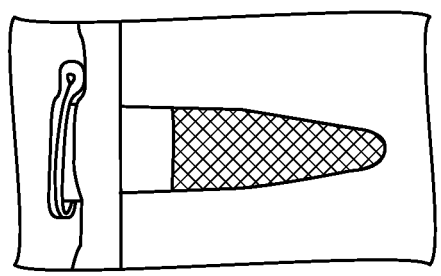
Figure 1B:
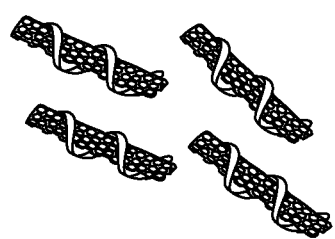
Figure 1B:
Figure 1B:
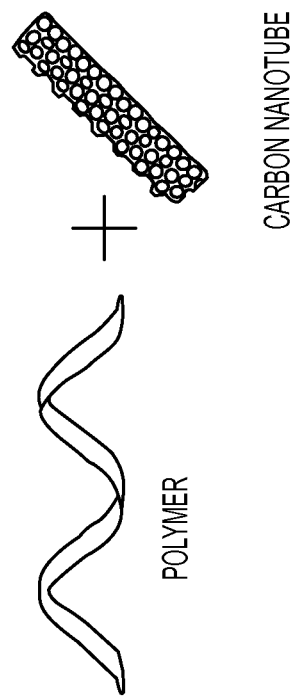

A modular polycarbodiimide polymer system is presented herein that cloaks nanotubes in repeating chemical functional units and suspends pristine nanotubes in aqueous solutions. Alkyne polycarbodiimides (Poly-1 and Poly-2) were synthesized and organic azides were subsequently coupled to terminal alkyne groups in these polymers via Cu(I) catalyzed alkyne-azide cycloaddition, as depicted in FIG. 1A. Side chains in these polymers such as primary amines, carboxylic acids, guanidine groups, and oligoethylene glycols were incorporated to mimic side chains in polylysines, polyglutamic acids, and polyarginines, and to increase water solubility. Additionally, aromatic groups were incorporated in each monomer substituent 3 and 4 (FIG. 1A) to promote multi-valent π-π interactions between the polymer and the graphitic sidewall of SWCNTs. Raw SWCNTs (Unidym, HiPCO) were sonicated in the presence of a polycarbodiimide from the library (Poly 3-8) to render them soluble in an aqueous solution. The insoluble materials were pelleted via ultracentrifugation and removed, yielding a dark aqueous supernatant (FIG. 1B). Excess free polymer was then removed from the suspensions by centrifugal filtration. The aqueous suspensions were stable under ambient conditions for several months, with no visible aggregation.

Figure 2A:
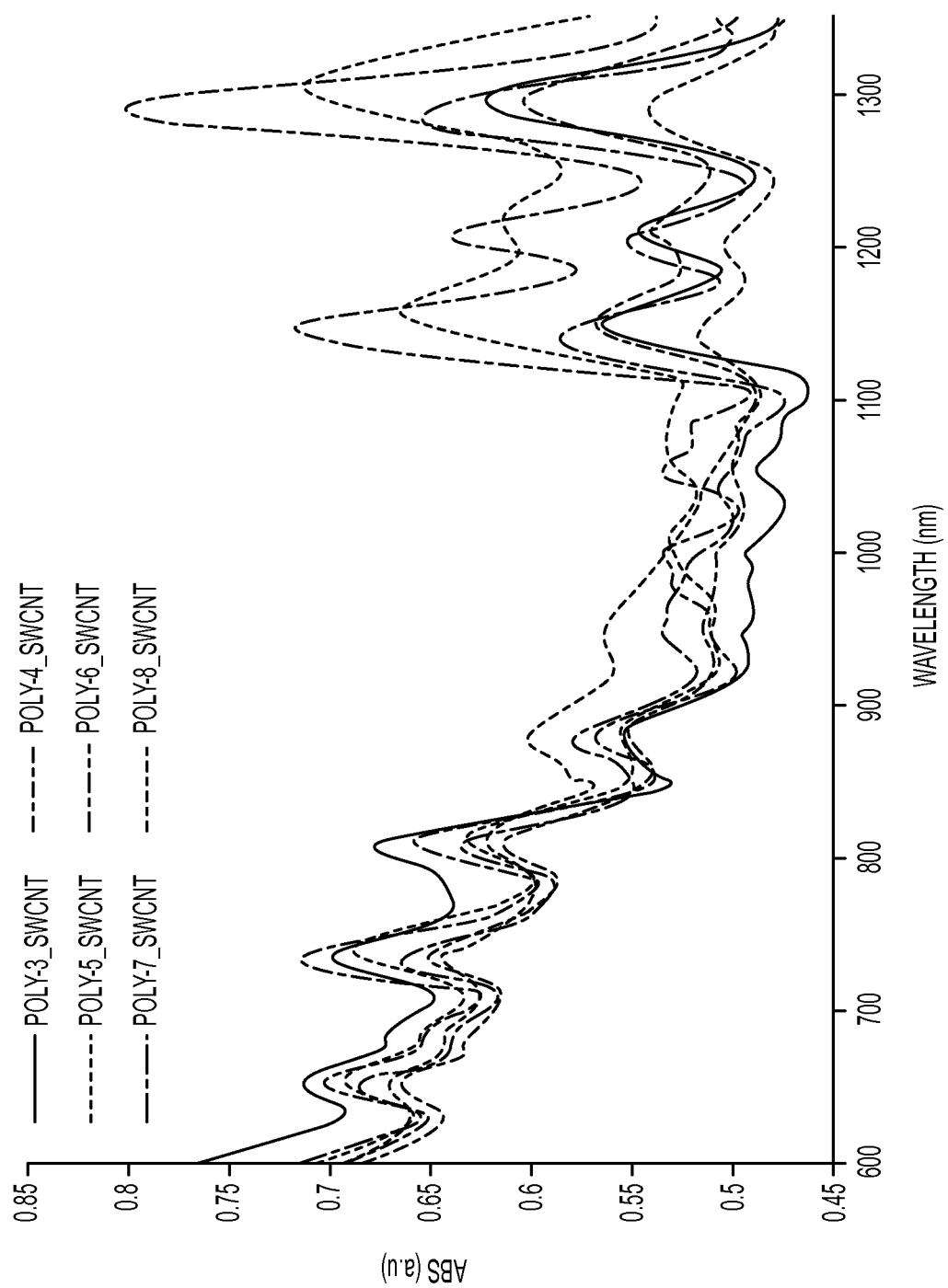
FIGS. 2A-2F show optical and morphological properties of polycarbodiimide-SWCNTs.
Figure 2B:
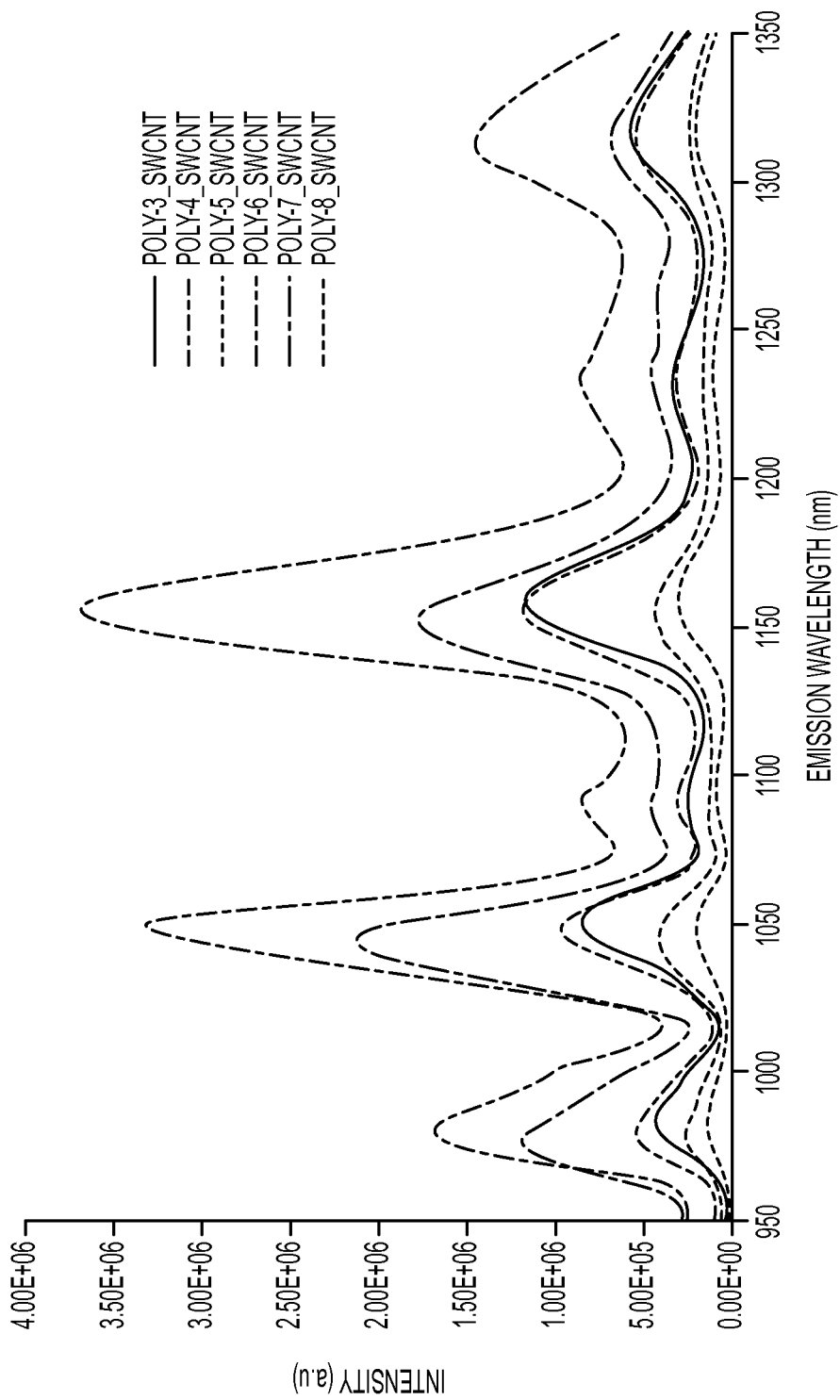

Polycarbodiimide-SWCNT complexes were characterized by absorption spectroscopy in the vis-nIR region. Absorption spectra of all polycarbodiimide-SWCNT complexes in FIG. 2A shows characteristic $E_{22}$ and $E_{11}$ transition features of semi-conducting SWCNTs. Sharp, discrete peaks in the absorption spectra are indicative of well-dispersed nanotubes. The photoluminescence efficiencies of the polymer-nanotube complexes varied with the encapsulating polymer. FIG. 2B shows the photoluminescence intensities from polycarbodiimide-SWCNTs differing up to 12-fold, depending on the polymer substituent functional group as well as the polymer microstructure. Such trends are similar to findings reported for DNA-encapsulated SWCNTs.

Figure 2C:
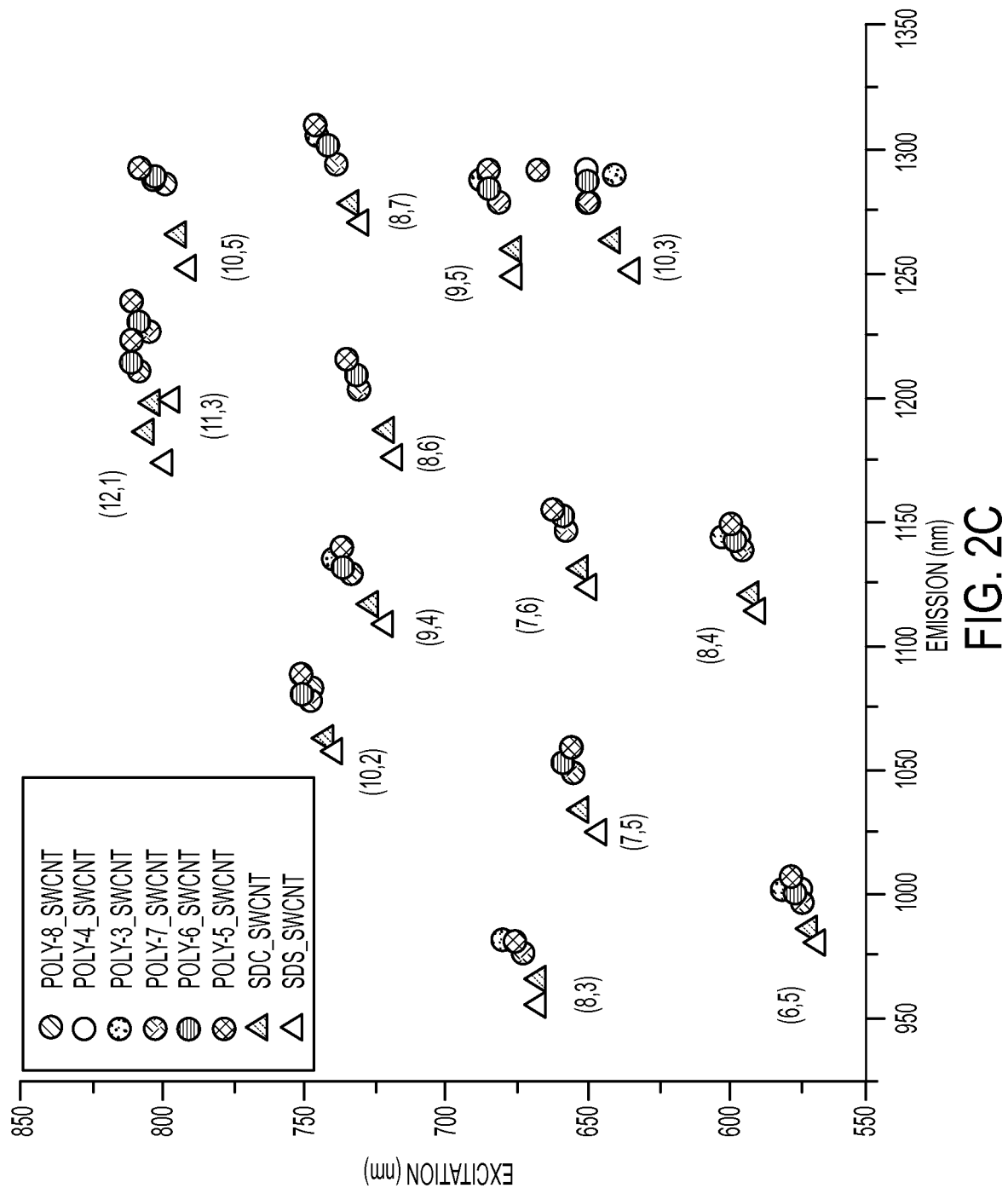
Figure 2D:
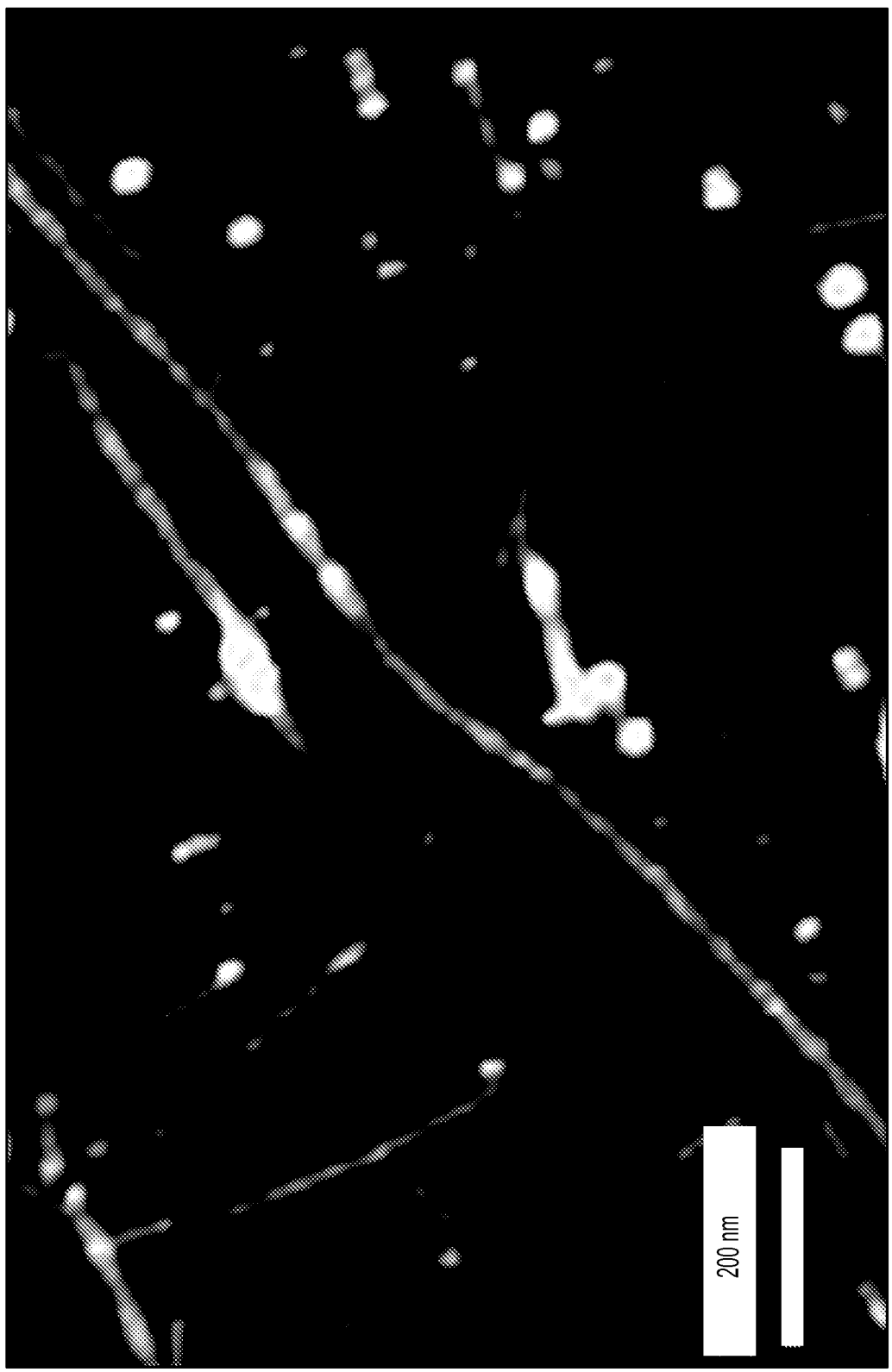
Figure 2E:
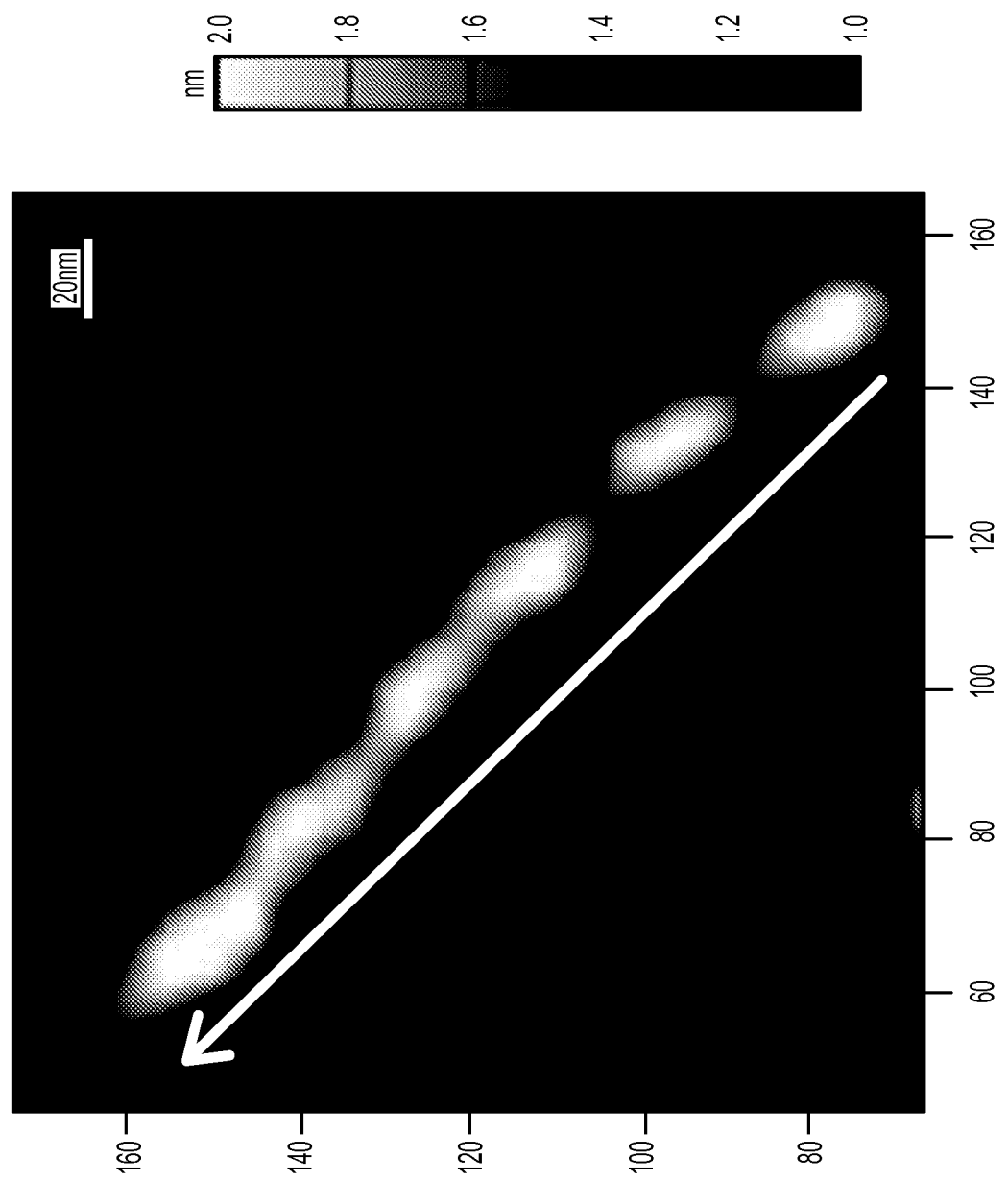
Figure 2F:
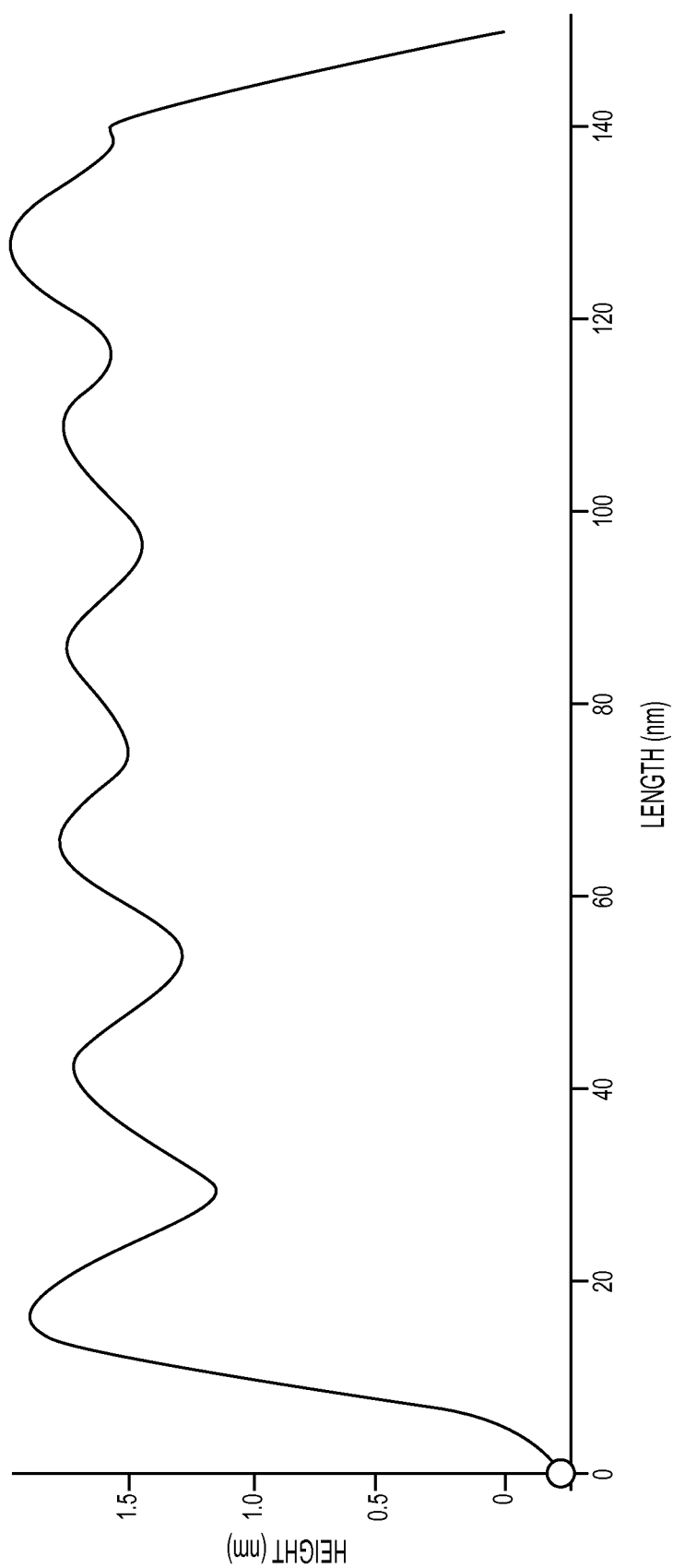
Figure 3A:
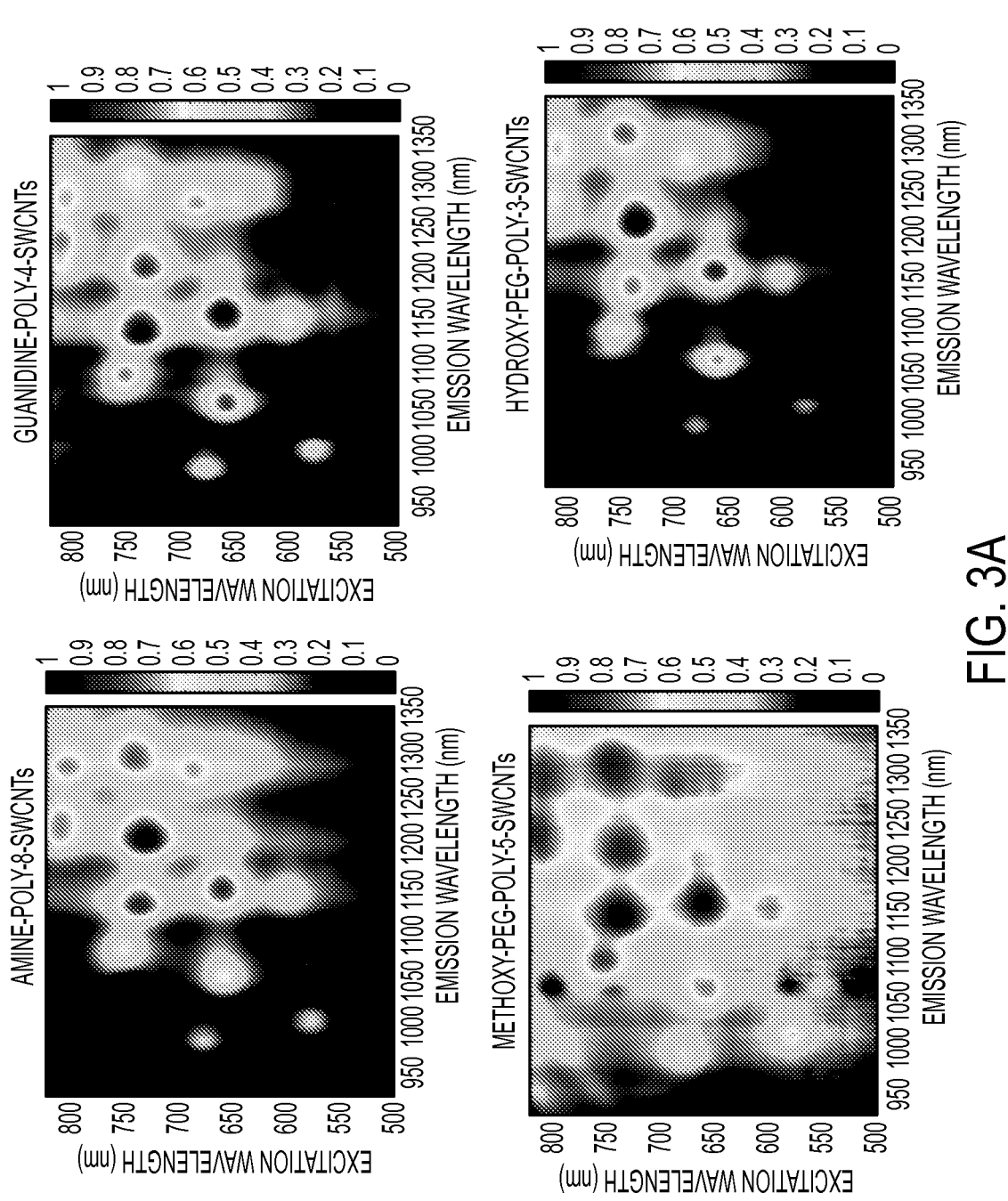
FIGS. 3A-3B show two-dimensional near-infrared photoluminescence excitation/emission (PLE) plots showing normalized emission intensity from polycarbodiimide-SWCNTs and surfactant suspended SWCNTs (SDS and SDC) as a function of excitation wavelength.
Figure 3B:
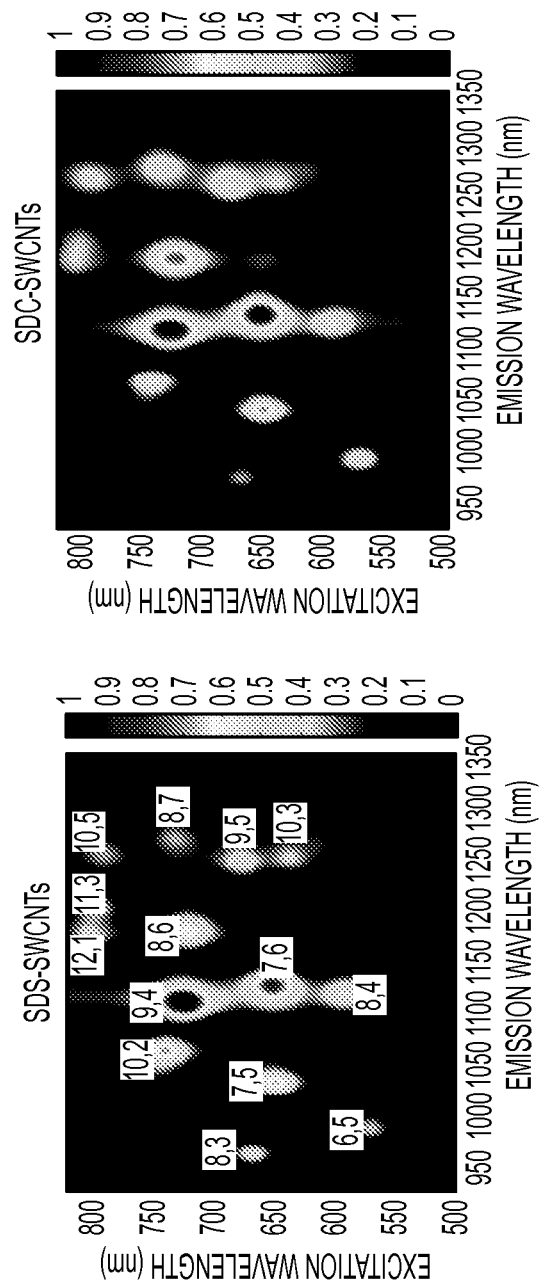
Figure 4A:
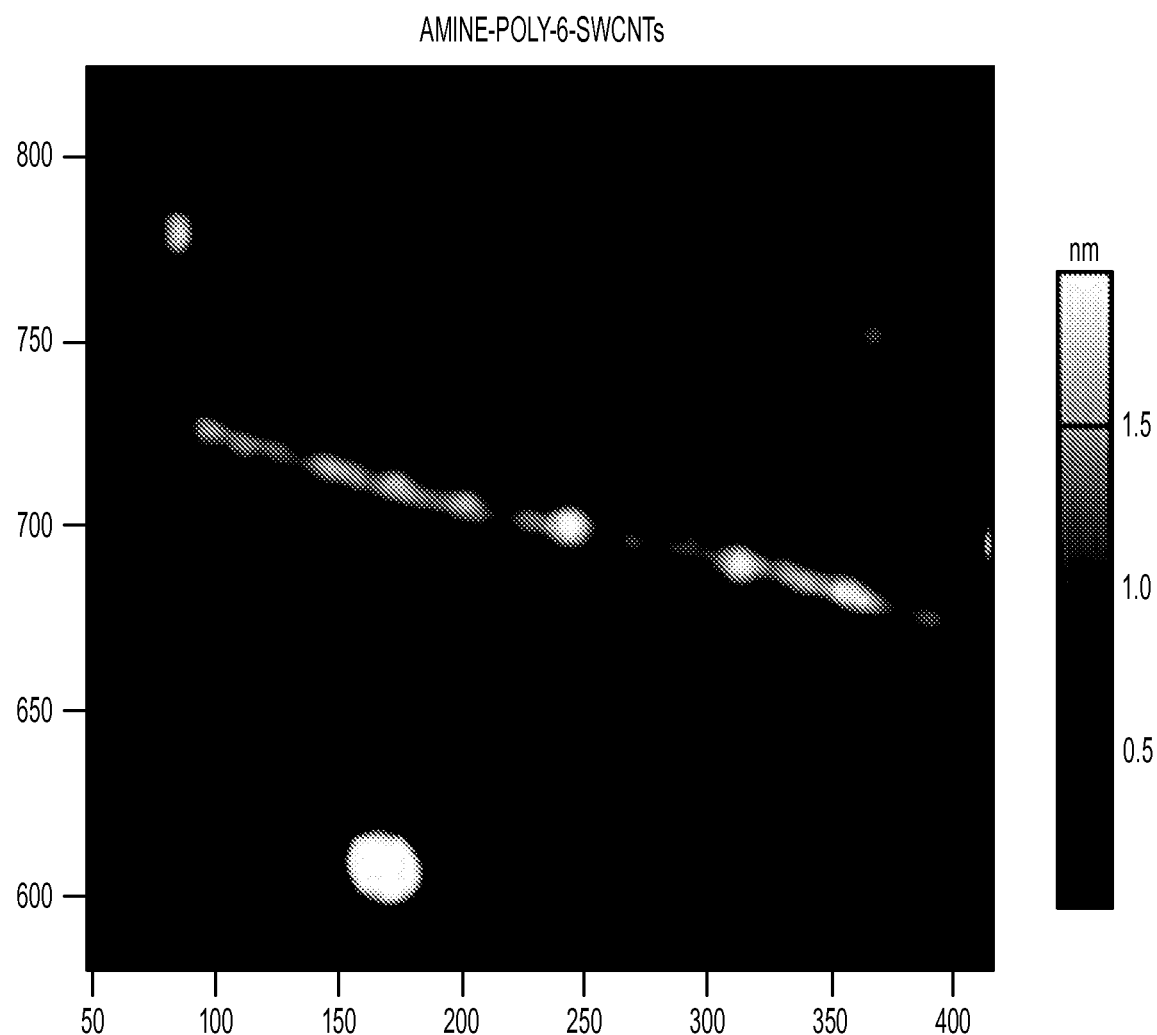
FIGS. 4A-C show atomic force microscopy and transmission electron microscopy images of polycarbodiimide-SWCNTs.
Figure 4B:
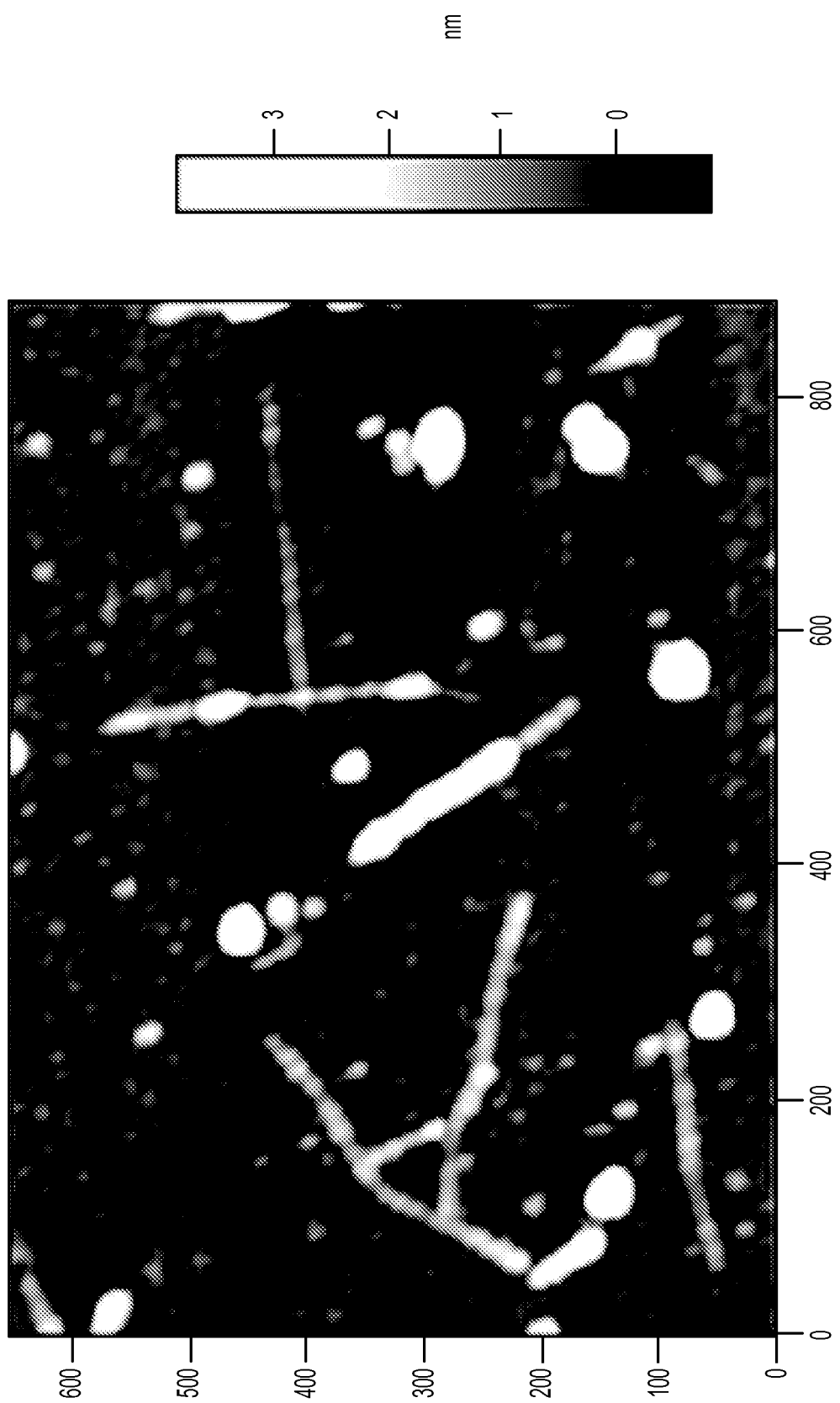
Figure 4C:
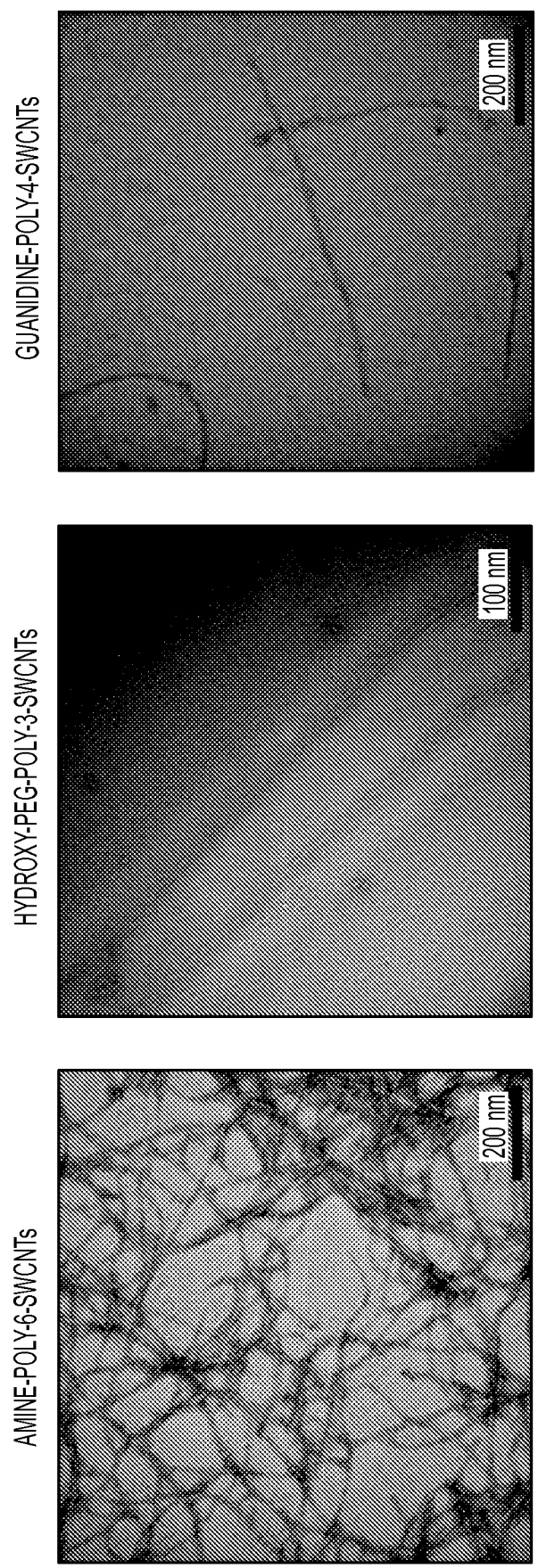

Two-dimensional photoluminescence excitation/emission (PLE) spectroscopy was conducted on polycarbodiimide-SWCNTs by recording emission spectra upon varying the excitation wavelength, as described below. Fourteen distinct nanotube species detected in 2D PLE plots on polycarbodiimide-SWCNT complexes (FIGS. 3A and 3B) were assigned (n, m) chirality indices. Excitation and emission wavelength maxima, collected from the PLE plots fell within a narrow range which was red-shifted relative to surfactant-suspended SWCNT emission (FIG. 2C).

Atomic force microscopy (AFM) and transmission electron microscopy (TEM) were conducted to characterize polycarbodiimide-SWCNT morphology (FIGS. 2D-2F, FIGS. 4A-4C). Images of Amine-Poly-8-SWCNTs, deposited and dried on freshly cleaved mica surface, show a distinct, periodic banding pattern along the nanotube surface. The patterns exhibit a spacing of ~20 nm along the nanotube axis and band heights up to ~0.8 nm-0.5 nm above the surface of the nanotubes. Without having to be bound by theory, these observations, coupled with the long-term stability of the polymer-nanotube suspension, suggest a uniform conformation of these aromatic polymers along the SWCNTs. These AFM micrographs are comparable to those from DNA encapsulated SWCNTs, where a regular banding pattern of DNA strands with a pitch of 14-20 nm along the nanotubes have been reported. Without having to be bound by theory, based on this regular pattern and the similarity to the pattern in DNA-SWCNTs which are predicted (by all atom molecular dynamics (MD) simulations) to helically wrap nanotubes via the π-π interactions, the polymer also likely helically-encapsulates the nanotubes.

Figure 5A:
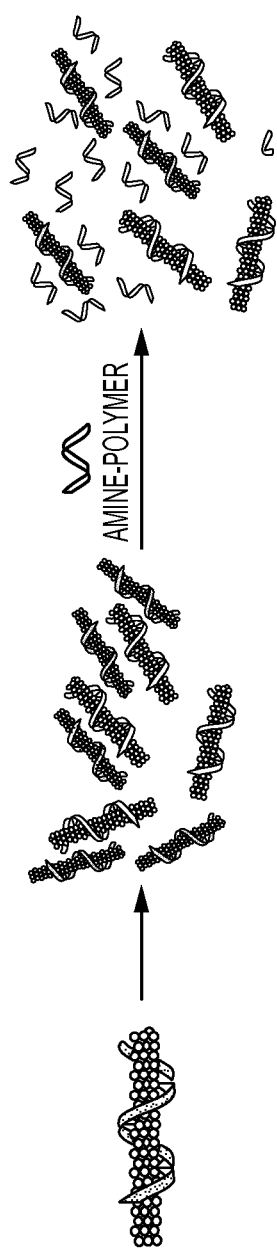
FIGS. 5A-5G show reversible inter-nanotube Förster resonance energy transfer (INFRET) in polycarbodiimide-SWCNTs.
Figure 5B:
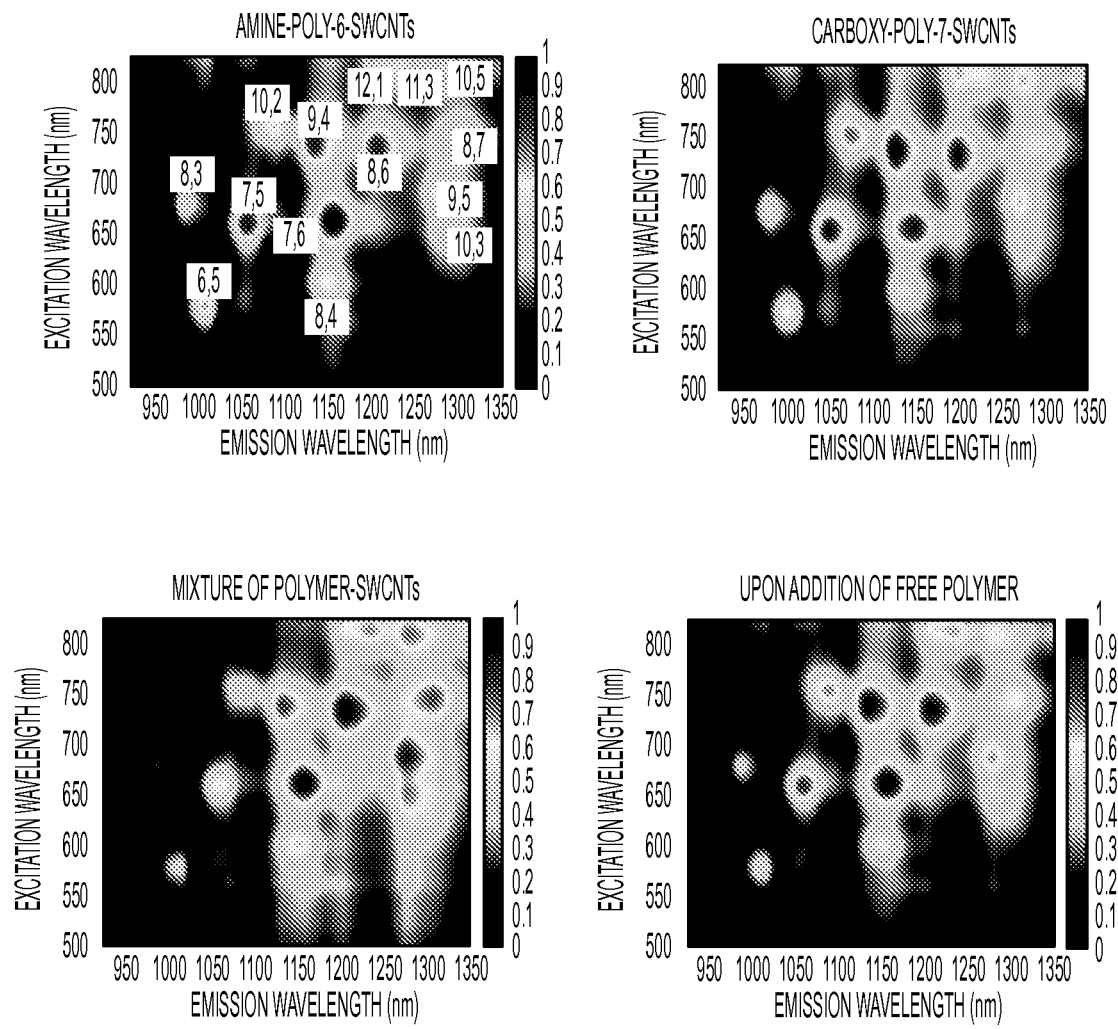
Figure 5C:
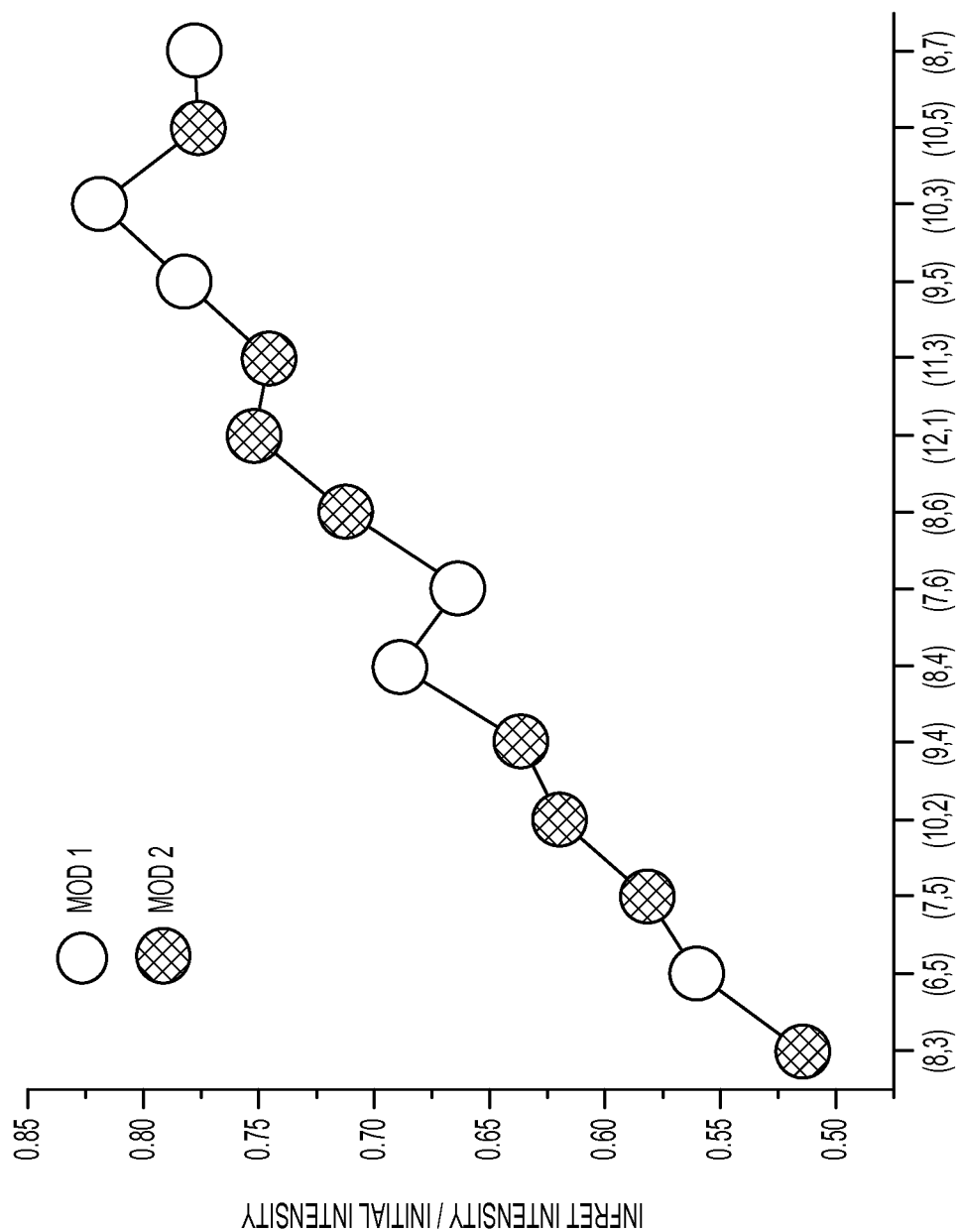
Figure 5D:
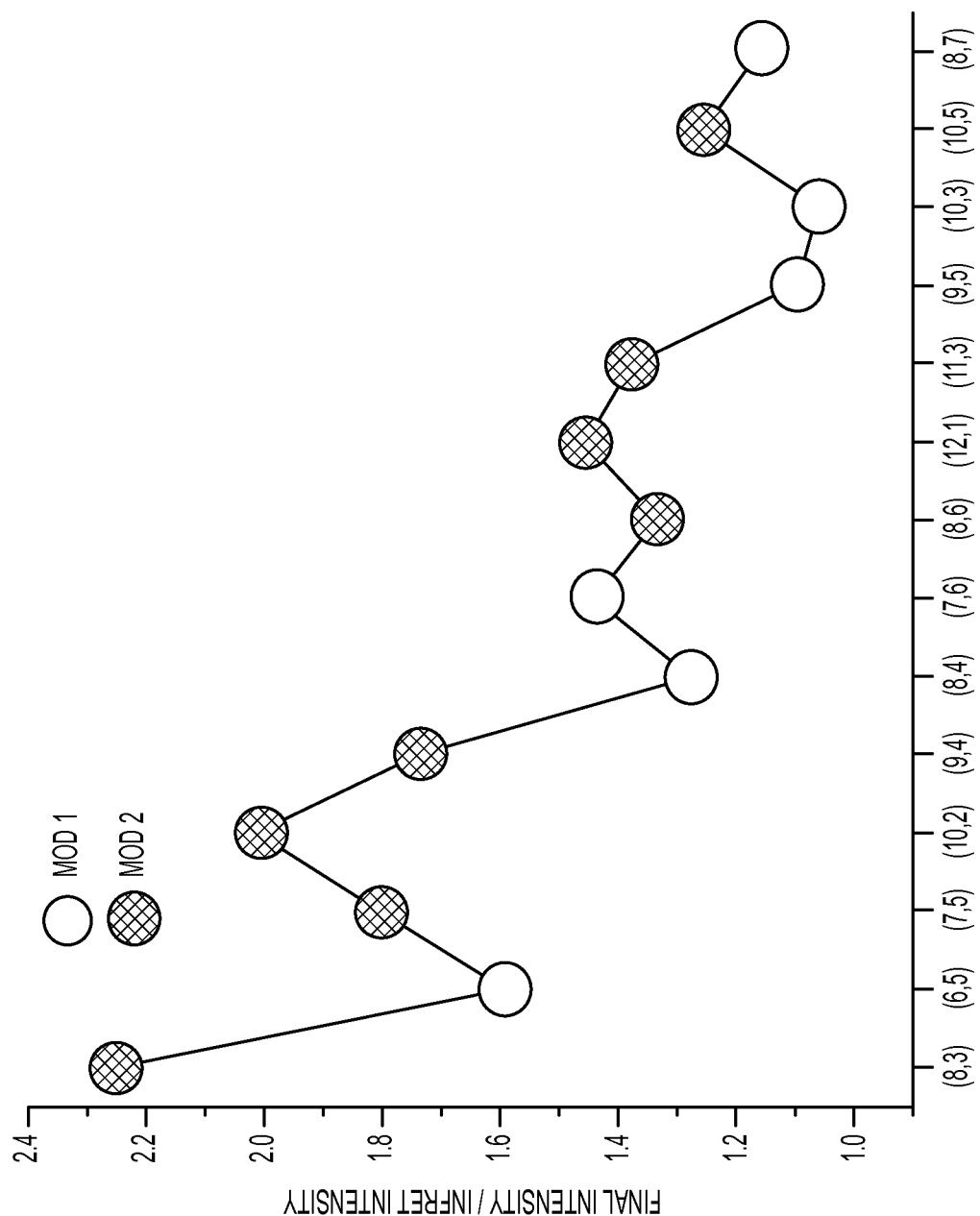
Figure 6A:
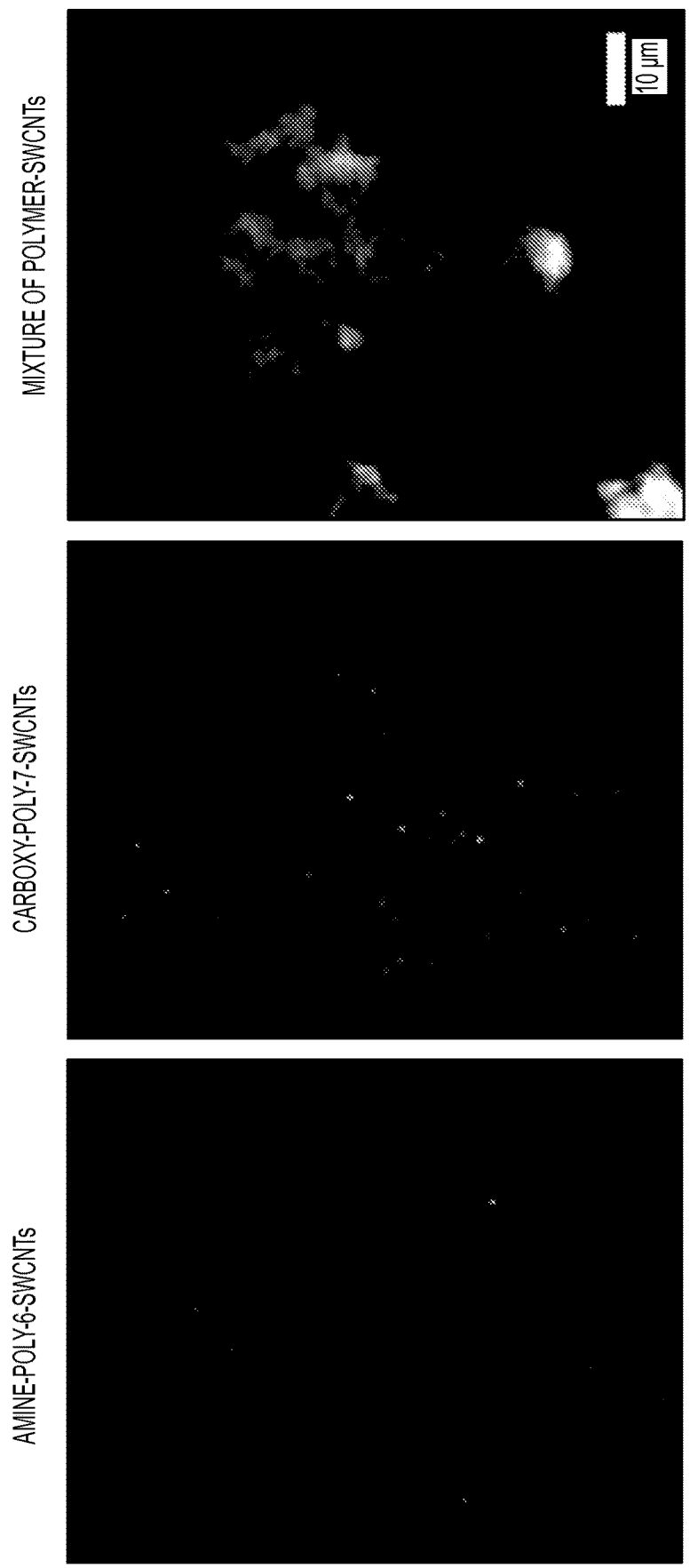
FIG. 6A shows near-infrared images of polycarbodiimide-SWCNTs immobilized on glass surfaces showing discrete fluorescent nanotubes (left and middle panels). Dilute solutions were placed on 35 mm glass bottom petri dishes for 10 seconds and excess solution was removed prior to imaging the nanotubes on the surface. The right panel shows nIR fluorescent aggregates of polycarbodiimide-SWCNTs after mixing the two nanotube complexes in solution. Carboxy-Poly-7-SWCNT was added to Amine-Poly-6-SWCNT (1:1 ratio) and left to stand for 10 sec; excess solution was removed from the surface prior to imaging.
Figure 6B:
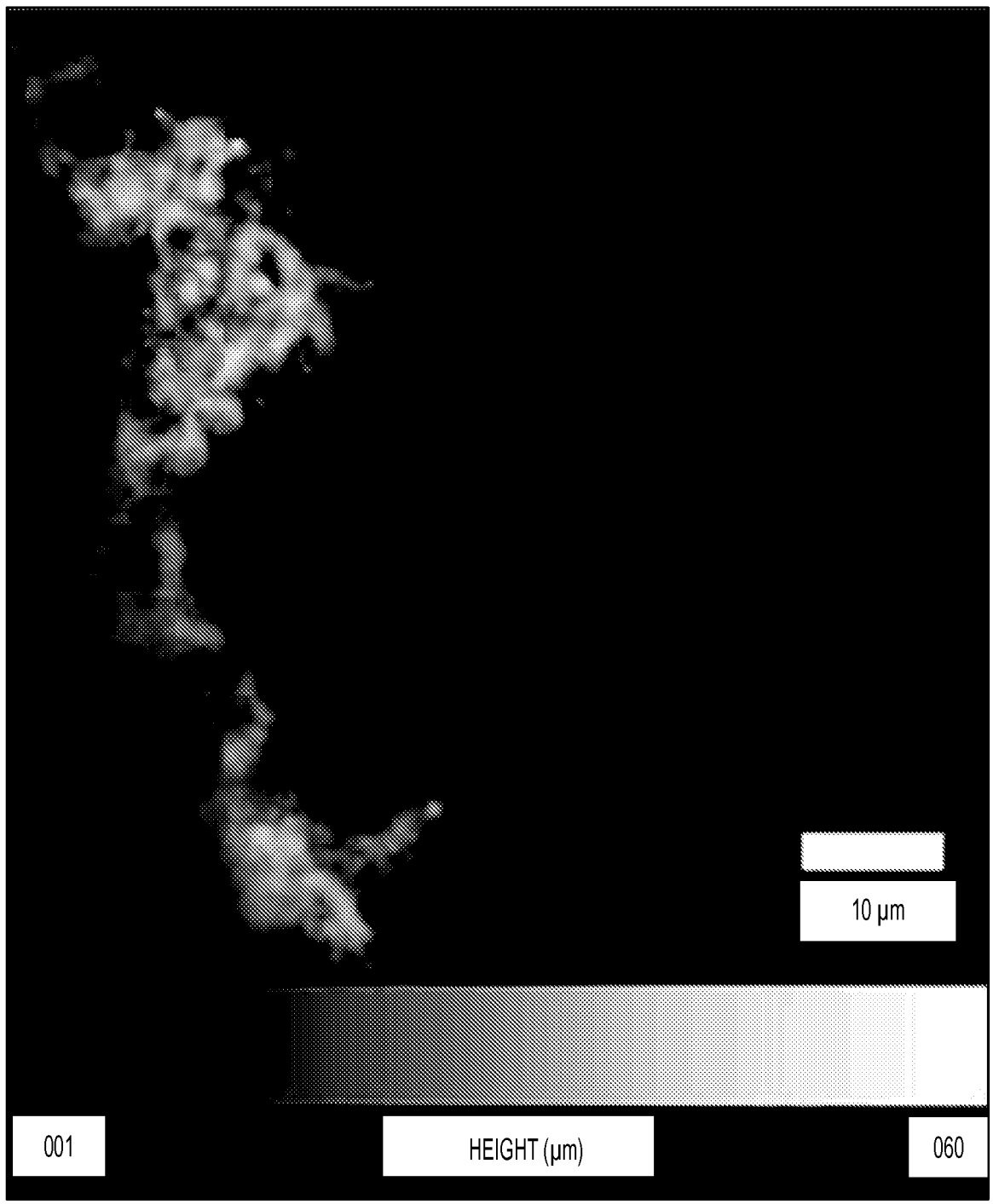
FIG. 6B shows height projection near-infrared image of polycarbodiimide-SWCNTs aggregates, generated by 3D deconvolution of a stack of images acquired in 10 μm Z-steps.
Figure 6C:
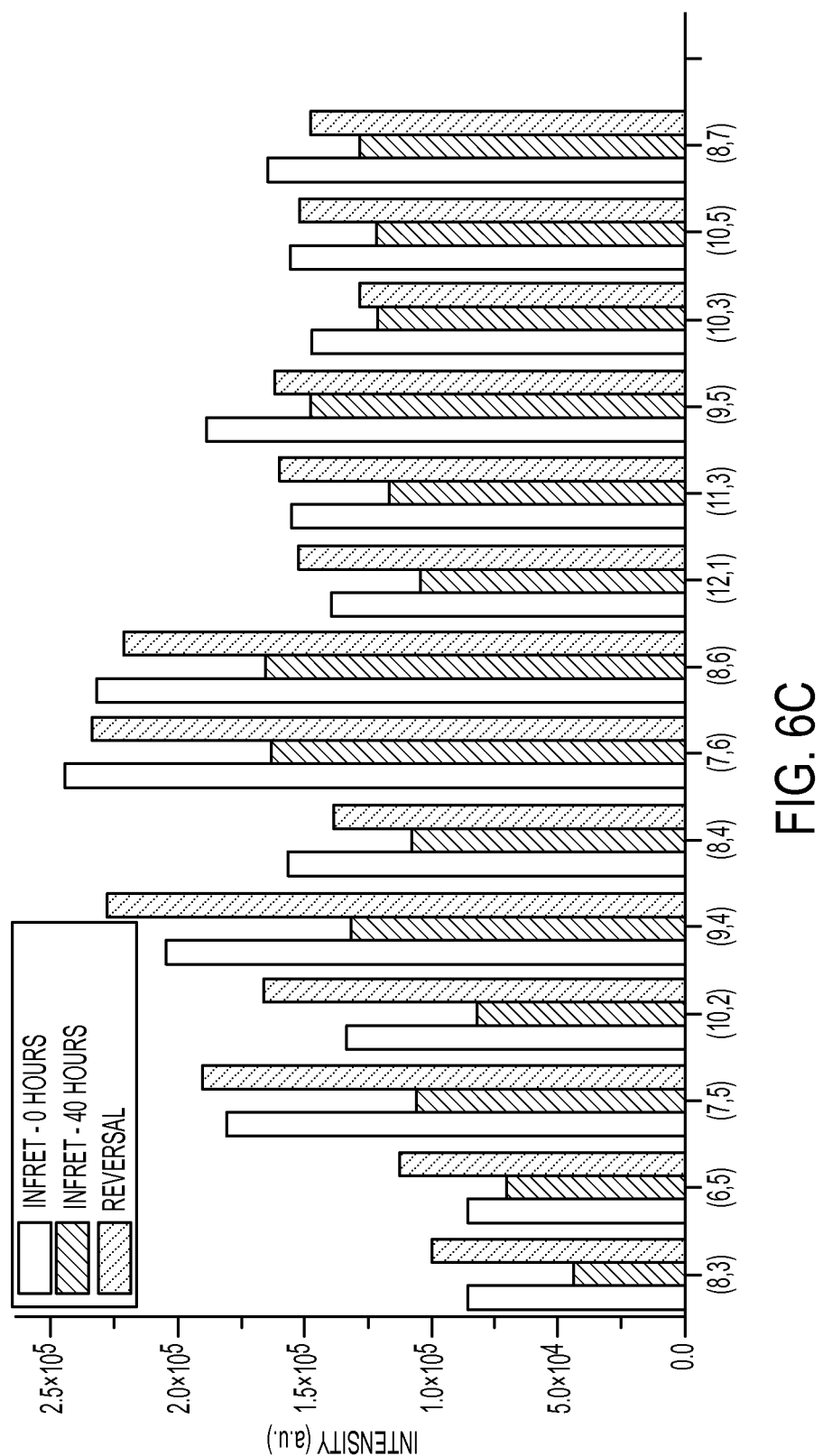
FIG. 6C shows PL Intensity change upon initiating and reversing self-assembly of Amine-Poly-7-SWCNTs and Carboxy-Poly-8-SWCNTs.

Förster resonance energy transfer (FRET), also described as exciton energy transfer (EET) in SWCNTs, has been observed between adjacent semiconducting nanotubes in van der Waals contact wherein large band gap donors transfer energy to smaller band gap acceptors. In small bundles, a center to center distance of 1-4 nm between nanotubes was shown to optimize energy transfer in SWCNTs. With a functionally-diverse set of polymer-SWCNTs in hand, the possibility of inter-nanotube Förster resonance energy transfer (INFRET) events between individually-encapsulated nanotubes in aqueous solutions was investigated. FIG. 5A is a schematic representation of the process. FIG. 5B shows 2D PLE plots of two oppositely-charged polymer-nanotube complexes (zeta potential values 67.93±2.73 mV for Amine-Poly-6-SWCNTs and −62.93±1.28 mV for Carboxy-Poly-7-SWCNTs) and the resulting mixture. Complexes were chosen to take advantage of strong coulombic attraction between basic primary amine groups and acidic carboxylic acid groups to bring nanotubes encapsulated in corresponding polymers into a favorable distance for INFRET, without creating irreversibly formed van der Waals bundles. Mixing the two polymer-SWCNT complexes resulted in fluorescent aggregates (FIGS. 6A-6B). Overall emission in PLE measurement decreased likely due to quenching induced by metallic SWCNTs in aggregates. However, the emission from smaller band gap SWCNTs increased with respect to that of large band gap SWCNTs (FIG. 5B). Extra peaks appeared in the short wavelength excitation/long wavelength emission range, a signature of energy transfer. The relative intensity increase was found to exhibit an (n, m) dependence which was virtually monotonic with emission wavelength (FIG. 5C). Excess amine-functionalized polycarbodiimide was later introduced to disrupt aggregation. Addition of the free polymer resulted in a recovery of the original relative PL intensities concomitant with the disappearance of large aggregates (FIG. 5B, FIG. 6C). Plotting the net recovery of (n, m) intensities showed a semi-monotonic trend with emission wavelength and apparent mod-dependent behavior (FIG. 5D).

Figure 5E:
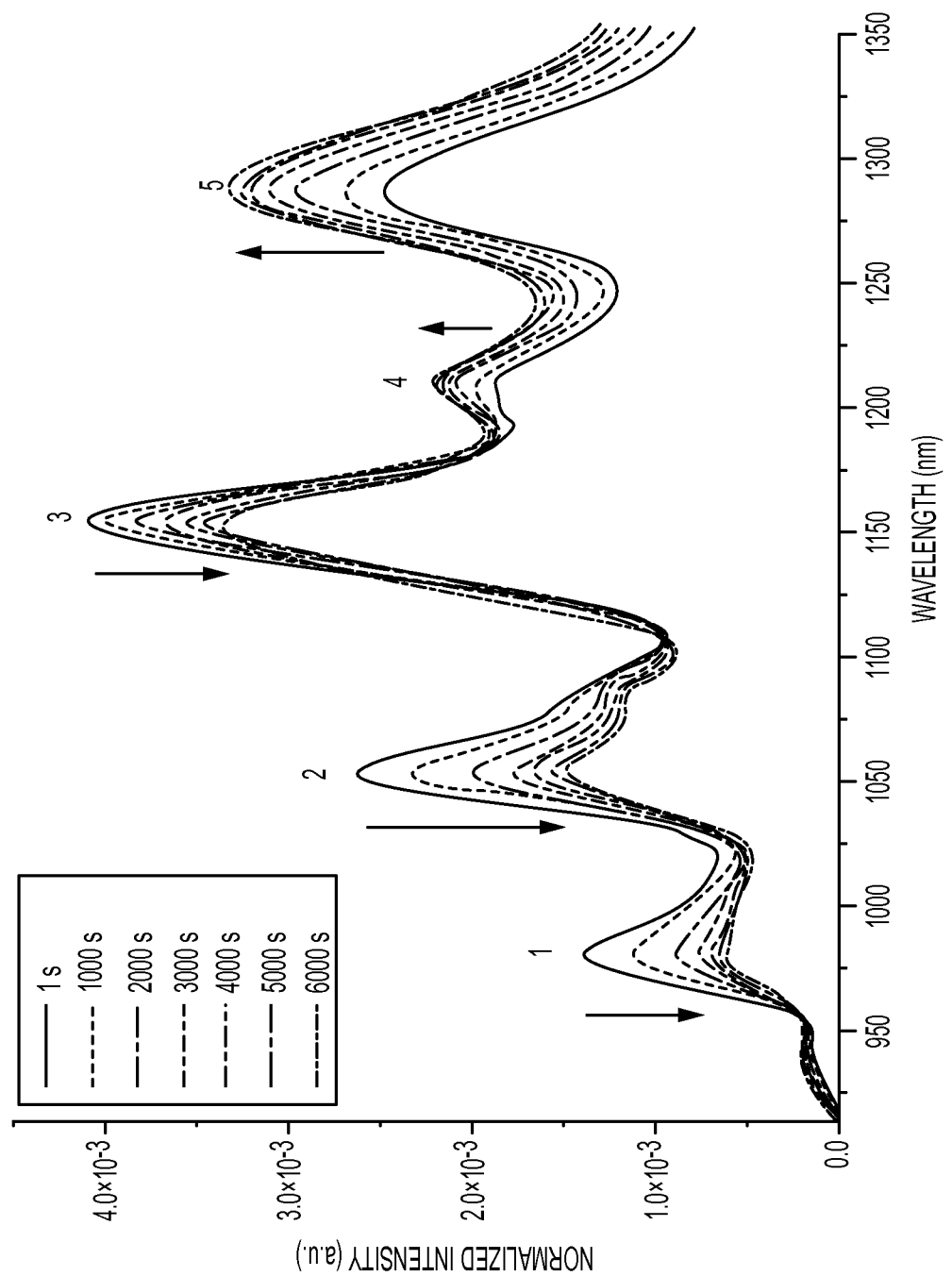
Figure 5F:
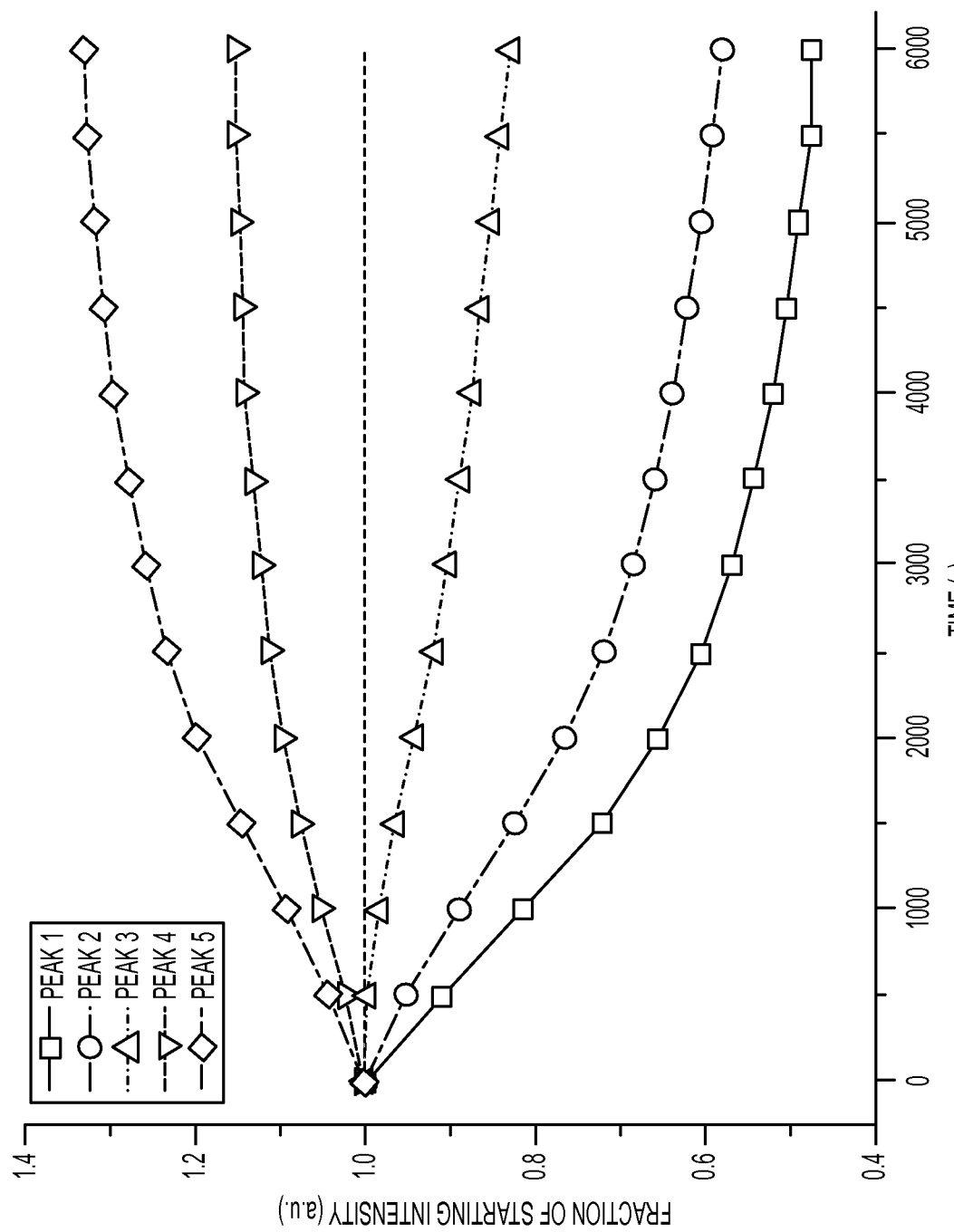
Figure 5G:
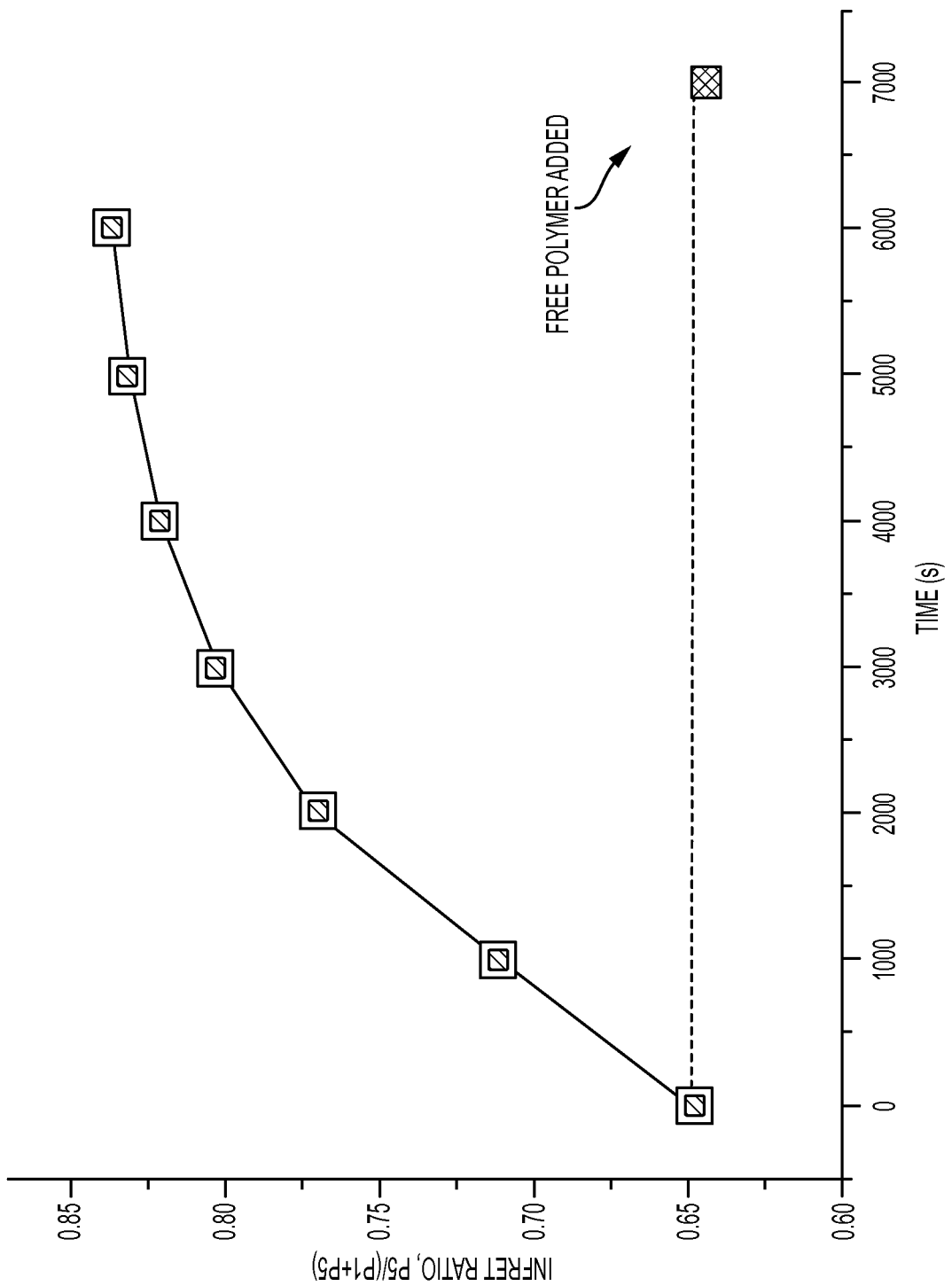

Real-time measurements of INFRET dynamics illustrate that the process is spontaneous, controllable, and reversible. Upon mixing the aforementioned oppositely-charged nanotubes, the fluorescence exhibited a monotonic decrease in PL intensities from large bandgap nanotubes (Peaks 1-3, FIG. 5E) and simultaneous relative increase from small bandgap nanotubes (Peaks 4 and 5, FIG. 5E). The relative fluorescence intensities of each peak, plotted over time, illustrate the INFRET dynamics between large and small band gap nanotubes (FIG. 5F). Each intensity-time curve was fit with the logistic function to obtain the time for half-maximal intensity change (FIGS. 7A and 7A-1), due to this function's use in the approximation of protein aggregation kinetics. However, the kinetics of Peak 1 and Peak 5 fit well as the reactant and the final product in a series of first order forward reactions, respectively (FIG. 7B). The first order behavior suggests that the larger bandgap nanotubes within Peak 1 act almost purely as energy donors and the smaller bandgap nanotubes within Peak 5 as energy acceptors. After 110 minutes, amine-functionalized polycarbodiimide polymer (0.5 mg/mL) was added and gently mixed, resulting in a near-instantaneous reversal of INFRET back to the initial ratio. Using the above information, The INFRET ratio, plotted as $I_a/(I_a+I_d)$ where $I_a$ is the acceptor intensity and $I_d$ is the donor intensity, was obtained using Peak 5 as the acceptor and Peak 1 as the donor (FIG. 5G).

The finding demonstrates FRET produced between nanotubes not contained within an irreversible bundle, but rather employing coulombic attraction between polymers permitted spontaneous forward and directed reversibility. Therefore, the described compositions are useful, for example, for the measurement of dynamic processes.

The biological fate of the polycarbodiimide-cloaked carbon nanotubes was found to depend almost completely on the encapsulating polymer substituent groups. Cellular interactions of polycarbodiimide-SWCNTs in human cervical cancer cells (HeLa cells) were investigated. Polycarbodiimide-nanotube complexes exhibited substituent-dependent uptake and localization into specific sub-cellular spaces (FIGS. 8A-8C). The cellular uptake was highly diminished in the case of polyethylene glycol polymer pendant groups (FIG. 8A, panel A1), comparable to lack of cellular uptake of PEGylated gold nanoparticles.

Upon internalization, sub-cellular distribution of nanotubes was dictated by the nature of the encapsulating polymer substituent groups. The anionic Carboxy-Poly-7-SWCNTs accumulated in perinuclear areas (FIG. 8A, panel A2), resembling the cellular distribution of DNA-encapsulated nanotubes. The two amine-functionalized polymer-nanotube constructs exhibited sub-cellular distribution profiles where a small fraction localized within the nucleus and the majority situated elsewhere within the cell (FIGS. 8A, panel A3 and 8C, panel C1). Nanotubes encapsulated in polymers with guanidine side chains localized almost completely within the nuclear region (FIGS. 8A, panel A4 and 8C, panel C2, FIGS. 9A and 9B) as confirmed by co-localization of nIR fluorescent nanotubes with Hoechst nuclear dye (Molecular Probes). The nuclear translocation of cargoes by polyarginines and their derivatives has been attributed to the presence of guanidine moieties. Multiple copies of adjacent guanidine side chains in Guanidine-Poly-4 presumably mimicked polyarginine side chains, delivering their encapsulated nanotube cargos into the nuclei. The energy-dependence of complex internalization was confirmed by the lack of noticeable cellular uptake upon incubation at 4° C. (FIG. 8A, panel A5). Under experimental conditions, the polymer-SWCNTs posed no obvious toxicity to cells (viability greater than 90%, FIG. 10).

Micrographs were obtained to determine whether the variable surface chemistries of polycarbodiimide-SWCNTs allow penetration of intact human skin tissue topical exposure. The micrographs show accumulation of all tested polymer-nanotube complexes on the stratum corneum, the outermost layer of the skin, without evident penetration (FIG. 11).

Thus, the experiments show that non-covalent functionalization of SWCNTs through encapsulation in designed helical polycarbodiimides forms water soluble, well-dispersed, and nIR fluorescent nanotubes that are stable under ambient conditions. The polymers, used in certain embodiments as described herein, demonstrated controllable, reversible inter-nanotube FRET, enabling a mechanism for switchable biomolecular probes and sensors. The polymers, as used in certain embodiments as described herein, also demonstrate a system substituent-dependent sub-cellular localization of nanotubes, including stable localization in cell nuclei.

Example 2: Synthesis of Helical Polycarbodiimide Polymers, for Use in Therapeutic and Diagnostic Applications A synthesis scheme and molecular structures for helical polycarbodiimide polymers described herein are presented in FIGS. 12A-12C.

For synthesis of urea derivatives, a primary amine compound (RNH$_2$) (1.0 equiv) was diluted in anhydrous dichloromethane and added to an isocyanate compound (R'NCO) (1.2 equiv) in dichloromethane, stirred at low temperature, and kept cold in an ice bath. The reaction mixture was stirred at room temperature or refluxed overnight until the completion of the reaction. The solvent was removed in a rotary evaporator and crude white solid was purified by recrystallization in ethanol at 4° C. and dried to obtain white crystalline solid.

For synthesis of carbodiimide monomers, triethyl amine (2.5 equiv) was added to a suspension of dibromotriphenylphosphorane (1.2 mol equiv) in dichloromethane at low temperature and the reaction mixture was stirred at low temperature under inert atmosphere for 5 minutes. A urea derivative (1.0 equiv) was added to the reaction mixture and stirred until completion. The dehydration of the urea derivative into carbodiimide monomer was monitored by the formation of a very strong FTIR signal at ~2120-2140 cm$^{-1}$. Upon completion of the reaction, hexane was added to precipitate side products. The monomer compound was then extracted from the solid by hexanes. Crude monomer was further purified by column chromatography on silica gel using ethyl acetate:hexanes (1:2) and dried under reduced pressure to obtain a carbodiimide monomer as a colorless oil.

The catalyst was synthesized and characterized as described in Tang, H.; Boyle, P.; Novak, B., Chiroptical switching polyguanidine synthesized by helix-sense-selective polymerization using [(R)-3,3'-dibromo-2,2'-binaphthoxy](di-tert-butoxy)titanium(IV) catalyst. *Journal of the American Chemical Society* 2005, 2136-2142.

The polymers were synthesized following the procedure described in Budhathoki-Uprety, J.; Novak, B., Synthesis of Alkyne-Functionalized Helical Polycarbodiimides and their Ligation to Small Molecules using 'Click' and Sonogashira Reactions. Macromolecules 2011, 44 (15), 5947-5954. Briefly, the catalyst, either neat or dissolved in chloroform (0.2 mL per 500 mg monomer) was added to the monomer at room temperature and under inert atmosphere. The reaction mixture turned to dark red and solidified to an orange red solid. The polymerization process was monitored in FTIR by disappearance of IR signals from carbodiimide (~2140-2120 cm$^{-1}$) and formation of new IR absorption at ~1620-1640 cm$^{-1}$ of the polymer backbone. Upon completion of the polymerization (ca. 24 h), the solid was dissolved in chloroform, precipitated in methanol, separated, and dried to obtain light yellow solid.

Organic azides were coupled to the polymers via 'click' chemistry. To the stirring polymer solution in tetrahydrofuran under inert atmosphere, azide compound (1.0 mol equiv per alkyne unit), triethyl amine or DBU (6.0 mol equiv per alkyne unit) and CuI (10 mol %) were added. The reaction mixture was stirred overnight under an argon atmosphere. Coupling of small molecules azides to alkyne side chains in polymers was monitored by FTIR analysis. Upon completion of the reaction, the resulting polymer was washed with THF and/or diethyl ether, separated by filtration and dried under reduced pressure. Basic polymers were acidified with a few drops of dilute HCl and carboxylic acid functionalized polymer was treated with a few drops of saturated solution of $NaHCO_3$ to increase water solubility. Acidic and basic polymer solutions were then filtered through centrifugal filters (Amicon Ultracel®, MWCO 3K Da, Merck Millipore Ltd) to remove residual small molecules and washed with water until free from free acid or base as tested with litmus paper. The polymers were then used to suspend SWCNTs.

Example 3: Nanoscale Sensors for Quantitative Redox Potential Measurement

Reduction potential (or Redox) is a physical concept used to measure the tendency of chemical compounds (couples) to transfer electrons during a reaction, and by extension the chemical potential energy in a system or couple. The direction, regulation, and capacity for cellular activity depends upon the state of these redox reactions, quantifiable with an electric potential voltage, for phenomena as diverse as energy production, biosynthesis, gene expression, signaling and detoxification. Redox Biology currently remains largely qualitative. Recent linkage between perturbations in redox state and cancerous transformation, cell growth and division, cell viability, drug efficacy, and numerous pathologies have increased interest in quantitative Redox Biology.

In certain embodiments, the compositions described herein allow for a Single-Walled Carbon Nanotube (SWCNT) based optical sensor for this purpose. Current art is not capable of measuring this parameter in living samples or using materials that have commercialization capability for wide spread use across diverse markets.

In certain embodiments, this sensor utilizes the optical fluorescence properties of SWCNTs dispersed with a unique Polycarbodiimide (JB-2-18 or JB-2-104) which enables the aqueous dispersed SWCNT to assume an electronic structure responsive to voltage change in the physiologically relevant redox potential range of approximately −150 millivolts to −400 millivolts. The ability of SWCNTs to sensitively respond to applied voltage has been tested and modeled in non-aqueous systems. The sensor directly measures this parameter within aqueous systems using non-invasive near infrared fluorescence emission.

The link between redox state and disease makes accurate measurement of redox increasingly important, both as a direct mechanism of pathology or as an indirect biomarker for screening. Human pathologies linked to aberrant redox state at either the mechanistic or biomarker level include, but are not limited to, sepsis, renal disease, cardiovascular disease, cancer carcinogenesis and therapy, inflammation, Alzheimer's disease, Parkinson's disease, Traumatic Brain Injury, Autism, atherosclerosis, Schizophrenia and Bipolar Disorder, Metabolic disorders, wounding and tissue regeneration, skin and cellular aging, skin damage and carcinogenesis, and gastrointestinal inflammation and disease. All basic research applications on various diseases can benefit greatly from a commercial tool for the measurement of redox potential for discovery of mechanisms, biomarkers, and screening therapies.

Current and future biomarkers relating disease to aberrant redox potentials or abnormal redox couples must be measured and detected in clinical chemistry laboratories for patient diagnostics. In certain embodiments, this sensor is useful as a measurement tool for diagnosing patients in clinical settings. The sensors are non-degradable and require no special storage, reducing the need for upkeep of traditional machinery and biochemical tools like antibodies and enzymes.

Given increasing evidence for the role of oxidants and redox couples in skin aging, skin cancer, and skin damage, in certain embodiments, an available microneedle delivery process delivers nano-sensors to, and embeds within, the epidermal layers of the skin for constant monitoring of extracellular redox. For example, current delivery platforms are commercially available from 3M Company. Measurement of redox via fluorescence emission is obtained with light directed at the skin at wavelengths innocuous to tissue. This gives consumers and physicians the ability to track skin exposure and damage from oxidants/chemicals and radiation, tracking of possible pre-cancerous abnormalities, and/or determination of post-cancer treatment efficacy and progression. Furthermore, because epidermal skin is constantly shed in 2-3 week cycles, this sensor is temporary, therefore affording no personal risk.

In other embodiments, these nano-sized sensors are fabricated on chip platforms and integrated with technology thereby giving consumers the ability to measure the redox potential of consumer products or solutions in daily life in a mobile fashion where, for example, this sensor is integrated into smart phone platforms as an additional plug-in application and attachment. Furthermore, physicians can similarly use this technology as a quick tool to analyze fluids. The redox potential of fluids, for example, changes markedly if pathogens are present and proliferating. Given that many consumer products on the market are formulated with strict chemical constituents or various solutions (skin care products, foods) the redox potential measured can indicate the quality or harm of a product and its stability over time.

Industrial and process engineering sectors require measurement of redox potential to monitor solution quality of dyes, foods, chemicals, microorganism growth media, and cosmetics. For example, fermentation of yeast for industrial scale alcoholic beverage production requires quality control including redox measurement of samples at various stages of development. Similar process control exists for other industries. Most of these measurements currently require large expensive probes and machinery. Furthermore, the volume of sample taken from production to measure can be significant. In certain embodiments, nano-sensors described herein, developed in the redox range of interest, can be used to continuously monitor this measurement in real time and decrease significantly the volume needed for measurement.

In an experimental example, a nano-sensor was fabricated by mixing Single-Walled Carbon Nanotubes (SWCNTs), available from various distributors, in a 1:10 ratio by weight with polycarbodiimide, solubilized in water. The mixture is then probe tip sonicated at 30% amplitude and approximately 4-5 Watts for 20 minutes. This resulting dispersion is then worked up: ultracentrifugation for 30 minutes, cut-off filtration using a benchtop centrifuge 2-3 times for 6 minutes each, re-dilution in water, and a final benchtop centrifugation at maximum force for 20 minutes. The resulting dispersion is ready for use, but may be subjected to an additional optional step.

Using the sensor merely requires addition of the final dispersion into the medium to be measured, or into the cell culture media for incubation and uptake via cellular processes. The concentration of the sensor dispersion can be gathered by taking the absorption of the solution at 630 nm, and dividing the valley by a known coefficient, for a result in mg/L.

In certain embodiments, detection of fluorescence emission requires an excitation source, preferentially a laser, at a wavelength near the resonant absorption of the proper nano-sensor chirality. Unlike organic fluorophores, nanotubes absorb off-resonant light; therefore, many lasers commonly used today are compatible. As with other optical tools, an appropriate filter set and infrared camera are used to detect the emission signal.

Analysis of data is similar to analysis of other fluorescence data currently in use. Information with nanotubes is usually gathered as spectra where differences, intensity, and chromatic shifting in peaks are analyzed, or via tracking of individual sensors in microscopy, whereby spectral and spatial information is collected from samples (i.e. cells).

FIGS. 13A-13B depict schematics showing the manufacturing of a nano-sensor dispersion, according to an illustrative embodiment. FIGS. 14A-14B show illustrative data from a nano-sensor dispersion. As shown in FIG. 14A, the data show the linear response of a nano-sensor to decreasing reduction potential, mediated in a buffered aqueous biological solution of cysteine and ascorbate as major redox couples. Each marked line represents a uniquely responding chiral nanotube within the same sensor population. As shown in FIG. 14B, the data shows that different chiralities of the sensor act together to form a ratiometric fluorescence response, thereby allowing quantitative measurement.

Example 4: Helical Polymers for Pretargeted Radioimmunotherapy

Recently Orcutt et al. reported a novel scFv antibody ("C825") with pM affinity for low molecular weight (MW) 1,4,7,10-tetraazacyclododecane-1,4,7,10-tetraacetic acid (DOTA) complexes with various metallic lanthanides including yttrium (Y) and lutetium (Lu) (Orcutt K D, Slusarczyk A L, Cieslewicz M, Ruiz-Yi B, Bhushan K R, Frangioni J V, et al. Engineering an antibody with picomolar affinity to DOTA chelates of multiple radionuclides for pretargeted radioimmunotherapy and imaging. Nuclear medicine and biology. 2011; 38:223-33.). Specifically intended for pretargeted radioimmunotherapy (PRIT), Orcutt and colleagues also prepared bi-specific antibodies having the format IgG-scFv which incorporated the sequences for C825, as well as those for IgG antibodies with high affinity and specificity for cancer cell-surface targets (e.g. carcinoembryonic (CEA) antigen). During PRIT in vivo with the IgG-C825 constructs, the IgG-C825 was initially administered and ample time was allowed for accumulation at the tumor, followed with a clearing agent to remove freely circulating IgG-C825. In the last step, a low-MW DOTA-hapten would be administered, which would be recognized by prelocalized IgG-C825. In order to obtain optimum therapeutic index, the DOTA-hapten would show rapid blood clearance via the renal route, as well as low non-specific uptake and retention in normal tissues, including those associated with the reticuloendothelial system (RES). With rapid clearance and minimum retention in tissues, the residence time of the radioactivity is minimized, thus reducing the absorbed dose to those tissues (and consequently limiting the maximum tolerated dose). The biodistribution and clearance properties of various DOTA-haptens have been described by Orcutt and colleagues.

Experiments described herein show that the DOTA-Bn-polymers can be radiolabeled with Lu-177 with radiochemical purities sufficient for in vivo biodistribution studies. Radioactivity in blood was 0.131±0.125% ID/g at 2 hr post-injection, indicating rapid clearance from circulation. As shown in FIG. 15, the activities in liver, spleen, and kidney ranged from 1-2% ID/g suggesting that clearance from blood primarily occurred from the kidney, as typically hepatic/RES clearance is slow in comparison and shows high and prolonged uptake/retention in the liver and spleen (e.g. liposomes). In all other organs assayed (including s.c. human tumor xenograft, heart, lungs, stomach, small and large intestines, muscle, and bone), the radioactivity concentrations were consistently less than 1% ID/g at 2 hr p.i. suggesting low uptake and retention in those tissues.

These DOTA-Bn-polymers are useful not only because of their favorable clearance and biodistribution properties, but also because of their multivalent design (i.e. greater than 1 DOTA/polymer). It has been reported that there is improvement in overall tumor uptake during pretargeted radioimmunotherapy with radioactive bivalent "janus" haptens in comparison with monovalent haptens. The DOTA/polymer stoichiometry allows for addition of a radioactive DOTA-metal complex or for which C825 does not show pM affinity (e.g. copper or actinium), followed by cold lutetium or yttrium metal. This allows for the non-radioactive Y/Lu-DOTA present on the polymer to serve as an affinity handle for antibody recognition and capture. Pretargeting GD2-positive solid tumors in mice with antibody-streptavidin fusions has been shown. However, instead of using radioactive biotin as the targeting hapten, two radiolabeled biotinylated peptides and radiolabeled and biotinylated bovine serum albumin can also be effectively used. Thus, small peptides and proteins can be targeted via biotinylation and the pretargeting strategy.

As described herein, the DOTA-Bn-polymer was supplied as a light yellow dry powder. A stock solution was prepared by adding 200 µL of 0.5 M ammonium acetate pH 5.3 to 5 mg of DOTA-Bn-polymer (25 mg/mL). The resulting solution appeared as a suspension, and stored at −20° C. To radiolabel with Lu-177, 20 µL of the stock was added to an acid-washed plastic Eppendorf tube, followed with 10 µL of DMSO and an additional 100 µL 0.5 M ammonium acetate pH 5.3 (e.g., to solubilize the DOTA-Bn-polymer). To this solution, 11.55 mCi (427.4 MBq) of Lu-177 was added (as $^{177}$LuCl3 in 0.05 N HCl, specific activity: 170 MBq/nmol; Perkin Elmer), the reaction was vortexed to mix, and the reaction was incubated at 80° C. for 90 min. To chelate any remaining free metal, 15 µL of 50 mM DTPA pH 7 was added, and the reaction was allowed to incubate for an additional 10 min at room temperature. To separate the $^{177}$Lu-DOTA-Bn-polymer from $^{177}$Lu-DTPA, the crude reaction was applied to a PD-10 desalting column (Sephadex G-25; greater than 5000 $M_r$; GE Healthcare) that was pre-equilibrated with saline for injection, and eluted with additional saline. According to the manufacturer, the void volume is ~2.5 mL, and the total column volume is 8.3 mL. The radioactivity concentrations in each elution fraction as well as the column itself were determined by assay in a Capintec CRC-25R dose calibrator using the manufacturer's recommended settings for the isotope.

TABLE 1

| Fraction | Volume | Lu-177 activity |
|---|---|---|
| 1 | reaction (~160 µL), | 0 |
| 2 | 1 mL | 0 |
| 3 | 1 mL | 66.8 |
| 4 | 1 mL | 436 |
| 5 | 0.5 mL | 470 |
| 6 | 0.5 mL | 674 |
| 7 | 0.5 mL | 910 |
| 8 | 0.5 mL | 1025 |

After collection of the $8^{th}$ fraction (total load+elution=~5.2 mL), the column was assayed in the dose calibrator (7.68 mCi, 66% of applied radioactivity). The radiochemical purity (RCP) of fractions 4 and 5 were assayed by thin-layer chromatography (Baker-flex Silica Gel IB-F; elution solvent 1/1 methanol/10% sodium acetate (aq); $^{177}$Lu-DOTA-Bn-polymer $R_f$=0.125-0.15, $^{177}$Lu-DTPA $R_f$~1). The plate radioactivity was assayed using a Bioscan radioTLC scanner. Fraction 4 showed a single peak with an $R_f$=0.125, while fraction 5 showed 2 peaks (major peak: 86.1% of total radioactivity on plate $R_f$=0.125; minor peak: 13.9% of plate radioactivity $R_f$=0.15). Fraction 3 was assumed to have the same radiochemical purity as fraction 4. Fractions 3, 4, and 5 were combined for injection (overall RCP~90% of radioactive species with $R_f$=0.125). For injection, doses comprising of 82.4-90.4 µCi of $^{177}$Lu-activity (presumably as $^{177}$Lu-DOTA-Bn-polymer) were formulated in 200 µL final volume of saline.

Two groups (n=5/group) of athymic nu/nu female nude mice (6-8 weeks old; Harlan Sprague Dawley) bearing IMR32-Luc subcutaneous xenografts in the lower flank (average size 1.47 g or 1.39 cm³ assuming a density of 1.05 g/mL) were injected intravenously with $^{177}$Lu-DOTA-Bn-polymer using the tail vein. One of the groups was sacrificed 2 hr post-injection (p.i.) and the other at 24 hr p.i. for ex vivo assay of radioactive biodistribution. Mice were euthanized, and tumor and selected organs were harvested, weighed, and radioassayed by gamma scintillation counting (Perkin Elmer Wallac Wizard 3"). Count rates were converted to activities using a system calibration factor, decay corrected and normalized to the administered activity, and expressed as percent injected dose per gram (% ID/g).

Example 5: Opiate Polycarbodiimide Conjugates for Drug Delivery and Peripheral Analgesia Two polycarbodiimide polymers containing opiate substituent groups were synthesized.

The first (P32) was found to translocate rapidly into the nuclei of certain cells. The polymer is able to translocate fully into the nucleus within three hours after administration in vitro. The construct is able to transport large materials, including carbon nanotubes, into the nucleus. Representative images are shown in FIG. 16.

The P33 construct was constructed to function as a peripherally acting opiate analgesic with a preferable side-effect profile over morphine (low euphoria, respiratory depression, physical dependence, addiction), and long-lasting analgesic efficacy above morphine. In vitro and in vivo data of both P32 and P33 polymers are presented in Table 2 below.

TABLE 2

| | Binding in Opioid transfected CHO cell lines subcutaneously | | | Analgesia in CD1 mice given | |
|---|---|---|---|---|---|
| | Ki (nM) | | | | ED50 |
| | MOR | DOR | KOR | 6TM/E11 | (mg/kg) |
| P32 | 1.25 ± 0.34 | 13.11 ± 2.88 | 0.56 ± 0.01 | 12.67 ± 2.1 | not analgesic |
| P33 | 3.45 ± 0.55 | 5.88 ± 0.79 | 0.85 ± 0.18 | 10.75 ± 0.9 | 10 |

Terminology:
MOR = Mu opiate receptor
DOR = Delta opiate receptor
KOR = Kappa opiate receptor
6TM/E11 = 6 transmembrane domain E11 splice variant of MOR Example 6: Radiolabeled Polymers as Multimodal Targeted Molecular Imaging Probes for Early Pancreatic Cancer Detection The present disclosure describes dual-modal positron emission tomography (PET) and fluorescent imaging agents with multimeric targeting ligands for enhanced receptor binding and multiple radiometal chelators for improved signal and high-resolution imaging. Molecular imaging probes based on the disclosed polymer-conjugates are well suited for various applications (e.g., cancer detection and therapeutics) because the polymers described herein i) integrate multimeric targeting ligands for receptors in cancer cells to achieve high tumor specific uptake and retention, ii) contain multiple chelators to chelate multiple radiometals for enhanced specific activity and quantitative PET imaging, and iii) allow tunable hydrophilicity through minimal structural changes to increase plasma stability, prolong probe circulation in vivo, improve pharmacokinetics, and reduce immunogenicity. The modular aspect of these 'clickable' polymer scaffolds allows for a library of derivatives to be quickly synthesized to tune their in vivo properties, as described above. In certain embodiments, a major advantage to these polymer scaffolds is the ability to easily change the peptide to change the molecular target and to change the chelator (e.g. DOTA instead of DFO) to change the radiometal. Changing the targeting peptide allows for these systems to target a theoretically limitless number of molecular targets, and changing the radiometal allows for PET or SPECT imaging with a variety of radiometals with different emission properties and half-lives. Moreover, the disclosed polymer scaffolds also provide opportunities for therapy using isotopes such as $^{177}$Lu and $^{90}$Y.

In certain embodiments, one advantage of this modular polymer scaffold is facile purification. For example, small peptide conjugates typically require HPLC purification and subsequent heating and solvent evaporation prior to formulation for injection. However, these polymer systems reach molecular weights of 15-30 kDa, allowing for efficient purification using disposable size exclusion columns (PD-10) and disposable spin-filters (Amicon). This type of system is amenable for making kit formulations. As a result, these systems can be deployed in a hospital radiopharmacy setting, unlike conventional small peptide conjugates which require HPLC purification by an expert radiochemist.

Synthesis of a DFO-Conjugated Polymer, Radiolabeling, and In Vitro Stability Tests Polycarbodiimide polymers conjugated with the radiometal chelator, desferrioxamine B (DFO), a hexadentate ligand that chelates $^{89}$Zr under mild conditions, fluorophore (IR650 dye), and PEG side chains (DFO-JBP1) were synthesized as shown in FIG. 17. $^{89}$Zr PET tracer emits low energy positrons and exhibits a relatively long half-life (78.41 h) that facilitates high imaging resolution and allows imaging at multiple time points, for example as described by Deri et al J. Med. Chem. 2014. The synthesized DFO-conjugated polymer (DFO-JBP1) was efficiently (greater than 99%) radiolabeled with $^{89}$Zr within 60 minutes at room temperature. The radiochemical purity was greater than 99.9% as determined from radio-iTLC as is shown in FIG. 18A. Without having to be bound by theory, negligible radiolabeling in control experiments with a similar polymer without DFO-conjugation (mPEG-JBP2, FIG. 18B) suggests lack of non-specific labeling from polymer backbone. Table 3 shows that the concentration dependent $^{89}$Zr labeling of DFO-JBP1 showed near quantitative radiolabeling with 100 µCi activities in 10 µg polymer.

TABLE 3

Concentration Dependent Radiolabeling

| Polymer weight (µg) | Initial activity (µCi) | 89Zr-Radiolabeling (%) of DFO-JBP1 |
|---|---|---|
| 1 | 100 | 16.6 |
| 10 | 100 | 97.6 |
| 30 | 100 | >99 |
| 100 | 100 | >99 |
| 200 | 100 | >99 |
| 400 | 100 | >99 |

As shown in Table 3, the highest specific activities detected were 13 mCi/mg polymers. Serum stability test on the $^{89}$Zr-radiolabeled polymer ($^{89}$Zr-DFO-JBP1) in the presence of human blood serum showed 98-99% stability over seven days (FIG. 18C). The $^{89}$Zr radiolabeling of the polymer achieved high specific activities (e.g., 13 mCi/mg) enabling a low dose injection in mice.

PET Imaging and Biodistribution of Radiolabeled Polymer in Healthy Mice $^{89}$Zr-labeled polymer without targeting ligands was i.v. injected (~100 µCi, ~10 µg) into healthy mice (BALB/c) and imaged at three time points (2 h, 24 h, and 72 h) using PET (FIG. 19A). At 2 h post injection, the majority of radioactivity was detected in the blood, and at 24 h significant radioactivity was still detected in blood indicating a long circulation time. Polymer derivatives with conjugated targeting peptides can benefit from this long circulation time for higher tumor uptake. Overtime, most radioactivity was detected in the liver. The ex vivo biodistribution performed at 96 h post injection matched the trend with PET images with the highest activity detected in the liver (FIG. 19B).

Materials and Methods

Chemicals

Reagents were purchased from Sigma-Aldrich, Milwaukee, Wis., Acros Organics, and Fisher Scientific, Fair Lawn, N.J., and used as received. Neutral silica gel (Ultrapure 60-200 µm, 60 Å, Acros Organics) was used in column chromatography purification of monomers. Anhydrous and inhibitor-free tetrahydrofuran (THF) was used for click chemistry.

Material Characterization

NMR data were recorded on a Bruker Advance III Ultrashield Plus 500 MHz spectrometer at room temperature. The chemical shift values were reported relative to TMS (δ=0.00 ppm) as an internal standard. Fourier transform infrared (FTIR) spectra were acquired using a Bruker Optics Tensor 27 FTIR spectrometer using ATR cell (Pike technologies). Wavenumbers in cm' are reported for characteristic peaks. All manipulations for polymerization were done at room temperature inside an MBraun UNIlab drybox under inert atmosphere. High resolution mass spectra (HRMS) were obtained on a Waters LCTPremier XE mass spectrometer by electrospray ionization. Size exclusion chromatography (SEC) was performed on a Viscotek GPCmax system (Malvern Instruments) equipped with ViscoGEL columns (IMBMMW-3078 and I-MBLMW-3078 in series) connected to a Viscotek TDA 305 triple detector array at 30° C. using THF as an eluent to determine relative molecular weights of the polymers. Polystyrene standards were used for the calibration of the instrument. Polymer samples were dissolved in the solvent system containing 0.12 M diethanolamine in THF, and the solutions were filtered through 0.45 µm PTFE filters prior to injection. The flow rate was 1.0 mL/min, and injector volume was 100 µL. OmniSEC software was used to calculate the molecular weight. The polymer-SWCNTs zeta potential measurements were carried out in a Zetasizer Nanoseries (Malvern Instruments).

Synthesis and Characterization of Compounds

Urea derivatives, monomers, and corresponding polymers (FIG. 20) were prepared as described below (Budhathoki-Uprety, J.; Novak, B., Synthesis of Alkyne-Functionalized Helical Polycarbodiimides and their Ligation to Small Molecules using 'Click' and Sonogashira Reactions Macromolecules 2011, 44 (15), 5947-5954). Molar ratio of monomer to catalyst was limited to 25:1 (Poly-1) or 32:1 (Poly-2) to obtain low molecular weight polymers to improve aqueous solubility.

1-(3-ethynylphenyl)-3-propylurea, Compound 1

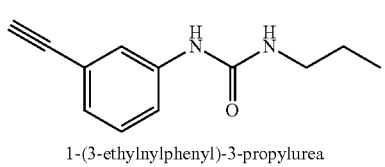

1-(3-ethylnylphenyl)-3-propylurea

3-Amino phenylacetylene (1.0 g, 8.53 mmol, 1.0 equiv) was diluted in anhydrous dichloromethane (25 mL) and added to n-propylisocyanate (0.87 g, 10.24 mmol, 1.2 equiv) in dichloromethane (10 mL), stirred at low temperature, and kept cold in an ice bath. The reaction mixture was allowed to warm to room temperature followed by reflux overnight. The solvent was removed in a rotary evaporator and crude white solid was purified by recrystallization in ethanol at 4° C. and dried to obtain white crystalline solid 1. 1H NMR (500 MHz, CDCl3, δ ppm): reference TMS=0 ppm, δ=7.99 (s, 1H), 7.39 (s, 1H), 7.26 (d, 1H), 7.15-7.08 (m, 2H), 6.02 (s, br, 1H), 3.11-3.07 (m, 2H), 2.99 (s, 1H), 1.45-1.38 (m, 2H), 0.83 (t, J=7.5 Hz, 3H). 13C NMR (125 MHz, CDCl3, δ ppm): reference CDCl3=77.23 ppm, δ=156.9, 139.4, 129.1, 126.6, 123.4, 122.8, 120.7, 83.5, 77.3, 42.0, 23.4, 11.4. HRMS (ESI) [M+H]+m/z calcd for $C_{12}H_{15}N_2O$, 203.1184; found, 203.1187.

1-phenyl-3-(prop-2-yn-1-yl)urea, Compound 2

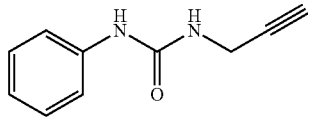

1-phenyl-3-(prop-2-yn-1-yl)urea

Propargyl amine (0.60 g, 10.89 mmol, 1.1 equiv) was diluted in anhydrous dichloromethane (20 mL) and added to phenylisocyanate (1.18 g, 9.90 mmol, 1.0 mol equiv) in dichloromethane (20 mL), stirred at low temperature, and kept cold in an ice bath. The reaction mixture was then allowed to warm to room temperature. A white precipitate resulted shortly after mixing with phenylisocyanate. The reaction mixture was allowed to stir for 3 hours. The white solid was then separated and purified by recrystallization in dichloromethane at 4° C. to obtain white crystalline solid 2. 1H NMR (500 MHz, DMSO-d6, δ ppm): reference DMSO-d6=2.50 ppm, δ=8.56 (s, 1H), 7.40 (d, J=7.65 Hz, 2H), 7.23 (t, J=7.60 Hz, 2H), 6.91 (t, J=7.35 Hz, 1H), 6.45 (t, J=5.60 Hz, 1H), 3.90 (dd, J=5.70 Hz, 2.45 Hz, 2H), 3.09 (t, J=2.45 Hz, 1H). 13C NMR (125 MHz, DMSO-d6, δ ppm): reference DMSO-d6=39.51 ppm, δ=154.7, 140.1, 128.6, 121.4, 117.8, 82.1, 72.9, 28.7. HRMS (ESI) [M+H]+m/z calcd for $C_{10}H_{11}N_2O$, 175.0871; found, 175.0863.

3-ethynyl-N-((propylimino)methylene)aniline, Compound 3

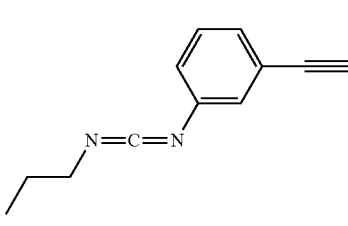

3-ethynyl-N-((propylimino)methylene)aniline

Triethyl amine (2.07 g, 20.51 mmol, 2.5 equiv) was added to a suspension of dibromotriphenylphosphorane (4.15 g, 9.84 mmol, 1.2 mol equiv) in dichloromethane (2 mL) and stirred at low temperature under inert atmosphere. After stirring the mixture for 5 minutes, compound 1 (1.66 g, 8.20 mmol, 1.0 equiv) was added and the reaction mixture and stirred until completion. The dehydration of the urea derivative into carbodiimide monomer was monitored by the formation of a very strong FTIR signal at ~2120-2140 cm-1. Upon completion of the reaction, hexane was added to precipitate side products. The monomer compound was then extracted from solid by hexanes. Crude monomer was further purified by column chromatography on silica gel using ethyl acetate:hexanes (1:2) and dried under reduced pressure to obtain 3 as a colorless oil. 1H NMR (500 MHz, CDCl3, δ ppm): reference TMS=0 ppm, δ=7.20 (m, 3H), 7.07-7.04 (m, 1H), 3.39 (t, J=6.8 Hz, 2H), 3.07 (s, 1H), 1.73-1.1.69 (m, 2H), 1.01 (t, J=7.4 Hz, 3H). 13C NMR (125 MHz, CDCl3, δ ppm): reference CDCl3=77.23 ppm, δ=141.3, 129.5, 128.4, 127.1, 124.3, 123.3, 120.9, 83.2, 77.7, 48.7, 24.9, 11.6. FTIR (thin film, cm-1): characteristic absorption from terminal alkyne group and monomer; 3290 (terminal alkyne), 2123 (vs, carbodiimide).

N-((prop-2-yn-1-ylimino)methylene)aniline, Compound 4

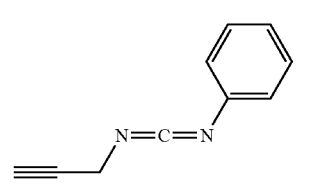

N-((prop-2-yn-1-ylimino)methylene)aniline

The same procedure as described in the synthesis of compound 3 was employed. 1H NMR (500 MHz, CDCl3, δ ppm): reference TMS=0 ppm, δ=7.31-7.28 (m, 2H), 7.16-7.14 (m, 3H), 4.08 (d, J=2.45 Hz, 2H), 2.44 (t, J=2.50 Hz, 1H). 13C NMR (125 MHz, CDCl3, δ ppm): reference TMS=0 ppm, δ=139.5, 139.0, 129.4, 125.5, 124.0, 79.0, 73.5, 36.0. FTIR (thin film, cm-1): characteristic absorption from terminal alkyne group and monomer; 3302 (terminal alkyne), 2119 (vs, carbodiimide). HRMS (ESI) [M+H]+m/z calcd for $C_{10}H_9N_2$, 157.0766; found, 157.0761.

Synthesis of Catalyst

The catalyst was synthesized and characterized following previously described procedure (Tang, H.; Boyle, P.; Novak, B., Chiroptical switching polyguanidine synthesized by helix-senseselective polymerization using [(R)-3,3'-dibromo-2,2'-binaphthoxy](di-tert-butoxy)titanium(IV) catalyst. J. Am. Chem. Soc. 2005, 2136-2142).

Synthesis of Polymers

Polymers were synthesized following the reported procedure1. Briefly, the catalyst, either neat or dissolved in chloroform (0.2 mL per 500 mg monomer) was added to the monomer at room temperature and under inert atmosphere. The reaction mixture turned to dark red and solidified to an orange red solid. The polymerization process was monitored in FTIR by disappearance of IR signals from carbodiimide (~2140-2120 $cm^{-1}$) and formation of new IR absorption at ~1620-1640 $cm^{-1}$ of the polymer backbone. Upon completion of the polymerization (ca. 24 h), the solid was dissolved in chloroform, precipitated in methanol, separated, and dried to obtain light yellow solid.

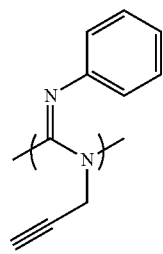

Poly-1

FTIR (thin film, cm-1): characteristic absorption from terminal alkyne group and polymer backbone; 3304 (terminal alkyne C—H), 2123 (alkyne triple bond, CC), 1631 (imine in polymer backbone, C=N). 1H NMR (500 MHz, CDCl3, δ ppm): reference TMS=0 ppm, δ=7.28-6.84 (br), 5.35-5.29 (br), 4.37-4.20 (br), 3.14 (br), 2.07-0.75 (br).

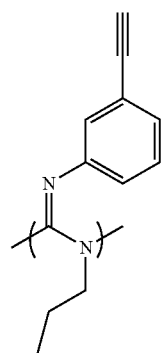

Poly-2

FTIR (thin film, cm-1): characteristic absorption from terminal alkyne group and polymer backbone, 3300 (terminal alkyne C—H), 2123 (w, alkyne triple bond, CC), 1624 (imine in polymer backbone, C=N). Mn=13, 346, PDI=1.29. 1H NMR (500 MHz, CDCl3, δ ppm): reference TMS=0 ppm, δ=7.15-6.49 (br), 3.45 (br), 3.19 (br), 3.03 (br), 2.53 (br) 1.01-0.70 (br).

FIGS. 21A-21B show the FTIR spectra of polymers, Poly-1 and Poly-2, respectively.

Synthesis of Azides

Azide compounds, as shown in FIG. 22, were synthesized and characterized following literature procedures (Inverarity, I. A.; Hulme, A. N., Marked small molecule libraries: a truncated approach to molecular probe design. Organic & Biomolecular Chemistry 2007, 5 (4), 636-643; Srinivasan, R.; Tan, L. P.; Wu, H.; Yang, P.-Y.; Kalesh, K. A.; Yao, S. Q., High-throughput synthesis of azide libraries suitable for direct "click" chemistry and in situ screening. Organic & Biomolecular Chemistry 2009, 7 (9), 1821-1828; Budhathoki-Uprety, J.; Peng, L.; Melander, C.; Novak, B. M., Synthesis of Guanidinium Functionalized Polycarbodiimides and Their Antibacterial Activities. ACS Macro Lett. 2012, (1), 370-374).

Coupling of azides 5-7 to Poly-1 and Poly-2 via 'click' chemistry to prepare Poly-3-8.

To the stirring polymer solution in tetrahydrofuran under inert atmosphere, azide compound (2.0 mol equiv per alkyne unit), triethyl amine or DBU (6.0 mol equiv per alkyne unit) and CuI (10 mol %) were added. The reaction mixture was stirred overnight under an argon atmosphere. Coupling of small molecules azides to alkyne side chains in polymers was monitored by FTIR analysis. Upon completion of the reaction, the resulting polymer was washed with THF and/or diethyl ether, separated by filtration and dried under reduced pressure. FTIR analysis of final polymers showed full conversion of all alkyne repeat units in click reaction. Limited solubility of final polymers posed difficulty in GPC measurements. Amine-Poly-6, Amine-Poly-8, and Guanidine-Poly-4 were acidified with a few drops of dilute HCl to increase water solubility. Carboxy-Poly-7 was treated with a few drops of saturated solution of $NaHCO_3$. Acidic and basic polymer solutions were then filtered through centrifugal filters (Amicon Ultracel®, MWCO 3K Da, Merck Millipore Ltd) to remove residual small molecules and washed with water until free from free acid or base as tested with litmus paper. The polymers were then used to suspend SWCNTs.

Photoluminescence Excitation/Emission Contour Plots

Photoluminescence (PL) plots were constructed using a home-built apparatus comprising of a tunable white light laser source, inverted microscope, and InGaAs nIR detector. The laser was a SuperK EXTREME supercontinuum white light laser source (NKT Photonics) with a VARIA variable bandpass filter accessory capable of tuning the output 500-825 nm with a bandwidth of 20 nm. A longpass dichroic mirror (900 nm) was used to filter the excitation beam. The light path was shaped and fed into the back of an inverted IX-71 microscope (Olympus) where it passed through a 20×nIR objective (Olympus) and illuminated a 200 μL nanotube sample in a 96-well plate (Greiner). Emission from the nanotube sample was collected again by the 20× objective and diverted, via a long-pass dichroic mirror (875 nm), matched to the f/# of the spectrometer using several lenses, injected into an Isoplane nIR spectrograph (Princeton Instruments) with a slit width of 410 μm, and dispersed by a grating of 86 g/mm and 950 nm blaze wavelength. The light was collected by a PIoNIR InGaAs 640×512 pixel array (Princeton Instruments).

Excitation, emission, and wavelength corrections and calibrations were performed as follows. The power at each excitation wavelength was measured at the objective with a PM100D power meter (Thorlabs) from which a power spectrum was constructed and used to correct the emission intensities for nonuniform excitation. A HL-3-CAL-EXT halogen calibration light source (Ocean Optics) was used to correct for non-uniformities in the emission path arising from grating, detector, and lens inefficiencies. A Hg/Ne pencil style calibration lamp (Newport) was used to calibrate emission wavelengths ranging from 950-1350 nm.

Acquisition was conducted in semi-automated fashion controlled by Labview code which iteratively increased the excitation laser source from 491-824 nm in steps of 3 nm and saved the data in ASCII format. Using a center wavelength of 1135 nm, the emission spectra range was 915-1354 nm with has a resolution of 0.7 nm. Background subtraction was conducted using a well filled with DI H$_2$O. Following acquisition, the data was processed with a Matlab code which applied the corrections for non-uniform excitation and emission (as mentioned previously), created the contours with a Gaussian smoothing function, and output the figures to be used for nanotube peak picking.

Topical application of polycarbodiimide-SWCNT complexes on human skin.

Polycarbodiimide-SWCNT complexes (nanotube concentration in aqueous suspension: 70-90 mg/L) were deposited onto normal human skin after harvesting from patients during Moh's surgery. Normal skin at the periphery of the tumor was used; the tumor tissue was discarded. After a two-hour exposure to nanotubes, the skin surface was wiped off to remove unabsorbed nanotubes. The skin samples were then microtomed into 5 mm thick slices and imaged under 730 nm excitation.

What is claimed is:

1. An imaging method comprising:
   administering a composition to a biological sample to form a mixture, wherein the composition comprises an aqueous suspension of helical polymer-encapsulated carbon nanotubes, the helical polymer is a polycarbodiimide comprising (1) one or more aromatic groups incorporated in its monomer subunits, and (2) functional side chains comprising one or more members of the group consisting of an oligoethylene glycol group, a —CH$_2$CH$_2$NH$_2$ group, and a —CH$_2$C(O)OH group, and the aqueous suspension is a stable suspension in aqueous solution or in serum;
   exposing the mixture to excitation light; and
   detecting light emitted by suspension or fluorescent aggregates formed by one or more components of the composition in the mixture.

2. The method of claim 1, further comprising disrupting the fluorescent aggregates in the mixture to reverse the emission of light.

3. The method of claim 2, further comprising alternating between cycles of light emission and no light emission by re-aggregating and disrupting, respectively, the fluorescent aggregates in the mixture for high resolution biomolecular imaging.

4. The method of claim 1, wherein the detecting step comprises obtaining images of cellular nuclei of the biological sample.

5. The method of claim 1, wherein the carbon nanotubes are single-walled carbon nanotubes (SWCNTs).

6. The method of claim 1, wherein the polycarbodiimide comprises one or more monomeric species selected from the group consisting of

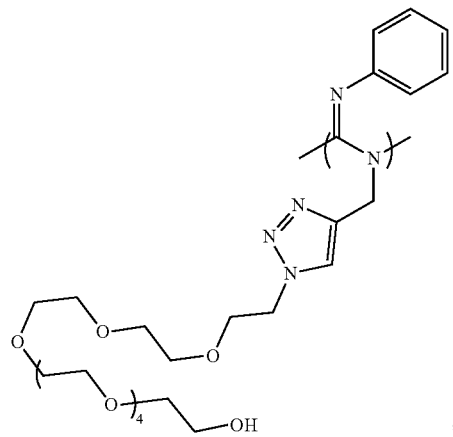

,

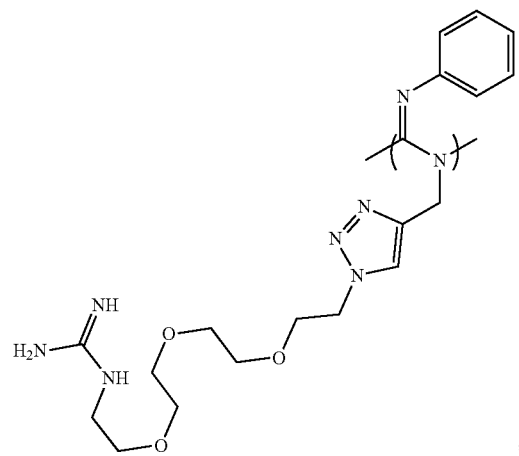

,

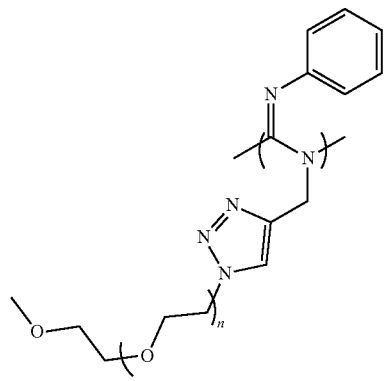

PEG20

-continued

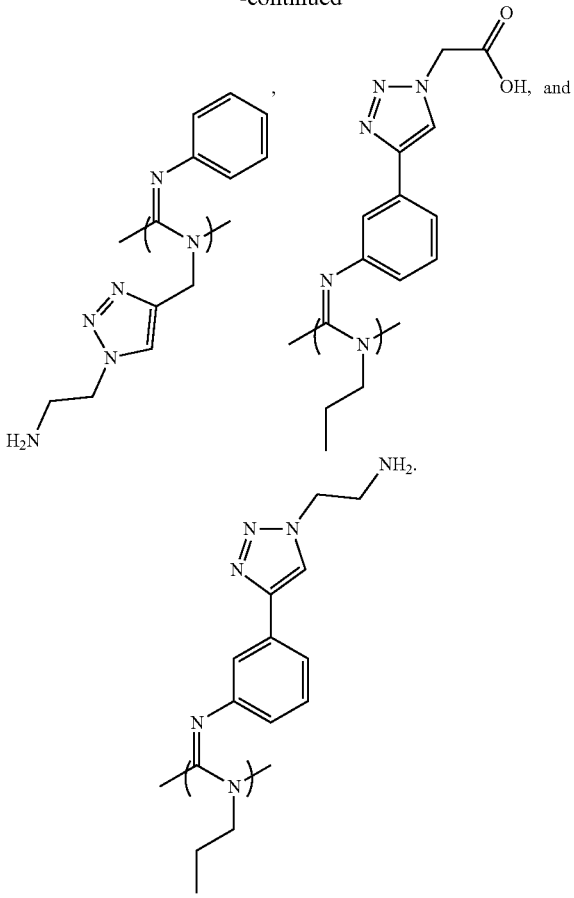

7. The method of claim 1, wherein at least a plurality of the helical polymer-encapsulated carbon nanotubes in the aqueous suspension are in van der Waals contact at a center-to-center distance between adjacent nanotubes sufficient to exhibit inter-nanotube Förster resonance energy transfer (INFRET).

8. The method of claim 7, wherein the center-to-center distance is from 1 nm to 4 nm.

9. The method of claim 7, wherein the helical polymer-encapsulated carbon nanotubes in van der Waals contact are not irreversibly bound.

10. The method of claim 7, wherein the composition comprises
(i) a first set of helical polymer-encapsulated carbon nanotubes each encapsulated by a helical polymer having at least a first substituent functional group; and
(ii) a second set of nanotubes each encapsulated by a helical polymer having at least a second substituent functional group, wherein the first substituent functional group and the second substituent functional group imbue the first and second sets of encapsulated nanotubes with sufficiently strong coulombic attraction to each other to form reversible fluorescent aggregates in the suspension.

11. The method of claim 1, wherein the functional side chains comprise one or more members selected from the group consisting of an oligoethylene glycol bearing a terminal primary amine, an oligoethylene glycol bearing a terminal carboxylic acid, an oligoethylene glycol bearing a terminal guanidine group, an oligoethylene glycol bearing a terminal methoxy, an oligoethylene glycol bearing a terminal hydroxyl, a —CH$_2$CH$_2$NH$_2$ group, and a —CH$_2$C(O)OH group.

12. The method of claim 1, wherein the one or more aromatic groups are configured to promote multi-valent π-π interactions between the helical polymer and the graphitic sidewall of the carbon nanotubes.

13. The method of claim 1, wherein the functional side chains comprise a targeting group.

14. The method of claim 1, wherein the functional side chains comprise an oligoethylene glycol group bearing a terminal primary amine, an oligoethylene glycol group bearing a terminal carboxylic acid, an oligoethylene glycol group bearing a terminal guanidine group, an oligoethylene glycol group bearing a terminal methoxy, or an oligoethylene glycol group bearing a terminal hydroxyl.

* * * * *